US006368846B1

(12) United States Patent
Hunter et al.

(10) Patent No.: US 6,368,846 B1
(45) Date of Patent: Apr. 9, 2002

(54) ECTOPARASITE SALIVA PROTEINS AND APPARATUS TO COLLECT SUCH PROTEINS

(75) Inventors: Shirley Wu Hunter; Gek-Kee Sim; Eric R. Weber, all of Ft. Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/171,156

(22) PCT Filed: Apr. 10, 1997

(86) PCT No.: PCT/US97/05959

§ 371 Date: Mar. 4, 1999

§ 102(e) Date: Mar. 4, 1999

(87) PCT Pub. No.: WO97/37676

PCT Pub. Date: Oct. 16, 1997

Related U.S. Application Data

(63) Continuation of application No. 08/630,822, filed on Apr. 10, 1996, now Pat. No. 5,840,695.

(51) Int. Cl.[7] .......................... C07H 21/00; C12N 1/20; C12N 1/14; C12N 5/00; C12N 15/00

(52) U.S. Cl. ............... 435/252.3; 435/348; 435/254.11; 435/320.1; 435/325; 530/350; 536/23.1; 536/23.5

(58) Field of Search ......................... 435/252.3, 254.11, 435/320.1, 325, 348; 536/23.1; 530/350

(56) References Cited

U.S. PATENT DOCUMENTS 5,356,622 A 10/1994 Heath et al. ............. 424/265.1
5,840,695 A * 11/1998 Frank et al. .................. 514/12

FOREIGN PATENT DOCUMENTS

WO WO 93/18788 9/1993
WO WO 96/11271 4/1996
WO WO 96/14089 5/1996
WO WO 96/28469 9/1996

OTHER PUBLICATIONS

Baker et al., 1975, *J. Small Anim. Pract.*, 16 (5):317–327.
Benjamin et al., 1963, *Exp. Parasitol.* 13:143–154.
Benjamin et al., 1960, *Exp. Parasitol.*, 10:214–222.
Greene et al., 1993, *Parasite Immunol.*, 15:69–74.
Greene et al., 1993, *Vet. Immunol. & Immunopathol.*, 37(1):15–23.
Halliwell et al., 1987, *Vet. Immunol. Immunopathol.*, 15:203–213.
Halliwell et al., 1985, *Vet. Immunol. & Immunopath*, 8(3):215–23.
Keep et al., 1967, *Austral. Vet. J.*, 43:425–426.
Kristensen et al., 1978, *Nord. Vet.–Med.*, 30:414–423.
Kunkle et al., 1985, *J. Amer. Vet. Medical Assn.*, 186(7):677–80.
McKeon et al., 1994, *Int. J. Parasitol.*, 24(2):259–63.
Michaeli et al., 1966, *J. Immunol.*, 97(3):402–406.
Michaeli et al., 1965, *J. Immunol.*, 95(1):162–170.
Van Winkle, 1981, *J. Amer. Anim. Hosp. Assoc.*, 17:343–354.
Wade et al., 1988, *J. Med. Entomol.*, 25(3):186–189.
Young et al., 1963, *Exp. Parasitol.*, 13:155–166.

* cited by examiner

*Primary Examiner*—Rebecca E. Prouty
*Assistant Examiner*—David J. Steadman
(74) *Attorney, Agent, or Firm*—Sheridan Ross P.C.

(57) ABSTRACT

The present invention is directed to a novel product and method for isolating ectoparasite saliva proteins, and a novel product and method for detecting and/or treating allergic dermatitis in an animal. The present invention also relates to ectoparasite saliva proteins, nucleic acid molecules having sequences that encode such proteins, and antibodies raised against such proteins. The present invention also includes methods to obtain such proteins and to use such proteins to identify animals susceptible to or having allergic dermatitis. The present invention also includes therapeutic compositions comprising such proteins and their use to treat animals susceptible to or having allergic dermatitis.

13 Claims, No Drawings

ECTOPARASITE SALIVA PROTEINS AND APPARATUS TO COLLECT SUCH PROTEINS

This application is a continuation of Ser. No. 08/630,822 filed Apr. 10, 1996, now U.S. Pat. No. 5,840,695.

FIELD OF THE INVENTION

The present invention relates to a novel product and method for isolating ectoparasite saliva proteins, and a novel product and method for detecting and/or treating allergic dermatitis in an animal.

BACKGROUND OF THE INVENTION

Bites from ectoparasites, in particular fleas, can cause a hypersensitive response in animals. In particular, hypersensitive responses to fleabites is manifested in a disease called flea allergy dermatitis (FAD). Hypersensitivity refers to a state of altered reactivity in which an animal, having been previously exposed to a compound, exhibits an allergic response to the compound upon subsequent exposures. Hypersensitive responses include immediate and delayed-type hypersensitivity, and in particular Type I, Type II, Type III and Type IV hypersensitivities (described in detail in Janeway et al., *Immunobiology*, Garland Publishing, New York, 1994, which is incorporated in its entirety by this reference).

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

FAD can have manifestations of both immediate and delayed-type hypersensitivity (described in detail in Janeway et al. ibid.). Effective treatment of FAD has been difficult if not impossible to achieve. FAD afflicts about 15% of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments.

Until the discovery of the novel formulations of the present invention, flea allergens responsible for FAD had not been clearly defined. Whole flea antigen preparations have been used to diagnose and desensitize animals with FAD (Benjamini et al., 1960, pp. 214–222*, Experimental Parasitology*, Vol. 10; Keep et al., 1967, pp. 425–426*, Australian Veterinary Journal*, Vol. 43; Kristensen et al., 1978, pp. 414–423*, Nord. Vet-Med*, Vol. 30; Van Winkle, 1981, pp. 343–354*, J. Amer. Animal Hosp. Assoc*., Vol. 17; Haliwell et al., 1987, pp. 203–213*, Veterinary Immunology and Immunopathology*, Vol. 15; Greene et al., 1993, pp. 69–74*, Parasite Immunology*, Vol. 15); PCT Publication No. WO 93/18788 by Opdebeeck et al.; and Van Winkle, pp. 343–354, 1981*, J. Am. Anim. Hosp. Assoc*., vol. 32. Available commercial whole flea extracts, however, are unpredictable and, therefore, have limited usefulness.

Prior investigators have suggested that products contained in flea saliva might be involved in FAD and have also suggested methods to isolate such products: Benjamini et al., 1963, pp. 143–154*, Experimental Parasitology*, Vol. 13; Young et al., 1963, pp. 155–166*, Experimental Parasitology* 13, Vol. 13; Michaeli et al., 1965, pp. 162–170*, J. Immunol*., Vol. 95; and Michaeli et al., 1996, pp. 402–406*, J. Immunol*., Vol. 97. These investigators, however, have characterized the allergenic factors of flea saliva as being haptens having molecular weights of less than 6 kilodaltons (kD). That they are not proteins is also supported by the finding that they are not susceptible to degradation when exposed to strong acids (e.g., 6 N hydrochloric acid) or heat. Some of the particular low molecular weight allergenic factors have also been characterized as being a highly fluorescent aromatic fraction (Young et al., ibid.). In addition, studies by such investigators have indicated that in order to be allergenic, such factors need to be associated with adjuvants and/or carriers, such as collagen or portions of the membrane used to collect the oral secretions. Moreover, the methods described to collect flea saliva factors were difficult and unpredictable. Furthermore the factors isolated by these methods were typically contaminated with material from the fleas, their culture medium or the skin-based membranes used to allow the fleas to feed.

Thus, there remains a need to more clearly define flea saliva allergens capable of inducing a hypersensitive response in animals. In addition, there remains a need to develop a method to collect substantially pure flea saliva allergens which provide predictable and less expensive preparations of allergens useful for desensitizing animals subject to, or having, FAD.

SUMMARY OF THE INVENTION

One embodiment of the present invention is an isolated nucleic acid molecule that hybridizes under stringent conditions with a gene including a flea saliva gene comprising a nucleic acid sequence including SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:71, SEQ ID NO:73, SEQ ID NO:74, SEQ ID NO:76 and a nucleic acid sequence encoding an amino acid sequence selected from the group consisting of SEQ ID NO:78 and SEQ ID NO:87.

The present invention also includes a nucleic acid molecule that hybridizes under stringent hybridization conditions with a nucleic acid molecule having a nucleic acid sequence encoding a protein comprising an amino acid sequence including SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87.

Another embodiment of the present invention includes an isolated protein encoded by a nucleic acid molecule that hybridizes under stringent hybridization conditions with a nucleic acid molecule having a nucleic acid sequence encoding a protein comprising an amino acid sequence including SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87.

Also included in the present invention are recombinant molecules and cells having a nucleic acid molecule of the present invention.

Another aspect of the present invention includes an antibody capable of selectively binding to an ectoparasite protein, or mimetope.

Yet another embodiment of the present invention is a therapeutic composition for treating allergic dermatitis comprising a formulation comprising at least one isolated ectoparasite saliva protein, wherein said ectoparasite saliva protein comprises at least a portion of an amino acid sequence, wherein said portion is encoded by a nucleic acid molecule that hybridizes under stringent hybridization conditions with a nucleic acid molecule having a nucleic acid sequence including SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:71, SEQ ID NO:73, SEQ ID NO:74, SEQ ID NO:76 and a nucleic acid sequence encoding an amino acid sequence selected from the group consisting of SEQ ID NO:78 and SEQ ID NO:87. A preferred therapeutic composition of the present invention also includes an excipient, an adjuvant and/or a carrier. Also included in the present invention is a method to desensitize a host animal to allergic dermatitis. The method includes the step of administering to the animal a therapeutic composition of the present invention.

Other embodiments of the present invention include methods to identify an animal susceptible to or having allergic dermatitis, using in vivo or in vitro methods. In one embodiment, an animal susceptible to or having allergic dermatitis is identified in vivo by the method comprising: (a) administering to a site on the animal a formulation comprising at least one isolated ectoparasite saliva protein, in which the ectoparasite saliva protein comprises an amino acid sequence including SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87; and (b) comparing a reaction resulting from administration of the formulation with a reaction resulting from administration of a control solution, in which the animal is determined to be susceptible to or to have allergic dermatitis if the reaction to the formulation is at least as large as said reaction to the positive control solution, and in which the animal is determined not to be susceptible to or not to have allergic dermatitis if the reaction to the formulation is about the same size as said reaction to the negative control solution.

In another embodiment, an animal susceptible to or having allergic dermatitis is identified in vitro by measuring the presence of antibodies indicative of allergic dermatitis in the animal using the method comprising: (a) contacting a formulation with a body fluid from an animal under conditions sufficient for formation of an immunocomplex between the formulation and the antibodies, if present, in the body fluid, the formulation comprising at least one isolated ectoparasite saliva protein, in which the ectoparasite saliva protein comprises an amino acid sequence including SEQ ID NO:53, SEQ ID NO: 62, SEQ ID NO:65, SEQ ID NO:70, SEQ ID NO:72, SEQ ID NO:75, SEQ ID NO:77, SEQ ID NO:78 and SEQ ID NO:87; and (b) determining the amount of immunocomplex formed, in which formation of the immunocomplex indicates that the animal is susceptible to or has allergic dermatitis.

The present invention further relates to an assay kit for testing if an animal is susceptible to or has allelic dermatitis, the kit comprising: (a) a formulation comprising at least one isolated ectoparasite saliva protein, in which the ectoparasite saliva protein comprises an amino acid sequence including SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO: 87; and (b) a means for determining if the animal is susceptible to or has allergic dermatitis, in which the means comprises use of the formulation to identify animals susceptible to or having allergic dermatitis.

DETAILED DESCRIPTION OF THE INVENTION

The present invention includes a novel product and method for diagnosing and treating allergic dermatitis of animals to ectoparasites.

According to the present invention, ectoparasites are external living parasites that attach and feed through the skin of a host animal. Ectoparasites include parasites that live on a host animal and parasites that attach temporarily to an animal in order to feed. Also, according to the present invention, ectoparasite saliva refers to the material released from the mouth of an ectoparasite when the ectoparasite attempts to feed in response to a temperature differential. Ectoparasite saliva includes ectoparasite saliva products.

One embodiment of the present invention is a formulation that contains ectoparasite saliva products that can be used to diagnose and/or treat animals susceptible to or having (i.e., suffering from) allergic dermatitis. Preferred types of allergic dermatitis to diagnose and/or treat using ectoparasite saliva products of the present invention include flea allergy dermatitis, Culicoides allergy dermatitis and mosquito allergy dermatitis. A preferred type of allergic dermatitis to diagnose and/or treat using ectoparasite saliva products of the present invention is flea allergy dermatitis. As used herein, an animal that is susceptible to allergic dermatitis refers to an animal that is genetically pre-disposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite saliva protein antibodies within an affected animal but no dermatitis). For example, sub-clinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is a formulation that includes one or more isolated ectoparasite saliva proteins. According to the present invention, an isolated protein is a protein that has been removed from its natural milieu. An isolated ectoparasite saliva protein can, for example, be obtained from its natural source, be produced using recombinant DNA technology, or be synthesized chemically. As used herein, an isolated ectoparasite saliva protein can be a full-length ectoparasite saliva protein or any homologue of such a protein, such as an ectoparasite saliva protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol). A homologue of an ectoparasite saliva protein is a protein having an amino acid sequence that is sufficiently similar to a natural ectoparasite saliva protein amino acid sequence that a nucleic acid sequence encoding the homologue is capable of hybridizing under stringent conditions to (i.e., with) a nucleic acid molecule encoding the natural ectoparasite saliva protein (i.e., the complement of a nucleic acid sequence encoding the natural ectoparasite saliva protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite saliva protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite saliva protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite saliva protein homologues can be the result of allelic variation of a natural gene encoding an ectoparasite saliva protein. A natural gene refers to the form of the gene found most often in nature. Ectoparasite saliva protein homologues can be produced using techniques known in the art including, but not limited to, direct modifications to a gene encoding a protein using, for example, classic or recombinant DNA techniques to effect random or targeted mutagenesis.

Preferred ectoparasite saliva proteins of the present invention, including homologues thereof, are capable of detecting and/or treating allergic dermatitis resulting from the bites of ectoparasites. A preferred ectoparasite saliva protein homologue includes at least one epitope capable of eliciting a hypersensitive response to the natural ectoparasite saliva protein counterpart. An ectoparasite saliva protein homologue can also include an epitope capable of hyposensitizing an animal to the natural form of the protein. The ability of an ectoparasite saliva protein homologue to detect and/or treat (i.e., immunomodulate or regulate by, for example, desensitizing) the hypersensitivity of an animal susceptible to or having allergic dermatitis, can be tested using techniques known to those skilled in the art. Such techniques include skin tests and immunoabsorbent assays as described in detail below. Additional preferred ectoparasite saliva proteins of the present invention have other activities that include activities important for feeding and survival of the ectoparasite.

In one embodiment, a formulation of the present invention can comprise a protein having at least a portion of an isolated ectoparasite saliva protein. According to the present invention, "at least a portion of an ectoparasite saliva protein" refers to a portion of an ectoparasite saliva protein encoded by a nucleic acid molecule that is capable of hybridizing, under stringent conditions, with a nucleic acid encoding a full-length ectoparasite saliva protein of the present invention. Preferred portions of ectoparasite saliva proteins are useful for detecting and/or treating allergic dermatitis resulting from the bites of ectoparasites. Additional preferred portions have activities important for flea feeding and survival. Suitable sizes for portions of an ectoparasite saliva protein of the present invention are as disclosed for saliva protein homologues of the present invention.

As will be apparent to one of skill in the art, the present invention is intended to apply to all ectoparasites. A formulation of the present invention can include saliva products from any ectoparasites. A preferred ectoparasite of the present invention from which to isolate saliva products (including proteins), and/or from which to identify proteins that can then be produced recombinantly or synthetically, include arachnids, insects and leeches. More preferred ectoparasites from which to obtain saliva products include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasite saliva products include those from fleas, mosquitos, midges, sandflies, blackflies, ticks and Rhodnius, with products from fleas, mosquitos and Culicoides being even more preferred.

A particularly preferred formulation of the present invention includes flea saliva proteins. Preferred flea saliva products include those from Ctenocephalides, Xenopsylla, Pulex, Tunga, Nosopsyllus, Diamanus, Ctopsyllus and Echidnophaga fleas, with saliva products from *Ctenocephalides canis* and *Ctenocephalides felis* fleas being even more preferred. For the purposes of illustration, many of the following embodiments discuss flea saliva proteins. Such discussion of flea saliva proteins is not intended, in any way, to limit the scope of the present invention.

In another embodiment, a formulation of the present invention includes at least a portion of an ectoparasite saliva protein homologue having at least a portion of one of the following amino acid sequences: SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87 and/or other sequences disclosed herein.

In one embodiment, a formulation of the present invention can include at least one isolated protein having (i.e., including) at least a portion of one of the amino acid sequences identified in the Sequence ID Listing, and more specifically an amino acid sequence selected from the group consisting of SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87.

It is to be appreciated that ectoparasite saliva proteins of the present invention include, but are not limited to, full-length proteins, hybrid proteins, fusion proteins, multivalent proteins, and proteins that are truncated homologues of, or are proteolytic products of, at least a portion of a protein having at least a portion of one of the following amino acid sequences: SEQ ID NO:53, SEQ ID NO:62, SEQ ID NO:65, SEQ ID NO:70, SEQ ID NO:72, SEQ ID NO:75, SEQ ID NO:77, SEQ ID NO:78, SEQ ID NO:87 and/or other sequences disclosed herein. As used herein, the term hybrid protein refers to a single protein produced from two different proteins.

The foregoing SEQ ID NO's represent amino acid sequences deduced according to methods disclosed in the Examples. It should be noted that since amino acid sequencing technology is not entirely error-free, the foregoing SEQ ID NO's, at best, represent an apparent amino acid sequence of the ectoparasite saliva proteins of the present invention. In addition, the variation seen in the foregoing SEQ ID NO's can also be due, at least in part, to allelic variation since the proteins being sequenced were derived from populations of fleas.

According to the present invention, a formulation of the present invention can include flea saliva proteins that have undergone post-translational modification. Such modification can include, for example, glycosylation. Glycosylation can include addition of N-linked and/or O-linked oligosaccharides. It is to be appreciated that post-translational modification of a protein of the present invention can contribute to an epitope's ability to induce an allergic response against the protein in an immediate or delayed hypersensitivity response.

Another embodiment of the present invention is an isolated nucleic acid molecule capable of hybridizing, under stringent conditions, with an ectoparasite saliva protein gene encoding an ectoparasite saliva protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated ectoparasite saliva protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an ectoparasite saliva protein of the present invention or to form stable hybrids under stringent conditions with natural nucleic acid molecule isolates.

An isolated nucleic acid molecule of the present invention can include a nucleic acid sequence that encodes at least one ectoparasite saliva protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite saliva protein. As heretofore disclosed, ectoparasite saliva proteins of the present invention include, but are not limited to, proteins having full-length ectoparasite saliva protein coding regions, portions thereof, and other ectoparasite saliva protein homologues.

It is to be appreciated that an ectoparasite saliva protein of the present invention can be encoded by a full-length nucleic acid sequence which encodes a polyprotein. The polyprotein can be post-translationally processed into multiple proteins which are found in saliva. As used herein, an ectoparasite saliva protein gene includes all nucleic acid sequences related to a natural ectoparasite saliva protein gene such as regulatory regions that control production of an ectoparasite saliva protein encoded by that gene (such as, but not limited to, transcription, translation or post-translation control regions) as well as the coding region itself. A nucleic acid molecule of the present invention can be an isolated natural ectoparasite saliva protein nucleic acid molecule or a homologue thereof. A nucleic acid molecule of the present invention can include one or more regulatory regions, full-length or partial coding regions, or combinations thereof. The minimal size of an ectoparasite saliva protein nucleic acid molecule of the present invention is the minimal size capable of forming a stable hybrid under stringent hybridization conditions with a corresponding natural gene.

An ectoparasite saliva protein nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an allergic response in animals having allergic dermatitis or the ability of a homologue to act as an anti-coagulant) and/or by hybridization with isolated ectoparasite saliva protein nucleic acids under stringent conditions.

One embodiment of the present invention is an ectoparasite saliva protein nucleic acid molecule that encodes a protein having at least a portion of one or more of the following amino acid sequences: SEQ ID NO:1, as well as with the complements of any of these sequences or homologues thereof. Such preferred nucleic acid molecules can hybridize to the coding and/or complementary strand.

A preferred nucleic acid molecule of the present invention is capable of hybridizing under stringent conditions to the coding strand and/or to the strand complementary to the coding strand of a nucleic acid molecule that encodes at least a portion of such a flea saliva protein or homologue thereof. A particularly preferred nucleic acid sequence is a nucleic acid sequence having at least about 65 percent, preferably at least about 75 percent, more preferably at least about 85 percent, and even more preferably at least about 95 percent homology with a nucleic acid sequence encoding at least a portion of one or more of the following amino acid sequences:SEQ ID NO:53, SEQ ID NO:62, SEQ ID NO:65, SEQ ID NO:70, SEQ ID NO:72, SEQ ID NO:75, SEQ ID NO:77, SEQ ID NO:78 and/or SEQ ID NO:87.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:71, SEQ ID NO:73, SEQ ID NO:74, SEQ ID NO:76, a nucleic acid sequence encoding amino acid sequence SEQ ID NO:78 or SEQ ID NO:87, or other sequences disclosed herein.

SEQ ID NO:52, a nucleic acid sequence that includes about 595 nucleotides of the apparent gene encoding flea saliva protein fspG5 (denoted $nfspG5_{595}$), encodes a protein of about 90 amino acids (denoted as $PfspG5_{90}$), represented by SEQ ID NO:53. The entire translation product of fspG5 is apparently about 71 amino acids and is denoted SEQ ID NO:56. SEQ ID NO:61, a nucleic acid sequence that includes about 1007 nucleotides of the apparent gene encoding flea saliva protein fspI (denoted $nfspI_{1007}$), encodes a protein of about 155 amino acids (denoted $PfspI_{155}$), which is denoted SEQ ID NO:62. SEQ ID NO:64, a nucleic acid sequence that includes about 1205 nucleotides of the apparent gene encoding flea saliva protein fspN5 (denoted $nfspN5_{1205}$), encodes a protein of about 353 amino acids (denoted $PfspN5_{353}$), which is denoted SEQ ID NO:65. SEQ ID NO:71, a nucleic acid sequence that includes about 406 nucleotides of the apparent gene encoding a fspN6 flea saliva protein (denoted $nfspN6_{406}$), encodes a protein of about 135 amino acids (denoted $PfspN6_{135}$), which is denoted SEQ ID NO:72. SEQ ID NO:74, a nucleic acid sequence that includes about 420 nucleotides of the apparent gene encoding a fspJ flea saliva protein, encodes a protein of about 72 amino acids, which is denoted SEQ ID NO:75.

Knowing a nucleic acid molecule of an ectoparasite saliva protein of the present invention allows one skilled in the art to make copies of that nucleic acid molecule as well as to obtain a nucleic acid molecule including additional portions of ectoparasite saliva protein-encoding genes (e.g., nucleic acid molecules that include the translation start site and/or transcription and/or translation control regions), and/or ectoparasite saliva protein nucleic acid molecule homologues. Knowing a portion of an amino acid sequence of an ectoparasite saliva protein of the present invention allows one skilled in the art to clone nucleic acid sequences encoding such an ectoparasite saliva protein. In addition, a desired ectoparasite saliva protein nucleic acid molecule can be obtained in a variety of ways including screening appropriate expression libraries with antibodies which bind to ectoparasite saliva proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea saliva protein nucleic acid molecules, preferred cDNA libraries include cDNA libraries made from unfed whole flea, fed whole flea, fed flea midgut, unfed flea midgut, and flea salivary gland. Techniques to clone and amplify genes are disclosed, for example, in Sambrook et al., ibid. The Examples section includes examples of the isolation of cDNA sequences encoding flea saliva proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of one or more of the following amino acid sequences: SEQ ID NO:53, SEQ ID NO:62, SEQ ID NO:65, SEQ ID NO:70, SEQ ID NO:72, SEQ ID NO:75, SEQ ID NO:77, SEQ ID NO:78, SEQ ID NO:87, or homologues thereof, such oligonucleotides can hybridize to the coding or non-coding strand of a double-stranded nucleic acid molecule. Certain preferred oligonucleotides are capable of hybridizing to nucleic acid molecules including nucleic acid sequences represented by SEQ ID NO:52, SEQ ID NO:58, SEQ ID NO:61, SEQ ID NO:64, SEQ ID NO:71, SEQ ID NO:74, a nucleic acid sequence that encodes SEQ ID NO:78 or SEQ ID NO:87, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of saliva proteins by ectoparasites. Such therapeutic applications include the use of such oligonucleotides in, for example, antisense-, triplex formation-, ribozyme- and/or RNA drug-based technologies. The present invention, therefore, includes such oligonucleotides and methods to interfere with the production of ectoparasite saliva proteins by use of one or more of such technologies.

The present invention also includes a recombinant vector, which includes an ectoparasite saliva protein nucleic acid molecule of the present invention inserted into any vector capable of delivering the nucleic acid molecule into a host cell. Such a vector contains heterologous nucleic acid sequences, that is nucleic acid sequences that are not naturally found adjacent to ectoparasite saliva protein nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of ectoparasite saliva protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that encodes at least a portion of one or more of the following amino acid sequences: SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87, or other sequences disclosed herein, or homologues thereof, and nucleic acid molecules including at least a portion of a nucleic acid sequence represented by SEQ ID NO:52, SEQ ID NO:58, SEQ ID NO:61, SEQ ID NO:64, SEQ ID NO:71, SEQ ID NO:74, a nucleic acid sequence that encodes SEQ ID NO:78 or SEQ ID NO:87, or other sequences disclosed herein, or complements thereof. A more preferred sequences to include in a recombinant vector include $nfspG5_{595}$, nfspG5 $_{270}$ $nfspG5_{213}$, $nfspI_{1007}$, $nfspN5_{1205}$, nfspN5 $_{1059}$ nfspN6 $_{406}$ and $nfspJ_{420}$.

Preferred recombinant molecules of the present invention include pCro-$nfspG5_{213}$ and pCro-$nfspI_{474}$, the production of which are described in detail in the Examples section.

In one embodiment, an isolated ectoparasite saliva protein of the present invention is produced by culturing a cell capable of expressing the protein under conditions effective to produce the protein, and recovering the protein. A preferred cell to culture is a recombinant cell that is capable of expressing the ectoparasite saliva protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell include one or more nucleic acid molecules that are as disclosed herein for including in recombinant vectors of the present invention.

Suitable host cells to transform include any cell that can be transformed and that can express the introduced ectoparasite saliva protein. Such cells are, therefore, capable of producing ectoparasite saliva proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda (λ) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an ectoparasite saliva protein.

Expression vectors of the present invention may also contain secretory signals (i.e., signal segment nucleic acid sequences) to enable an expressed ectoparasite saliva protein to be secreted from the cell that produces the protein. Suitable signal segments include an ectoparasite saliva protein signal segment or any heterologous signal segment capable of directing the secretion of an ectoparasite saliva protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of an ectoparasite nucleic acid molecule of the present invention can enhance the stability during production, storage and/or use of the protein encoded by the nucleic acid molecule. Furthermore, a fusion segment can function as a tool to simplify purification of an ectoparasite saliva protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an ectoparasite saliva protein. Linkages between fusion segments and ectoparasite saliva proteins can be constructed to be susceptible to cleavage to enable straight-forward recovery of the ectoparasite saliva proteins. Fusion proteins are preferably produced by culturing a recombinant cell transformed with a fusion nucleic acid sequence that encodes a protein including the fusion segment attached to either the carboxyl and/or amino terminal end of an ectoparasite saliva protein.

A recombinant molecule of the present invention is a molecule that can include at least one of any nucleic acid molecule heretofore described operatively linked to at least one of any transcription control sequence capable of effectalveoli regulating expression of the nucleic acid molecule (s) in the cell to be transformed. A preferred recombinant molecule includes one or more nucleic acid molecules that are as disclosed herein for including in a recombinant vector of the present invention.

A recombinant cell of the present invention includes any cells transformed with at least one of any nucleic acid molecules of the present invention. A preferred recombinant cell is a cell transformed with at least one nucleic acid molecule that encode a protein having at least a portion of one or more of the following amino acid sequences: SEQ ID NO:53, SEQ ID NO:62, SEQ ID NO:65, SEQ ID NO:70, SEQ ID NO:72, SEQ ID NO:75, SEQ ID NO:77, SEQ ID NO:78, SEQ ID NO:87, or other sequences disclosed herein, or homologues thereof, and nucleic acid molecules including at least a portion of a nucleic acid sequence represented by SEQ ID NO:52, SEQ ID NO:58, SEQ ID NO:61, SEQ ID NO:64, SEQ ID NO:71, SEQ ID NO:74, a nucleic acid sequence that encodes SEQ ID NO:78 or SEQ ID NO:87, or other sequences disclosed herein, or complements thereof. Particularly preferred recombinant cells include *E. coli* transformed with at least one of the aforementioned nucleic acid molecules. Preferred recombinant cells of the present invention include *E. coli*:pCro-nfspG$5_{213}$ and *E. coli*:pCro-nfspI$_{474}$.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an ectoparasite saliva protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an ectoparasite saliva protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant ectoparasite saliva proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Ectoparasite saliva proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Ectoparasite saliva proteins are preferably retrieved in "substantially pure" form. As used herein, "substantially pure" refers to a purity that allows for the effective use of the protein as a therapeutic composition or diagnostic. For example, an animal being administered dosages of ectoparasite saliva protein isolated from a recombinant cell of the present invention should exhibit no substantial toxicity from contaminants mixed with the protein.

Ectoparasite saliva that is substantially free of contaminating material can be collected using a saliva collection apparatus of the present invention (disclosed in related PCT Patent Publication No. WO 96/11,271, published Apr. 18, 1996, by Frank et al.; this publication is incorporated by reference herein in its entirety). The interior diameter of a preferred chamber of the present invention is preferably about 7.5 cm. The size of a collection means of the present invention is preferably larger than the open end of the 7.5 cm chamber, the size of the collection means is more preferably about 8 cm.

According to the present invention, ectoparasite saliva products can be extracted from a collection means (described in related PCT Patent Publication No. WO 96/11,271) by contacting a collection means with a Tris buffer containing sodium chloride, alcohol and Tris. A more preferred extraction buffer includes 2.5 M NaCl, 5% IPA and 20 mM Tris, about pH 8.0 to about pH 8.3. Suitable extraction times for eluting proteins and other products from the collection means using the Tris buffer are described in detail in the Examples.

Further concentration of saliva proteins extracted from a collection means of the present invention can be performed by concentrating the extracted flea saliva product-containing solution using hydrophobic interaction chromatographic (HIC) resins. Suitable HIC resins include any resins that bind protein at high salt concentrations. Preferred HIC resins include, for example, butyl-, octyl- and phenyl-substrate conjugated resins. A more preferred resin includes a phenyl-sepharose resin. In a preferred embodiment, extracted flea saliva proteins contained in a Tris buffer of the present invention can be contacted with a HIC resin to bind the flea saliva proteins to the resin.

In accordance with the present invention, a "mimetope" refers to any compound that is able to mimic the ability of an isolated ectoparasite saliva protein of the present invention to carry out its function (e.g., anti-coagulation, anti-complement, vasodialators, proteases, acid phosphatases or detecting and/or treating the hypersensitivity of an animal susceptible to or having allergic dermatitis). A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Mimetopes of the present invention can also include non-proteinaceous portions of ectoparasite saliva products having allergenic and/or antigenic activity (e.g., carbohydrate moieties associated with ectoparasite saliva proteins). A mimetope can be obtained by, for example, screening libraries of synthetic compounds for compounds capable of altering the ability of ectoparasites to feed, or of detecting and/or treating allergic dermatitis resulting from the bites of ectoparasites. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source (e.g., plants, animals, bacteria and fungi).

One embodiment of the present invention is an in vivo test that is capable of detecting whether an animal is hypersensitive to ectoparasite saliva products. An in vivo test of the present invention can initially be used to determine if an animal is hypersensitive to ectoparasite saliva products and then used to determine if an animal is hypersensitive to a particular ectoparasite saliva component, in particular to an ectoparasite saliva protein. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing at least one ectoparasite saliva product, or a mimetope thereof. Methods to conduct skin tests of the present invention are known to those of skill in the art and are briefly disclosed herein.

Suitable formulations to use in an in vivo skin test include one or more isolated ectoparasite saliva proteins of the present invention.

A suitable amount of ectoparasite saliva protein for use in a skin test of the present invention can vary widely depending on the allergenicity of the product used in the test and on the site at which the product is delivered. Suitable amounts of ectoparasite saliva proteins for use in a skin test of the present invention include an amount capable of forming reaction, such as a detectable wheal or induration (hardness) resulting from an allergic reaction to the product. Preferred amounts of ectoparasite saliva proteins for use in a skin test of the present invention range from about 1 nanogram (ng) to about 500 micrograms (μg), more preferably from about 5 ng to about 300 μg, and even more preferably from about 10 ng to about 50 μg of ectoparasite saliva proteins. It is to be appreciated by those of skill in the art that such amounts will vary depending upon the allergenicity of the protein(s) being administered.

According to the present invention, ectoparasite saliva proteins of the present invention can be combined with an immunopotentiator (e.g., carriers or adjuvants of the present invention as defined in detail below). A novel aspect, however, of the present invention is that an ectoparasite saliva protein of the present invention can induce a hypersensitive response in the absence of an immunopotentiator.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes at least one flea saliva protein of the present invention, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. One preferred formulation comprises flea saliva products collected in accordance with the present invention. Also preferred are formulations comprising one or more recombinantly produced flea saliva proteins.

Suitable flea saliva proteins for use with a skin test of the present invention include proteins having an amino acid sequence such as is listed in the Sequence Listing herein, or homologues thereof. A preferred positive control sample can be a sample comprising histamine. A preferred negative control sample can be a sample comprising diluent.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to one or more ectoparasite saliva proteins of the present invention by contacting a putative antibody-containing solution with a solution containing ectoparasite saliva proteins in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite saliva antigen.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of immunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of one or more ectoparasite saliva proteins of the present invention or a mimetope thereof, and of coating one or more other portions of the (or another) solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred flea saliva proteins for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate. In a preferred embodiment in which IgE antibodies in the body fluid are to be measured, the body fluid can be pretreated to remove at least some of the other isotypes of immunoglobulin and/or other proteins, such as albumin, present in the fluid. Such removal can include, but is not limited to, contacting the body fluid with a material, such a Protein G, to remove IgG antibodies and/or affinity purifying the IgE antibodies from other components of the body fluid by exposing the fluid to, for example, Concanavalin A (Con-A).

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies and Fc receptors (FcR) that bind to IgE antibodies (i.e., epsilon FcR), including single chains of an FcR (e.g., the alpha chain of an epsilon FcR), as well as truncated forms with or without transmembrane domains. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

A preferred embodiment of an in vitro hypersensitivity test of the present invention comprises the steps of: (a) contacting an ELISA plate, which is coated with a suitable amount of flea saliva extract (disclosed in related PCT Patent Publication No. WO 96/11,271, published Apr. 18, 1996, by Frank et al.; this publication is incorporated by reference herein in its entirety), including FS-1, FS-2, FS-3 and/or one or more flea saliva proteins (disclosed in related PCT Patent Publication No. WO 96/11,271 and disclosed herein), with serum, plasma or whole blood from an animal being tested for susceptibility to allergic dermatitis; and (b) identifying whether immunocomplexes are formed by step (a) by assaying for the presence of such immunocomplexes by (i) contacting the plate with an antibody that specifically binds to IgE or other compounds capable of binding to such immunocomplexes, such as an epsilon Fc receptor, and (ii) determining whether such an antibody or other compound is bound thereto. It should be noted that citing of specific embodiments does not preclude the use of a variety of other immunoassay protocols, including those in which a compound that binds IgE is coated onto a substrate; the substrate is then contacted with serum, plasma or whole blood; and binding of IgE by the compound is detected by the ability to bind flea saliva extracts or proteins of the present invention.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labeled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one prepacked syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite saliva allergen can be tested using an in vitro immunoabsorbent test capable of detecting IgE antibodies specific for an ectoparasite saliva allergen in the animal's bodily fluid. While most animals that display delayed hypersensitivity to an ectoparasite saliva allergen also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to an ectoparasite saliva allergen can be tested using an in vivo test of the present invention.

Another aspect of the present invention includes treating animals susceptible to or having allergic dermatitis, with a formulation of the present invention. According to the present invention, the term treatment can refer to the regulation of a hypersensitive response by an animal to bites from ectoparasites. Regulation can include, for example, immunomodulation of cells involved in the animal's hypersensitive response or alteration of the ability of an ectoparasite to introduce allergens into an animal, for example by inhibiting the anti-coagulation activity of a saliva enzyme, thereby impairing the ability of the arthropod to penetrate the dermis of an animal and feed. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response. Suitable and preferred ectoparasites against which to treat an animal are disclosed herein. A particularly preferred formulation of the present invention is used to treat FAD.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to ectoparasite saliva products and animals susceptible to hypersensitive responses against ectoparasite saliva products.

One embodiment of the present invention is a therapeutic composition that includes de-sensitizing compounds capable of inhibiting an immune response to an ectoparasite saliva protein of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A de-sensitizing compound of the present invention can be soluble or membrane-bound. Membrane-bound de-sensitizing compounds can be associated with biomembranes, including cells, liposomes, planar membranes, cochleates or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a de-sensitizing compound include, for example, at least a portion of an immunoglobulin molecule, cytokines, lectins, heterologous allergens, CD8 molecules, CD4 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the β chain of CD8. Preferred CD4 molecules include at least the extracellular functional domains of CD4. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

Suitable therapeutic compositions of the present invention for treating flea allergy dermatitis include flea saliva extracts (such as those disclosed in related PCT Patent Publication No. WO 96/11,271) and other formulations including at least one flea saliva protein, or a mimetope thereof. Preferred therapeutic compositions include FS-1, FS-2 and/or FS-3 (such as those disclosed in related PCT Patent Publication No. WO 96/11,271) as well as at least a portion of at least one flea saliva protein that can be isolated from FS-1, FS-2 and/or FS-3. As such, preferred formulations for use as therapeutic compositions include FS-1, FS-2, FS-3, and/or at least a portion of one or more of the proteins having an amino acid sequence including SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87.

In another embodiment, a therapeutic composition can include ectoparasite products of the present invention associated with a suitable excipient. A therapeutic composition of the present invention can be formulated in an excipient that the animal to be treated can tolerate. Preferred excipients are capable of maintaining a product of the present invention in a form that is capable of being bound by cells involved in an allergic response in an animal such that the cells are stimulated to initiate or enhance an immune response. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition of the present invention can also comprise a carrier or adjuvant, although it is to be appreciated that an advantage of saliva products of the present invention is that adjuvants and/or carriers are not required for administration. Adjuvants are typically substances that generally enhance the immune response of an animal to a specific antigen. Suitable adjuvants include, but are not limited to, cytokines, chemokines, and compounds that induce the production of cytokines and chemokines (e.g., granulocyte macrophage colony stimulating factor [GM-CSF], macrophage colony stimulating factor [M-CSF], granulocyte colony stimulating factor [G-CSF], colony stimulating factor [CSF], erythropoietin [EPO], interleukin-2 [IL-2], interleukin-3 [IL-3], interleukin-5 [IL-5], interleukin-6 [IL-6], interleukin-7 [IL-7], interleukin-8 [IL-8], interleukin-10 [IL-10], interleukin-12 [IL-12], gamma interferon [IFN-γ], interferon gamma inducing factor [IGIF], transforming growth factor beta, RANTES [regulated upon activation, normal T cell expressed and presumably secreted], macrophage inflammatory proteins [e.g., MIP1α and MIPL1β], and Leishmania elongation initiating factor [LeIF]; bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant [Vaxcel™, Inc. Norcross, Ga.], Ribi adjuvants [Ribi ImmunoChem Research, Inc., Hamilton, Mont.]; and saponins and their derivatives (e.g., Quil A [Superfos Biosector A/S, Denmark]. Protein adjuvants of the present invention can be delivered in the form of the protein themselves or of nucleic acid molecules encoding such proteins using the methods described herein.

Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a therapeutic composition of the present invention into the bloodstream of an animal. Suitable controlled release formulations include, but are not limited to, biocompatible (including biodegradable) polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ.

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser,. No. 08/015/414, filed Feb. 8, 1993, entitled "Recombinant Virus Particle Vaccines", U.S. Pat. No. 5,266,313, by Esposito et al., issued Nov. 30, 1993 and U.S. patent application Ser. No. 08/602,010, by Haanes et al., filed Jan. 15, 1996, entitled "Recombinant Canine Herpesvirus", each of the patents and patent application referred to in this section is incorporated by reference herein in its entirety.

When administered to an animal, a recombinant virus particle therapeutic composition of the present invention infects cells within the immunized animal and directs the production of a protective protein or RNA nucleic acid molecule that is capable of protecting the animal from allergic dermatitis caused by the bites of ectoparasites. For example, a recombinant virus particle comprising a nucleic acid molecule encoding one or more ectoparasite saliva protein of the present invention is administered according to a protocol that results in the tolerization of an animal against ectoparasite saliva allergens.

According to one embodiment, a nucleic acid molecule of the present invention can be delivered to an animal as a naked (i.e., not packaged in a viral coat or cellular membrane) nucleic acid vaccine (e.g., as naked DNA or RNA molecules, such as is taught, for example in Wolff et al., 1990*, Science* 247, 1465–1468). A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a dicistronic recombinant molecule. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. An example of one embodiment is disclosed in PCT Patent Publication No. WO 95/05853, published Mar. 2, 1995. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized, oral and/or topical. Naked DNA of the present invention can be contained in an aqueous excipient (e.g., phosphate buffered saline) alone or a carrier (e.g., lipid-based vehicles).

Therapeutic compositions of the present invention can be sterilized by conventional methods which do not result in protein degradation (e.g., filtration) and/or lyophilized.

A therapeutic composition of the present invention can be administered to any animal susceptible to ectoparasite infestation as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to ectoparasite saliva allergens. Effective doses can vary depending upon, for example, the therapeutic composition used, the arthropod from which the composition was derived, and the size and type of the recipient animal. Effective doses to immunomodulate an animal against ectoparasite saliva allergens include doses administered over time that are capable of alleviating a hypersensitive response by an animal to ectoparasite saliva allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to the bite of an ectoparasite. An effective dose to desensitize an animal can comprise a concentration of a therapeutic composition of the present invention sufficient to block an animal from having a hypersensitive response to the bite of an ectoparasite. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to ectoparasite saliva allergens when administered one or more times over a suitable time period. For example, a preferred single dose of an ectoparasite saliva product, or mimetope therapeutic composition is from about 0.5 ng to about 1 g of the therapeutic composition per kilogram body weight of the animal. Further treatments with the therapeutic composition can be administered from about 1 hour to 1 year after the original administration. Further treatments with the therapeutic composition preferably are administered when the animal is no longer protected from hypersensitive responses to ectoparasite. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to ectoparasite bites. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Another aspect of the present invention includes a method for prescribing treatment for animals susceptible to or having allergic dermatitis, using a formulation of the present invention. A preferred method for prescribing treatment for flea allergy dermatitis, for example, comprises: (1) intradermally injecting into an animal at one site an effective amount of a formulation containing at least one flea saliva antigen of the present invention, or a mimetope thereof (suitable and preferred formulations are disclosed herein); (2) intradermally injecting into the animal at a second site an effective amount of a control solution; (3) evaluating if the animal has flea allergy dermatitis by measuring and comparing the wheal size resulting from injection of the formulation with the wheal size resulting from injection of the control solution; and (4) prescribing a treatment for the flea allergy dermatitis.

An alternative preferred method for prescribing treatment for flea allergy dermatitis comprises: (1) contacting a first portion of a sample of bodily fluid obtained from an animal to be tested with an effective amount of a formulation containing at least one flea saliva antigen, or a mimetope thereof (suitable and preferred formulations are disclosed herein) to form a first immunocomplex solution; (2) contacting a positive control antibody to form a second immunocomplex solution; (3) evaluating if the animal has flea allergy dermatitis by measuring and comparing the amount of immunocomplex formation in the first and second immunocomplex solutions; and (4) prescribing a treatment for the flea allergy dermatitis. It is to be noted that similar methods can be used to prescribe treatment for allergies caused by other ectoparasites using ectoparasite saliva product formulations as disclosed herein.

Another aspect of the present invention includes a method for monitoring animals susceptible to or having allergic dermatitis, using a formulation of the present invention. In vivo and in vitro tests of the present invention can be used to test animals for allergic dermatitis prior to and following any treatment for allergic dermatitis. A preferred method to monitor treatment of flea allergy dermatitis (which can also be adapted to monitor treatment of other ectoparasite allergies) comprises: (1) intradermally injecting an animal at one site with an effective amount of a formulation containing at least one flea saliva protein, or a mimetope thereof (suitable and preferred formulations are disclosed herein); (2) intradermally injecting an effective amount of a control solution into the animal at a second site; and (3) determining if the animal is desensitized to flea saliva antigens by measuring and comparing the wheal size resulting from injection of the formulation with the wheal size resulting from injection of the control solution.

An alternative preferred method to monitor treatment of flea allergy dermatitis (which can be adapted to monitor treatments of other ectoparasite allergies) comprises: (1) contacting a first portion of a sample of bodily fluid obtained from an animal to be tested with an effective amount of a formulation containing at least one flea saliva protein or mimetope thereof (suitable and preferred formulations are disclosed herein) to form a first immunocomplex solution; (2) contacting a positive control antibody to form a second immunocomplex solution; and (3) determining if the animal is desensitized to flea saliva antigens by measuring and comparing the amount of immunocomplex formation in the first and second immunocomplex solutions.

The present invention also includes antibodies capable of selectively binding to an ectoparasite saliva protein, or mimetope thereof. Such an antibody is herein referred to as an anti-ectoparasite saliva protein antibody. As used herein, the term "selectively binds to" refers to the ability of such an antibody to preferentially bind to ectoparasite saliva proteins and mimetopes thereof. In particular, the present invention includes antibodies capable of selectively binding to flea saliva proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferably, an antibody of the present invention has a single site binding affinity of from about $10^3\ M^{-1}$ to about $10^{12}\ M^{-1}$ for a flea saliva product of the present invention.

A preferred method to produce antibodies of the present invention includes administering to an animal an effective amount of an ectoparasite saliva protein or mimetope thereof to produce the antibody and recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from allergic dermatitis, (b) as positive controls in test kits, and/or (c) as tools to recover desired ectoparasite saliva proteins from a mixture of proteins and other contaminants.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., Borovsky, Arch. *Insect Biochem. and Phys.,* 7:187–210, 1988, and related references. Examples 1 through 16, and the SEQ ID NO's cited therein, of related PCT Publication WO 96/11,271, published Apr. 18, 1996, are incorporated herein by this reference in their entirety.

Example 1

This example describes the amino acid sequence analysis of additional isolated flea saliva proteins from FS-1 extract and eluted from DE-81 filters.

FS-1 flea saliva extract and flea saliva product eluted from DE-81 filters were collected using techniques described in Example 2 of related PCT Publication No. WO 96/11,271. Using standard purification techniques (e.g., C4 reverse phase chromatography; SDS-PAGE gel electrophoresis and blotting; and/or flow through electrophoresis), several proteins were isolated from peak M and partial amino acid sequences were determined as described in Example 4 of related PCT Publication No. WO 96/11,271. Partial N-terminal amino acid sequencing indicated that peak M contained fspJ, fspL and fspN proteins (as described in Example 4 of related PCT Publication No. WO 96/11,271) as well as newly identified proteins referred to herein as fspM(G), fspM(H), fspM(I), fspM(J), fspM(K), fspM(L) and fspM(M). Flea saliva protein fspM(G), having a molecular weight of about 37 kD, had an N-terminal partial amino acid sequence of M R G N H V F L E D G M A D M T G G Q Q M G R D L Y, denoted SEQ ID NO:1. Flea saliva protein fspM(H), having a molecular weight of about 34 kD, had an N-terminal partial amino acid sequence of K Y R N (Y/D) X T N D P Q Y, denoted SEQ ID NO:2. Flea saliva protein fspM(I), having a molecular weight of about 10 kD had an N-terminal partial amino acid sequence of E I K R N D R E P G N L S K I R T V M D K V I K Q T Q, denoted SEQ ID NO:3. Flea saliva protein fspM(J), having a molecular weight of about 25 kD, had an N-terminal partial amino acid sequence of L K D N D I Y (A/H) (A/H) R D I N E I L R V L D P S K, denoted SEQ ID NO:4. Flea saliva protein fspM(K), having a molecular weight of about 30 kD, had an N-terminal partial amino acid sequence of N Y G R V Q I E D Y T X S N H K D X E E K D Q I N G L, denoted SEQ ID NO:5. Flea saliva protein fspM(L), having a molecular weight of about 37 kD, had an N-terminal partial amino acid sequence of K Y R N X Y T N D P Q L K L L D E G, denoted SEQ ID NO:6. Flea saliva protein fspM(M) was recovered from peak M and subjected to amino acid sequence analysis as described in Example 4 of related PCT Publication No. WO 96/11,271. Flea saliva protein fsp(M), having a molecular weight of about 31 kD, had an N-terminal partial amino acid sequence of Y F N D Q I K S V M E P X V F K Y P X A X L, denoted SEQ ID NO:7. A Genbank homology search revealed no significant homology between known amino acid sequences and those determined for fspM(G), fspM(H), fspM(I), fspM(J), fspM (K), fspM(L) and fspM(M).

Example 2

This example describes the isolation of nucleic acid molecules encoding at least a portion of a fspG flea saliva protein. This example also describes expression of a fspG protein by bacteria.

A. Isolation of fspG4 Nucleic Acid Molecules

The partial N-terminal amino acid sequence of fspG2 (i.e., SEQ ID NO:29 of related PCT Publication No. WO 96/11, 271) was used to synthesize degenerate antisense Primer G2-2, having the nucleic acid sequence 5' TGR TTT CCW ATR AAR TCT TC 3', denoted SEQ ID NO:8. Primer G2-2 was used in combination with the M13 reverse primer (SEQ ID NO:40; described in Example 7 of related PCT Publication No. WO 96/11,271), to PCR amplify, using standard techniques, the 5'-terminal portion of the fspG4 gene from a salivary gland cDNA expression library as described above in Example 6A of related PCT Publication No. WO 96/11, 271. The resulting PCR product was approximately 225-bp when visualized on a 1% agarose gel. The nucleotide sequence of the 225-bp PCR fragment was obtained, named $nfspG4_{225}$ is presented as SEQ ID NO:9.

The nucleic acid sequence of $nfspG4_{225}$ was used to synthesize sense Primer G5, having nucleic acid sequence 5' AAT TCG GCA CGA GTG 3', denoted SEQ ID NO:10. Primer G5 was used in combination with the M13 universal primer (SEQ ID NO:19; described in Example 6 of related PCT Publication No. WO 96/11,271), to PCR amplify, as described above, the 3'-terminal portion of the fspG4 gene from the salivary gland cDNA expression library described above in Example 6A of related PCT Publication No. WO 96/11,271). The resulting PCR product, denoted nfspG4$_{610}$, was approximately 610-bp when visualized on a 1% agarose gel. The nucleotide sequence of the 610-bp PCR fragment was obtained, 565 nucleotides of which are presented as SEQ ID NO:11. The nucleic acid molecule containing nucleic acid sequence SEQ ID NO:11 is referred to herein as nfspG4$_{565}$. Translation of SEQ ID NO:11 suggests that nucleic acid molecule nfspG4$_{565}$ encodes a full-length fspG protein of about 90 amino acids, referred to herein as PfspG4$_{90}$, assuming an open reading frame having a start codon spanning from about nucleotide 45 through about nucleotide 47 of SEQ ID NO:11 and a stop codon spanning from about nucleotide 315 through about nucleotide 317 of SEQ ID NO:11. This open reading frame, excluding the stop codon, comprises nucleic acid molecule nfspG4$_{270}$ of the present invention, the nucleic acid sequence of which is represented herein by SEQ ID NO:13. PfspG4$_{90}$ is denoted herein as SEQ ID NO:12. Residues 20–42 of SEQ ID NO:12 appear to be identical to SEQ ID NO:29 of related PCT Publication No. WO 96/11,271 (N-terminal partial amino acid sequence of fspG2), except that residue 37 of SEQ ID NO:12 is a glutamic acid rather than a lysine. In addition, residues 38–57 of SEQ ID NO:12 appear to be identical to SEQ ID NO:30 of related PCT Publication No. WO 96/11, 271 (N-terminal partial amino acid sequence of fspG3). These similarities support the likelihood of a family of fspG proteins in flea saliva.

Analysis of SEQ ID NO:11 suggests that the sequence includes a leader segment of about 19 amino acids followed by a mature protein. The leader sequence is apparently cleaved to form a mature protein termed PfspG4$_{71}$, denoted SEQ ID NO:12. PfspG4$_{71}$ has a calculated molecular weight of 7536 daltons and calculated pI of about 9.0. PfspG4$_{90}$ has a calculated molecular weight of 9657 daltons and calculated pI of about 9.26. A Genbank homology search revealed no significant homology between SEQ ID NO:11 or SEQ ID NO:12 and known nucleic acid sequences or known amino acid sequences, respectively.

B. Expression

An about 216-bp DNA fragment of nfspG4 was PCR amplified from nucleic acid molecule nfspG4, using: Primer G7, a sense primer having the nucleic acid sequence 5' AGT GGA TCC GTC AAA AAT GGT CAC TG 3', denoted as (SEQ ID NO:15 (BamHI site in bold); and Primer G8, an antisense primer having the nucleic acid sequence 5' CCG GAA TTC GGT TAT TCG CAA TAA CAG T 3' (EcoRI site in bold), denoted SEQ ID NO:16. The PCR product, a fragment of about 216 nucleotides, denoted nfspG4$_{216}$, was digested with BamHI and EcoRI restriction endonucleases, gel purified, and subcloned into expression vector $P_R/T^2$ori/S10HIS-RSET-A9 (described in Example 16 of related PCT Publication No. WO 96/11,271) that had been digested with BamHI and EcoRI to produce recombinant molecule pHis-nfspG4$_{216}$.

The recombinant molecule was transformed into *E. coli* to form recombinant cell *E. coli*:pHis-nfspG4$_{216}$. The recombinant cell was cultured and induced as described in Example 11A of related PCT Publication No. WO 96/11,271 to produce fusion protein PHIS-fspG4$_{72}$. The recombinant fusion protein was detected by immunoblot analysis using the T7 Tag monoclonal antibody as described in Example 11A of related PCT Publication No. WO 96/11,271.

Example 3

This example describes the isolation of nucleic acid sequences encoding at least a portion of flea saliva proteins fspM(A), fspM(B), fspM(C), fspM(D), fspM(E), and fspM (F).

A. nfspM(A)$_{897}$ and nfspM(B)$_{2706}$

A flea salivary gland cDNA library (prepared as described in Example 6 of related PCT Publication No. WO 96/11,271) was immunoscreened with antiserum collected from a rabbit that was immunized with the proteins in peak M2 of the HPLC separation of flea saliva extract described in Example 3 of related PCT Publication No. WO 96/11,271 (i.e., fspM2 proteins). Immunoscreening was performed as described in Example 12 of related PCT Publication No. WO 96/11,271.

A nucleotide sequence for a nfspM nucleic acid molecule named nfspM(A)$_{897}$ is denoted as SEQ ID NO:17. Translation of SEQ ID NO:17 suggests that nucleic acid molecule nfspM(A)$_{897}$ encodes a full-length fspM protein of about 157 amino acids, referred to herein as PfspM(A)$_{157}$, assuming an open reading frame having a start codon spanning from about nucleotide 97 through about nucleotide 99 of SEQ ID NO:17 and a stop codon spanning from about nucleotide 568 through about nucleotide 570 of SEQ ID NO:17. This open reading frame, excluding the stop codon, comprises nucleic acid molecule nfspM(A)$_{471}$ of the present invention, the nucleic acid sequence of which is represented herein by SEQ ID NO:19. The amino acid sequence of PfspM(A)$_{157}$ is denoted SEQ ID NO:18. PfspM(A)$_{157}$ has a calculated molecular weight of about 18,291.68 daltons and calculated pI of about 10.3. A Genbank homology search revealed no significant homology between SEQ ID NO:17 or SEQ ID NO:18 and known nucleic acid or amino acid sequences, respectively.

A nucleotide sequence for another nfspM nucleic acid molecule named nfspM(B)$_{2706}$ is denoted as SEQ ID NO:20. Translation of SEQ ID NO:20 suggests that nucleic acid molecule nfspM(B)$_{2706}$ encodes a non-full-length fspM protein of about 900 amino acids, referred to herein as PfspM(B)$_{900}$, assuming an open reading frame having a start codon spanning from about nucleotide 5 through about nucleotide 7 of SEQ ID NO:20. The amino acid sequence of PfspM(B)$_{900}$ is denoted SEQ ID NO:21. PfspM(B)$_{900}$ has a calculated molecular weight of about 104,647 daltons and calculated pI of about 5.8.

The nucleic acid and amino acid sequences of the nfspM (B)$_{2706}$ nucleic acid molecule and PfspM(B)$_{900}$ protein, respectively, were compared to known nucleic acid and amino acid sequences using a Genbank homology search. SEQ ID NO:21 was found to be similar to the amino acid sequence of RhoA-binding alpha kinase (ROK). The most highly conserved region of continuous similarity between SEQ ID NO:21 and ROK amino acid sequences spans from about amino acid 32 through about amino acid 351 of SEQ ID NO:21 and from about amino acid 1 through about amino acid 900 of the ROK, there being about 75% identity between the two regions. Comparison of the nucleic acid sequence encoding amino acids from about 326 through about 1285 of the ROK kinase with the corresponding regions, spanning nucleotides from about 98 through about 1075 of nfspM(B)$_{2706}$ indicate that those regions are about 71% identical.

B. nfspM(C)$_{414}$ and nfspM(D)$_{273}$

A flea salivary gland cDNA library (prepared as described in Example 6 of related PCT Publication No. WO 96/11,271) was immunoscreened with antiserum collected from a rabbit that was immunized with the proteins in peak M1 of the HPLC separation of flea saliva extract described in Example 3 of related PCT Publication No. WO 96/11,271 (i.e., fspM1 proteins). Immunoscreening was performed as described in Example 12 of related PCT Publication No. WO 96/11,271.

Nucleotide sequence for a nfspM nucleic acid molecule named nfspM(C)$_{414}$ is denoted as SEQ ID NO:22. Translation of SEQ ID NO:22 suggests that nucleic acid molecule nfspM(C)$_{414}$ encodes a non-full-length fspM protein of about 137 amino acids, referred to herein as PfspM(C)$_{137}$, assuming the first residue spans from about nucleotide 2 through about nucleotide 4 of SEQ ID NO:22. The amino acid sequence of PfspM(C)$_{137}$ is denoted SEQ ID NO:23. PfspM(C)$_{137}$ has a calculated molecular weight of about 14,452 daltons and calculated pI of about 2.81. A Genbank homology search revealed no significant homology between SEQ ID NO:22 or SEQ ID NO:23 and known nucleic acid sequences or known amino acid sequences, respectively.

A nucleotide sequence for another nfspM nucleic acid molecule named nfspM(D)$_{273}$ is denoted as SEQ ID NO:24. Translation of SEQ ID NO:24 suggests that nucleic acid molecule nfspM(D)$_{273}$ encodes a non-full-length fspM protein of about 90 amino acids, referred to herein as PfspM (D)$_{90}$, assuming the first residue spans from about nucleotide 3 through about nucleotide 5 of SEQ ID NO:24. The amino acid sequence of PfspM(D)$_{90}$ is denoted SEQ ID NO:25. PfspM(D)$_{90}$ has a calculated molecular weight of about 9,503 daltons and calculated pI of about 3.01. SEQ ID NO:24 and SEQ ID NO:25 appear to be substantially similar to SEQ ID NO:22 and SEQ ID NO:23, respectively, suggesting a family of fspM proteins in flea saliva.

C. nfspM(E)$_{1704}$ and nfspM(F)$_{1758}$

A flea salivary gland cDNA library (prepared as described in Example 6 as described of related PCT Publication No. WO 96/11,271) was immunoscreened with antiserum collected from a rabbit that was immunized with the proteins in peak M2 of the HPLC separation of flea saliva extract described in Example 3 of related PCT Publication No. WO 96/11,271 (i.e., fspM2 proteins). Immunoscreening was performed as described in Example 12 of related PCT Publication No. WO 96/11,271.

A nucleotide sequence for another nfspM nucleic acid molecule named nfspM(E)$_{1704}$ is denoted as SEQ ID NO:26. Translation of SEQ ID NO:26 suggests that nucleic acid molecule nfspM(E)$_{1704}$ encodes a full-length fspM protein of about 461 amino acids, referred to herein as PfspM(E)$_{461}$, assuming the first residue spans from about nucleotide 24 through about nucleotide 26 of SEQ ID NO:26 and a stop codon spanning from about nucleotide 1407 through about nucleotide 1409 of SEQ ID NO:26. This open reading frame, excluding the stop codon, comprises nucleic acid molecule nfspM(E)$_{1383}$ of the present invention, the nucleic acid sequence of which is represented herein by SEQ ID NO:28. The amino acid sequence of PfspM(E)$_{461}$ is denoted SEQ ID NO:27. PfspM(E)$_{461}$ has a calculated molecular weight of about 54,139 daltons and calculated pI of about 7.00. A Genbank homology search revealed no significant homology between SEQ ID NO:26 or SEQ ID NO:27 and known nucleic acid sequences or known amino acid sequences, respectively.

A nucleotide sequence for another nfspM nucleic acid molecule named nfspM(F)$_{1758}$. is denoted as SEQ ID NO:29. Translation of SEQ ID NO:29 suggests that nucleic acid molecule nfspM(F)$_{1758}$ encodes a non-full-length fspM protein of about 586 amino acids, referred to herein as PfspM(F)$_{586}$, assuming an open reading frame having a start codon spanning from about nucleotide 1 through about nucleotide 3 of SEQ ID NO:29. The amino acid sequence of PfspM(F)$_{586}$. is denoted SEQ ID NO:30. PfspM(F)$_{586}$ has a calculated molecular weight of about 66,547 daltons and calculated pI of about 4.80. A Genbank homology search revealed no significant homology between SEQ ID NO:29 or SEQ ID NO:30 and known nucleic acid sequences or known amino acid sequences, respectively.

Example 4

This Example demonstrates the expression of a fspM protein in *E. Coli* cells.

Flea saliva protein PHIS-PfspM(D)$_{90}$, fusion protein was produced in the following manner. An about 305-bp DNA fragment, referred to herein as nfspM(D)$_{305}$, was isolated from nfspM(D)$_{293}$ (denoted SEQ ID NO:31) subcloned into pBluescript plasmid by digesting the nfspM(D)-containing plasmid with BamH1 and XhoI restriction endonucleases. The digestion product was gel purified and subcloned into expression vector pTrcHisB that had been digested with BamH1 and XhoI, and dephosphorylated. The resultant recombinant molecule, referred to herein as pHis-nfspM(D)$_{305}$, was transformed into *E. coli* HB101 competent cells (available from Gibco BRL, Gaithersburg, MD.) to form recombinant cell *E. coli*:pHis-nfspM(D)$_{305}$. The recombinant cell was cultured and expression of nfspM$_{305}$ induced using conditions described in Example 11A of related PCT Publication No. WO 96/11,271. Immunoblot analysis of recombinant cell *E. coli*:pHis-nfspM(D)$_{305}$ lysates using a T7 tag monoclonal antibody (Novagen, Inc) directed against the fusion portion of the recombinant PHis-nfspM(D)$_{305}$ fusion protein identified a protein of the appropriate size, namely an about 15,851 kD protein.

Example 5

This example describes the isolation of nucleic acid sequences encoding at least a portion of flea saliva proteins fspN(C), fspN(D), fspN(E), fspN(F), fspN(G), fspN(H), fspN(I), fspN(J), fspN(K), fspN(L), fspN(M), fspN(N) and fspN(O).

A. Preparation of IgE Enriched Antiserum

Serum was obtained from the artificially sensitized dog CQQ2 (described in Example 8 of related PCT Publication No. WO 96/11,271). About 10 ml of antiserum was incubated with protein G-Sepharose (5 ml) over night at 4° C.

B. Immunoscreening With IgE Enriched Antiserum

About 2.4 ml of *Escherichia coli* (XL1 Blue, O.D.$_{600}$= 0.5) was incubated with 6.48×$10^5$ pfu of phage from a flea salivary gland ZAP-cDNA library (1.8×$10^7$ pfu/ml), at 37° C. for 15 min and plated in 12 Luria-Bertani (LB) medium agar plates (150 mm). The plates were incubated at 37° C. over night. Each plate was then overlaid with an IPTG (10 mM) treated nitrocellulose filters for about 4 hours at 37° C. The filters were then removed and washed with TBST (20 mM Tris-HCl pH 7.5, 150 mM NaCl, 0.05% Tween-20). The filters were blocked with 5% dry milk in TBST for 2 hours at room temperature. Different filters were then incubated first with either IgE enriched CQQ2 antiserum or antiserum obtained from dogs infected with *Dirofilaria immitis*) at 4° C., overnight, then with a monoclonal anti-canine IgE antibody (D-9; gift from the laboratory of Dr. D. J. DeBoer, School of Veterinary Medicine, University of Wisconsin, Madison, Wis.), and then with a donkey anti-mouse IgG antibody conjugated to horseradish peroxidase (available from Jackson ImmunoResearch, West Grove, Pa.) for 2 hours at room temperature at each step. All of the filters were washed with TBST (3×15 min/wash) between each incubation. All of the filters were then treated to a final wash in TBS. Immunocomplexed plaques were identified by immersing the filters into the developing solution (TMB Peroxidase Substrate/TMB Peroxidase Solution/TMB Membrane Enhancer from Kirkegaard & Perry Laboratories) at 1/1/0.1 volume ratio to produce a color reaction. Eighteen plaques were identified and further plaque purified under the same immunoscreening condition as described above.

C. $nfspN(C)_{335}$, $nfspN(D)_{390}$ $nfspN(E)_{285}$ $nfspN(F)_{228}$ $nfspN(G)_{339}$, $nfspN(G)_{493}$, Single plaque of purified clones were isolated and stored in SM phage buffer (50 mM Tris, pH 7.4, 0.58% NaCl, 0.2% $MgCl_2.7H_2O$ and 0.01% Gelatin). The in vivo excision of the pBluescript phagemid from each positive clone was prepared by using ExAssis™/SOLR™ system (Stratagene). The pBluescript plasmid was purified by plasmid midi kit (Qiagen), and denatured with NaOH (0.4 N) at 37° C. for 15 min. The denatured plasmid was precipitated by ethanol and nucleic acid sequence obtained.

A nucleotide sequence for a nfspN nucleic acid molecule named $nfspN(C)_{335}$ is denoted as SEQ ID NO:32. A Genbank homology search revealed some similarity between SEQ ID NO:32 and ribosomal protein S6.

A nucleotide sequence for another nfspN nucleic acid molecule named $nfspN(D)_{396}$ is denoted as SEQ ID NO:33. A Genbank homology search revealed some similarity between SEQ ID NO:33 and erythropoietin.

A nucleotide sequence for another nfspN nucleic acid molecule named $nfspN(E)_{285}$ is denoted as SEQ ID NO:34. A Genbank homology search revealed some similarity between SEQ ID NO:34 and glutamic acid-rich protein or heat-shock protein, HSP81.

A nucleotide sequence for another nfspN nucleic acid molecule named $nfspN(F)_{228}$ is denoted as SEQ ID NO:35.

Nucleic acid sequence for portions of another nfspN nucleic acid molecule, denoted herein as nfspN(G), were obtained. The nucleic acid molecule representing a 5' portion of nfspN(G) named $nfspN(G)_{339}$ is denoted as SEQ ID NO:36. Translation of SEQ ID NO:36 suggests that nucleic acid molecule $nfspN(G)_{339}$ encodes a non-full-length fspN (G) protein of about 113 amino acids, referred to herein as $PfspN(G)_{113}$, assuming the first residue spans from about nucleotide 1 through about nucleotide 3 of SEQ ID NO:36. The amino acid sequence of $PfspN(G)_{113}$ is denoted SEQ ID NO:37.

The nucleic acid molecule representing a 3' portion of nfspN(G) named $nfspN(G)_{493}$ is denoted as SEQ ID NO:38. Translation of SEQ ID NO:38 suggests that nucleic acid molecule $nfspN(G)_{493}$ encodes a non-full-length fspN(G) protein of about 130 amino acids, referred to herein as $PfspN(G)_{130}$, assuming the first residue spans from about nucleotide 1 through about nucleotide 3 of SEQ ID NO:38 and a stop codon spanning from about nucleotide 391 through about nucleotide 393 of SEQ ID NO:38. The amino acid sequence of $PfspN(G)_{130}$ is denoted SEQ ID NO:39. A Genbank homology search revealed some similarity between SEQ ID NO:36 and SEQ ID NO:38 and vitellogenin.

A nucleotide sequence for another nfspN nucleic acid molecule named $nfspN(H)_{306}$ is denoted as SEQ ID NO:40.

A nucleotide sequence for another nfspN nucleic acid molecule named $nfspN(I)_{490}$ is denoted as SEQ ID NO:41.

A nucleotide sequence for another nfspN nucleic acid molecule named $nfspN(J)_{616}$ is denoted as SEQ ID NO:42.

A nucleotide sequence for another nfspN nucleic acid molecule named $nfspN(K)_{475}$is denoted as SEQ ID NO:43.

A nucleotide sequence for another nfspN nucleic acid molecule named $nfspN(L)_{295}$is denoted as SEQ ID NO:44.

A nucleotide sequence for another nfspN nucleic acid molecule named nfspN $(M)_{372}$ is denoted as SEQ ID NO:45.

Nucleic acid sequence for portions of another nfspN nucleic acid molecule, denoted herein as nfspN(N), were obtained. The nucleic acid molecule representing a 5' portion of nfspN(N) named $nfspN(N)_{252}$ is denoted as SEQ ID NO:46. The nucleic acid molecule representing a 3' portion of nfspN(N) named $nfspN(N)_{613}$ is denoted as SEQ ID NO:47.

Nucleic acid sequence for portions of another nfspN nucleic acid molecule, denoted herein as nfspN(O), were obtained. The nucleic acid molecule representing a 5' portion of nfspN(O) named $nfspN(O)_{538}$ is denoted as SEQ ID NO:48. Translation of SEQ ID NO:48 suggests that nucleic acid molecule $nfspN(O)_{538}$ encodes a non-full-length fspN (O) protein of about 178 amino acids, referred to herein as $PfspN(O)_{178}$, assuming the first residue spans from about nucleotide 1 through about nucleotide 3 of SEQ ID NO:48. The amino acid sequence of $PfspN(N)_{178}$ is denoted SEQ ID NO:49.

The nucleic acid molecule representing a 3' portion of nfspN(O) named $nfspN(O)_{432}$ is denoted as SEQ ID NO:50. Translation of SEQ ID NO:50 suggests that nucleic acid molecule $nfspN(O)_{432}$ encodes a non-full-length fspN(O) protein of about 129 amino acids, referred to herein as $PfspN(O)_{129}$, assuming the first residue spans from about nucleotide 1 through about nucleotide 3 of SEQ ID NO:50 and a stop codon spanning from about nucleotide 388 through about nucleotide 390 of SEQ ID NO:50. The amino acid sequence of $PfspN(O)_{129}$ is denoted SEQ ID NO:51.

Example 6

This example describes studies confirming the specificity of IgE enriched antiserum from CQQ2 to fspn protein.

Three different petri dishes (100 mm) were overlaid with 300 microliter per plate of *E. coli* (XL1 Blue, O.D.$_{600}$=500). A drop (about 100 pfu/drop) of each of the eighteen isolated phage clones was dropped onto each plate (18 phage clones/plate). Using the methods described in Example 5 above, the plates were incubated, filter lifted and the filters immunoscreened with IgE enriched antiserum from CQQ2, antiserum from a *D. Immitis* infected dog and antiserum from rabbits injected with flea saliva product from peak N (as described in Example 3 of related PCT Publication No. Wo 96/11,271).

The results of the experiment indicate that both the IgE enriched CQQ2 antiserum and the antiserum specific for peak N flea saliva product bind to the products of the purified phage clones significantly better than the antiserum from a *D. Immitis* infected dog.

Example 7

This example describes the isolation of nucleic acid molecules encoding a fspG flea saliva protein. This example also describes expression of a fspG protein by bacteria.

A DNA probe labeled with $^{32}p$ comprising nucleotides from $nfspG4_{610}$ (described in Example 2) was used to screen a flea salivary gland cDNA library (described in Example 6 of related PCT Publication No. WO 96/11,706) using standard hybridization techniques. A clone was isolated having about a 595 nucleotide insert, referred to herein as $nfspG5_{595}$ having a nucleic acid sequence of the coding strand which is denoted herein as SEQ ID NO:52. Translation of SEQ ID NO:52 suggests that nucleic acid molecule $nfspG5_{595}$ encodes a full-length flea salivary protein of about 90 amino acids, referred to herein as $PfspG5_{90}$, having amino acid sequence SEQ ID NO:53, assuming an open reading frame in which the initiation codon spans from about nucleotide 46 through about nucleotide 48 of SEQ ID NO:52 and the termination codon spans from about nucleotide 316 through about nucleotide 318 of SEQ ID NO:52. The complement of SEQ ID NO:52 is represented herein by SEQ ID NO:54. The coding region encoding $PfspG5_{90}$, is represented by nucleic acid molecule $nfspG5_{270}$, having a coding strand with the nucleic acid sequence represented by SEQ ID NO:55 and a complementary strand with nucleic acid sequence SEQ ID NO:57. The amino acid sequence of $PfspG5_{90}$ (i.e., SEQ ID NO:53) predicts that $PfspG5_{90}$ has an estimated molecular weight of about 9.6 kD and an estimated pI of about 9.28.

Analysis of SEQ ID NO:53 suggests the presence of a signal peptide encoded by a stretch of amino acids spanning from about amino acid 1 through about amino acid 19. The proposed mature protein, denoted herein as $PfsG5_{71}$, contains about 71 amino acids which is represented herein as SEQ ID NO:59. The complement of SEQ ID NO:58 is represented by SEQ ID NO:60. The amino acid sequence of $PfspG5_{71}$ (i.e., SEQ ID NO:59) predicts that $PfspG5_{71}$ has an estimated molecular weight of about 7.48 kD, and an estimated pI of about 8.28.

Comparison of amino acid sequence SEQ ID NO:53 with amino acid sequences reported in GenBank indicates that SEQ ID NO:53 showed the most homology, i.e., about 38% identity between SEQ ID NO:53 and a *Ctenocephalides felis* flea salivary protein FS-H precursor (GenBank accession U63544). Comparison of nucleic acid sequence SEQ ID NO:52 with nucleic acid sequences reported in GenBank indicates that SEQ ID NO:52 showed the most homology, i.e., about 63% identity between SEQ ID NO:52 and a *Ctenocephalides felis* flea salivary protein FS-H precursor gene (GenBank accession U63544).

Flea salivary protein $PfspG5_{71}$ was produced in the following manner. An about 213 bp nucleic acid molecule, referred to herein as $nfspG5_{213}$ (designed to encode an apparently mature flea salivary protein) was PCR amplified from $nfspG5_{595}$ using sense primer G7 having the nucleotide sequence 5' A GTG GAT CCG TCA AAA ATG GTC ACT G-3' (containing an BamHI-site shown in bold; denoted SEQ ID NO:79) and anti-sense primer G8 having the nucleotide sequence 5' CC GGA ATT CGG TTA TTC GCA ATA ACA GT-3' (containing a EcoRI shown in bold; denoted SEQ ID NO:80). The resulting PCR product $nfspG5_{213}$ was digested with BamHI and EcoRI restriction endonucleases, gel purified, and subcloned into expression vector lambda$P_R$/$T^2$ori/S10HIS-RSET-A9, that had been digested with BamHI and EcoRI and dephosphorylated. The resultant recombinant molecule, referred to herein as pCro-$nfspG5_{213}$, was transformed into *E. coli* BL-21 competent cells (available from Novagen, Madison, Wis.) to form recombinant cell *E. coli*:pCro-$nfspG5_{213}$. The recombinant cell was cultured and induced as described in Example 11A of related PCT Publication No. WO 96/11,271. Immunoblot analysis of the proteins using a T7 antibody showed expression of an about 12 kD protein in the induced sample but not in the uninduced sample.

Example 8

This example describes the further sequencing of a nucleic acid sequence encoding a fspI flea saliva protein. This example also describes expression of a fspI protein by bacteria.

The nucleic acid molecule denoted $nfspI_{573}$ described in Example 6 of related PCT Publication No. WO 96/11,706 was further sequenced using standard nucleotide sequencing methods. A nucleic acid molecule was identified of about 1007 nucleotides, referred to herein as $nfspI_{1007}$, the coding strand is denoted herein as SEQ ID NO:61. Translation of SEQ ID NO:61 suggests that SEQ ID NO:61 encodes a non-full-length flea salivary protein of about 155 amino acids, referred to herein as $PfSPI_{155}$, having amino acid sequence SEQ ID NO:62, assuming the first codon spans from about nucleotide 1 through about nucleotide 3 of SEQ ID NO:61 and the termination codon spans from about nucleotide 466 through about nucleotide 468 of SEQ ID NO:61. The complement of SEQ ID NO:61 is represented herein by SEQ ID NO:63.

Flea salivary protein $PfspI_{158}$ was produced in the following manner. An about 474-bp nucleic acid molecule, referred to herein as $nfspI_{474}$ (designed to encode an apparently mature flea salivary protein) was PCR amplified from $nfspI_{1007}$ using sense primer I1 having the nucleotide sequence 5' GCG CGG ATC CGC ATA TGG AAG ACA TCT GGA AAG TTA ATA AAA AAT GTA CAT CAG-3' (containing an BamHI-site shown in bold as well as nucleic acid sequence encoding three amino acids, Glu-Asp-Isoleucine, shown in italics; denoted SEQ ID NO:81) and anti-sense primer I2 having the nucleotide sequence 5' CCG GAA TTC TTA TTT ATT TTT TGG TCG ACA ATA ACA AAA GTT TCC-3' (containing a EcoRI shown in bold; denoted SEQ ID NO:82). The resulting PCR product $nfspI_{474}$, which contained the nucleic acid sequences incorporated into primer I1 that encode three amino acids, was digested with BamHI and EcoRI restriction endonucleases, gel purified, and subcloned into expression vector lambda$P_R$/$T^2$ori/S10HIS-RSET-A9, that had been digested with BamHI and XbaI and dephosphorylated. The resultant recombinant molecule, referred to herein as pCro-$nfspI_{474}$, was transformed into *E. coli* BL-21 competent cells (available from Novagen, Madison, Wis.) to form recombinant cell *E. coli*:pCro-$nfspI_{474}$. The recombinant cell was cultured and protein production resolved using the methods described in Example 11A of related PCT Publication No. WO 96/11,271. Immunoblot analysis of the proteins using a T7 antibody showed expression of an about 30 kD protein in the induced sample but not in the uninduced sample.

Example 9

This example describes the isolation of nucleic acid molecules encoding a fspN flea saliva protein.

A DNA probe comprising nucleotides from $nfspN(B)_{612}$ (SEQ ID NO:52 of related PCT Publication No. WO 96/11,706) was labeled with $^{32}P$ and used to screen the flea salivary gland cDNA library using standard hybridization techniques. A clone was isolated having about a 1205 nucleotide insert, referred to herein as $nfspN5_{1205}$ having a nucleic acid sequence of the coding strand which is denoted herein as SEQ ID NO:64. Translation of SEQ ID NO:64 suggests that nucleic acid molecule $nfspN5_{1205}$ encodes a non-full-length flea salivary protein of about 353 amino acids, referred to herein as $PfspN5_{353}$, having amino acid sequence SEQ ID NO:65, assuming an open reading frame in which the initiation codon spans from about nucleotide 4 through about nucleotide 6 of SEQ ID NO:64 and the termination codon spans from about nucleotide 1060 through about nucleotide 1062 of SEQ ID NO:64. The complement of SEQ ID NO:64 is represented herein by SEQ ID NO:66. The coding region encoding $PfspN5_{353}$, is represented by nucleic acid molecule $nfspN5_{1059}$, having a coding strand with the nucleic acid sequence represented by SEQ ID NO:67 and a complementary strand with nucleic acid sequence SEQ ID NO:69. The amino acid sequence of $PfspN5_{353}$ (i.e., SEQ ID NO:65) predicts that $PfspN5_{353}$ has an estimated molecular weight of about 39.7 kD and an estimated pI of about 9.45.

Comparison of amino acid sequence SEQ ID NO:65 with amino acid sequences reported in GenBank indicates that SEQ ID NO:65 showed the most homology, i.e., about 32% identity between SEQ ID NO:65 and a Human prostatic acid phosphatase precursor protein (GenBank accession P15309). A GenBank homology search revealed no significant homology between SEQ ID NO:64 and known nucleic acid sequences.

Example 10

This example describes the isolation of nucleic acid molecules encoding a fspN flea saliva protein identified using IgE antibodies isolated from a dog having clinical flea allergy dermatitis.

A pool of sera (referred to herein as Pool #4) was collected from numerous known to have clinic flea allergy dermatitis (FAD). Pool #4 sera was used to identify flea saliva antigens that bind specifically to IgE antibodies in the FAD dog sera as follows. Flea saliva extract was collected using the general methods described in Examples 1 and 2 of related PCT Publication No. WO 96/11,706, except a carboxymethyl cation exchange (CM) membrane (available from Schleicher and Scheull, Keene, N.H.) was used rather than a Durapore® membrane. In addition, flea saliva extract was eluted from the membrane by contacting the membrane in an extraction buffer of 2.5 M NaCl, 5% isopropyl alcohol (IPA) and 20 mM Tris, pH 8.0. The membrane was eluted overnight at room temperature. The flea saliva extract was resolved by high pressure liquid chromatography (HPLC) using the method generally described in Example 2 of related PCT Publication No. WO 96/11,706. Proteins contained in the HPLC fractions were resolved on a 16% Tris-glycine SDS PAGE gel. Proteins on the gel were then blotted to an Immobilon P™ filter (available from Millipore Co., Bedford, Mass.) using standard Western Blot techniques. IgE antibodies bound to protein on the blot was then detected as follows. The blot was first incubated with about a 1:200 dilution of Pool #4 sera using standard antibody hybridization techniques, washed, and then incubated with about a 1:500 dilution of a 145 $\mu$g/milliliter solution of biotinylated human Fc R alpha chain protein using standard Western Blot techniques. Following washing, the blot was incubated with about a 1:5,000 dilution of streptavidin conjugated to alkaline phosphatase (available from Sigma, St. Louis, Mo.). About 10 milliliter of BCIP/NBT substrate (available from Gibco BRL, Gaithersburg, Md.) was then added to the blot, incubated until visible bands appeared, at room temperature, and then the blot was rinsed in water to stop the reaction. Protein bands were detected in samples containing Fractions 34, 37, 38, 47, 49, 51, 52 and 53.

Amino (N-) terminal amino acid sequencing analysis was performed on protein contained in the about 40 kD protein band identified in the sample containing Fraction 52, using standard procedures known to those in the art (see, for example, Geisow et al., 1989, in *Protein Sequencing: A Practical Approach*, JBC Findlay and MJ Geisow (eds.), IRL Press, Oxford, England, pp. 85–98; Hewick et al., 1981, *J. Biol. Chem*., Vol. 256, pp. 7990–7997). The N-terminal partial amino acid sequence of the protein was determined to be X Glu Leu Lys Phe Val Phe Val Met Val Lys Gly Pro Asp His Glu Ala Cys Asn Tyr Ala Gly Gly X Gln (denoted herein as SEQ ID NO:70; wherein "X" represents any amino acid residue).

Synthetic oligonucleotide primers were designed using SEQ ID NO:70 and used to isolate a nucleic acid molecule encoding SEQ ID NO:70 as follows. Sense primer 1 having the nucleotide sequence 5' AAA TTT GTA(T) TTT GTA(T) ATG GTA(T) AAA GGA(T) CCA(T) GAT CAT GAA GC-3' (denoted SEQ ID NO:83) was used in combination with the M13 forward universal standard primer 5' GTAAAACGACGGCCAGT 3' (denoted SEQ ID NO:84) to produce a PCR product from the a flea salivary gland cDNA library described above in Example 9. PCR amplification was conducted using standard techniques. The resulting PCR amplification product was a fragment of about 406 nucleotides, denoted herein as nfspN$6_{406}$. The PCR product was cloned into the InVitrogen, Corp., TA™ cloning vector (procedures provided by InVitrogen, Corp.) and subjected to DNA sequence analysis using standard techniques.

The nucleic acid sequence of the coding strand of nfspN$6_{406}$ is denoted herein as SEQ ID NO:71. Translation of SEQ ID NO:71 suggests that nucleic acid molecule nfspN$6_{406}$ encodes a non-full-length flea salivary protein of about 135 amino acids, referred to herein as PfspN$6_{135}$, having amino acid sequence SEQ ID NO:72, assuming the first codon spans from about nucleotide 1 through about nucleotide 3 of SEQ ID NO:71 and the last codon spans from about nucleotide 403 through about nucleotide 405 of SEQ ID NO:71. The complement of SEQ ID NO:71 is represented herein by SEQ ID NO:73.

A GenBank homology search revealed no significant homology between amino acid sequence SEQ ID NO:72 and nucleic acid sequence SEQ ID NO:71 and known amino acid sequences or nucleic acid sequences, respectively.

Example 11

This example describes the isolation of nucleic acid molecules encoding a fspJ flea saliva protein.

Degenerate oligonucleotide primers were designed from the amino acid sequence deduced for fspJ (described in Example 4 of related PCT Publication No.WO 96/11,706) and were used to isolate a fspJ nucleic acid molecule as follows. Two synthetic oligonucleotides were synthesized that corresponded to the region of fspJ spanning from about residues 7 through about 26 of SEQ ID NO:8 of related PCT Publication No. WO 96/11,706. Primer 1, a "sense" primer corresponding to amino acid residues from about residue 7 to about 16 of SEQ ID NO:8 of related PCT Publication No. WO 96/11,706, has the nucleotide sequence 5' CAT GAA CCA(T) GGA(T) AAT ACA(T) CGA(T) AAA(G) ATA(C/T) A(C)G 3' (denoted herein as SEQ ID NO:84). Primer 2, a "sense" primer corresponding to amino acid residues form about residue 17 through about 26 of SEQ ID NO:8 of related PCT Publication No. WO 96/11,706, has the nucleic acid sequence 5' GAA GTA(T) ATG GAC(T) AAA TTA(G) AGA(G) CAA(G) GC-3' (denoted herein as SEQ ID NO:86).

PCR amplification of fragments from the flea salivary gland cDNA library described above in Example 9 was conducted using standard techniques. PCR amplification products were generated using a combination of Primer 1 and M13 primer (denoted SEQ ID NO:85). The resultant PCR products were used for a nested PCR amplification using Primer 2 and the T7 standard primer 5' GTA ATA CGA CTC ACT ATA TAG GGC 3' (denoted SEQ ID NO:88). The resultant PCR product, a fragment of about 420 nucleotides, denoted herein as nfspJ$_{420}$. The PCR product was cloned into the InVitrogen, Corp., TA™ cloning vector (procedures provided by InVitrogen, Corp.) and subjected to DNA sequence analysis using standard techniques.

The nucleic acid sequence of the coding strand of nfspJ$_{420}$ is denoted herein as SEQ ID NO:74. Translation of SEQ ID NO:74 suggests that nucleic acid molecule nfspJ$_{420}$ encodes a non-full-length flea salivary protein of about 72 amino acids, referred to herein as PfspJ$_{72}$, having amino acid sequence SEQ ID NO:75, assuming the first codon spans from about nucleotide 1 through about nucleotide 3 of SEQ ID NO:74 and the last codon spans from about nucleotide 214 through about nucleotide 216 of SEQ ID NO:74. The complement of SEQ ID NO:74 is represented herein by SEQ ID NO:76.

A GenBank homology search revealed no significant homology between amino acid sequence SEQ ID NO:75 and nucleic acid sequence SEQ ID NO:74 and known amino acid sequences or nucleic acid sequences, respectively.

Example 12

This example describes the amino acid sequence analysis of an isolated and HPLC purified fspN7 flea saliva protein.

Fractions of flea saliva proteins described above in Example 10 were tested for the ability to stimulate T cell clones that respond specifically to the flea saliva extract described in Example 10 (FS-specific T cells). T cell activation were performed using standard methods such as those described in *Current Protocols in Immunology*, Vol. 1, Chapter 3 [3.13.2], ed. J. E. Coligan et al., pub. Wiley Interscience, 1993. Briefly, about $10^4$ FS-1-specific T cells (clone CPO2-7; isolated from dog CPO2 described in Example 8 of related PCT Patent Publication No. WO 96/11,271) were added to individual wells of a 96 well tissue culture plate, in the presence of about 2×104 autologous antigen presenting cells (isolated by ficoll gradient from dog CPO2) and about 100 units/milliliter of recombinant human interleukin-2 (Proleukin®; available from Chiron Inc., Emeryville, Calif.). About 1 microliter of each fraction of protein resolved by HPLC was to added to each well in triplicate. The cells were incubated for about 4 to about 6 days. About 16 hours prior to harvesting, about 1 μCi of tritiated thymidine (available from Amersham Inc., Arlington Heights, Ill.) was added to each well. The cells were then harvested and the amount of tritium incorporated into the cellular protein was determined. The results indicated that protein contained in a HPLC fraction containing fspN protein (Fraction 51) stimulated the FS-specific T cells.

Amino (N-) terminal amino acid sequencing analysis was performed on protein contained in Fraction 51 using standard procedures known to those in the art (see, for example, Geisow et al., ibid.; Hewick et al., 1981, ibid.). The N-terminal partial amino acid sequence of the band was determined to be Asn Asp Lys Leu Gln Phe Val Phe Val Met Ala Arg Gly Pro Asp His Glu Ala Cys Asn Tyr Pro Gly Gly Pro (denoted herein as SEQ ID NO:78).

Example 13

This example describes the amino acid sequence analysis of an isolated and HPLC purified fspM2 flea saliva protein.

Proteins contained within Fraction 47 described above in Example 10 were resolved on a 16% Tris-glycine SDS PAGE gel. A major band at about 34 kD was identified. Amino (N-) terminal amino acid sequencing analysis was performed on protein contained in the about 34 kD using standard procedures known to those in the art (see, for example, Geisow et al., ibid.; Hewick et al., 1981, ibid.). The N-terminal partial amino acid sequence of the band was determined to be Tyr Phe Asn Lys leu Val Gln Ser Trp Thr Glu Pro Met Val Phe Lys Tyr Pro Tyr (denoted herein as SEQ ID NO:87).

SEQUENCE LISTING

```
(1) GENERAL INFORMATION:

   (iii) NUMBER OF SEQUENCES: 88


(2) INFORMATION FOR SEQ ID NO: 1:

     (i) SEQUENCE CHARACTERISTICS:
          (A) LENGTH: 26 amino acids
          (B) TYPE: amino acid
          (C) STRANDEDNESS: <Unknown>
          (D) TOPOLOGY: linear

    (ii) MOLECULE TYPE: protein

    (xi) SEQUENCE DESCRIPTION: SEQ ID NO: 1:

Met Arg Gly Asn His Val Phe Leu Glu Asp Gly Met Ala Asp Met Thr
1               5                   10                  15

Gly Gly Gln Gln Met Gly Arg Asp Leu Tyr
            20                  25


(2) INFORMATION FOR SEQ ID NO: 2:

     (i) SEQUENCE CHARACTERISTICS:
          (A) LENGTH: 12 amino acids
          (B) TYPE: amino acid
          (C) STRANDEDNESS: <Unknown>
          (D) TOPOLOGY: linear

    (ii) MOLECULE TYPE: protein

    (ix) FEATURE:
          (A) NAME/KEY: Xaa = Tyr or Asp
```

```
          (B) LOCATION: 5

    (ix) FEATURE:
          (A) NAME/KEY: Xaa = any amino acid
          (B) LOCATION: 6

    (xi) SEQUENCE DESCRIPTION: SEQ ID NO: 2:

Lys Tyr Arg Asn Xaa Xaa Thr Asn Asp Pro Gln Tyr
1               5                   10


(2) INFORMATION FOR SEQ ID NO: 3:

     (i) SEQUENCE CHARACTERISTICS:
          (A) LENGTH: 27 amino acids
          (B) TYPE: amino acid
          (C) STRANDEDNESS: <Unknown>
          (D) TOPOLOGY: linear

    (ii) MOLECULE TYPE: protein

    (xi) SEQUENCE DESCRIPTION: SEQ ID NO: 3:

Glu Ile Lys Arg Asn Asp Arg Glu Pro Gly Asn Leu Ser Lys Ile Arg
1               5                   10                  15

Thr Val Met Asp Lys Val Ile Lys Gln Thr Gln
            20                  25


(2) INFORMATION FOR SEQ ID NO: 4:

     (i) SEQUENCE CHARACTERISTICS:
          (A) LENGTH: 23 amino acids
          (B) TYPE: amino acid
          (C) STRANDEDNESS: <Unknown>
          (D) TOPOLOGY: linear

    (ii) MOLECULE TYPE: protein

    (ix) FEATURE:
          (A) NAME/KEY: Xaa = Ala or His
          (B) LOCATION: 8

    (ix) FEATURE:
          (A) NAME/KEY: Xaa = Ala or His
          (B) LOCATION: 9

    (xi) SEQUENCE DESCRIPTION: SEQ ID NO: 4:

Leu Lys Asp Asn Asp Ile Tyr Xaa Xaa Arg Asp Ile Asn Glu Ile Leu
1               5                   10                  15

Arg Val Leu Asp Pro Ser Lys
            20


(2) INFORMATION FOR SEQ ID NO: 5:

     (i) SEQUENCE CHARACTERISTICS:
          (A) LENGTH: 27 amino acids
          (B) TYPE: amino acid
          (C) STRANDEDNESS: <Unknown>
          (D) TOPOLOGY: linear

    (ii) MOLECULE TYPE: protein

    (ix) FEATURE:
          (A) NAME/KEY: Xaa = any amino acid
          (B) LOCATION: 12

    (ix) FEATURE:
          (A) NAME/KEY: Xaa = any amino acid
          (B) LOCATION: 18

    (xi) SEQUENCE DESCRIPTION: SEQ ID NO: 5:

Asn Tyr Gly Arg Val Gln Ile Glu Asp Tyr Thr Xaa Ser Asn His Lys
```

-continued

```
1               5                   10                  15

Asp Xaa Glu Glu Lys Asp Gln Ile Asn Gly Leu
            20                  25
```

(2) INFORMATION FOR SEQ ID NO: 6:

(i) SEQUENCE CHARACTERISTICS:
(A) LENGTH: 18 amino acids
(B) TYPE: amino acid
(C) STRANDEDNESS: <Unknown>
(D) TOPOLOGY: linear (ii) MOLECULE TYPE: protein (ix) FEATURE:
(A) NAME/KEY: Xaa = any amino acid
(B) LOCATION: 5

(xi) SEQUENCE DESCRIPTION: SEQ ID NO: 6:

```
Lys Tyr Arg Asn Xaa Tyr Thr Asn Asp Pro Gln Leu Lys Leu Leu Asp
1               5                   10                  15

Glu Gly
```

(2) INFORMATION FOR SEQ ID NO: 7:

(i) SEQUENCE CHARACTERISTICS:
(A) LENGTH: 22 amino acids
(B) TYPE: amino acid
(C) STRANDEDNESS: <Unknown>
(D) TOPOLOGY: linear (ii) MOLECULE TYPE: protein (ix) FEATURE:
(A) NAME/KEY: Xaa = any amino acid
(B) LOCATION: 13

(ix) FEATURE:
(A) NAME/KEY: Xaa = any amino acid
(B) LOCATION: 19

(ix) FEATURE:
(A) NAME/KEY: Xaa = any amino acid
(B) LOCATION: 21

(xi) SEQUENCE DESCRIPTION: SEQ ID NO: 7:

```
Tyr Phe Asn Asp Gln Ile Lys Ser Val Met Glu Pro Xaa Val Phe Lys
1               5                   10                  15

Tyr Pro Xaa Ala Xaa Leu
            20
```

(2) INFORMATION FOR SEQ ID NO: 8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..20
(D) OTHER INFORMATION: /label= primer (xi) SEQUENCE DESCRIPTION: SEQ ID NO: 8:

```
TGRTTTCCWA TRAARTCTTC                                            20
```

```
(2) INFORMATION FOR SEQ ID NO: 9:

     (i) SEQUENCE CHARACTERISTICS:
          (A) LENGTH: 225 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 9:

GAATTCGGCA CGAGTGAAAT TCAATATTTT GTTTTACATT AAATTTTTCA AATTCGATAT      60

GAAATTTTTA CTGGCAATTT GCGTGTTGTG TGTTTTATTA AATCAAGTAT CTATGTCAAA     120

AATGGTCACT GAAAAGTGTA AGTCAGGTGG AAATAATCCA AGTACAGAAG AGGTGTCAAT     180

ACCATCTGGG AAGCTTACTA TTGAAGATTT TTGTATTGGA AATCA                     225


(2) INFORMATION FOR SEQ ID NO: 10:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: misc_feature
          (B) LOCATION: 1..15
          (D) OTHER INFORMATION: /label= primer

    (xi) SEQUENCE DESCRIPTION: SEQ ID NO: 10:

AATTCGGCAC GAGTG                                                       15


(2) INFORMATION FOR SEQ ID NO: 11:

     (i) SEQUENCE CHARACTERISTICS:
          (A) LENGTH: 565 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 45..314

    (xi) SEQUENCE DESCRIPTION: SEQ ID NO: 11:

TGAAATTCAA TATTTTGTTT TACATTAAAT TTTTCAAATT CGAT ATG AAA TTT TTA      56
                                                 Met Lys Phe Leu
                                                   1

CTG GCA ATT TGC GTG TTG TGT GTT TTA TTA AAT CAA GTA TCT ATG TCA      104
Leu Ala Ile Cys Val Leu Cys Val Leu Leu Asn Gln Val Ser Met Ser
  5                  10                  15                  20

AAA ATG GTC ACT GAA AAG TGT AAG TCA GGT GGA AAT AAT CCA AGT ACA      152
Lys Met Val Thr Glu Lys Cys Lys Ser Gly Gly Asn Asn Pro Ser Thr
                 25                  30                  35

GAA GAG GTG TCA ATA CCA TCT GGG AAG CTT ACT ATT GAA GAT TTT TGT      200
Glu Glu Val Ser Ile Pro Ser Gly Lys Leu Thr Ile Glu Asp Phe Cys
             40                  45                  50

ATT GGA AAT CAT CAA AGT TGC AAA ATA TTT TAC AAA AGT CAA TGT GGA      248
Ile Gly Asn His Gln Ser Cys Lys Ile Phe Tyr Lys Ser Gln Cys Gly
         55                  60                  65

TTT GGA GGT GGT GCT TGT GGA AAC GGT GGT TCA ACA CGA CCA AAT CAA      296
Phe Gly Gly Gly Ala Cys Gly Asn Gly Gly Ser Thr Arg Pro Asn Gln
```

-continued

```
     70                  75                  80

AAA CAC TGT TAT TGC GAA TAACCATATT CCGGATGAAA GACCAAATTG             344
Lys His Cys Tyr Cys Glu
 85                 90

ATATAAATTA CTAAAATTAT GCTAGATAGC AATCATAAAA TTTTGAAGTT TTCAATGATC    404

CTAACATGTT TTGCCTCCAA TTTATTTTAA CAGCAAATTG CTGGAACTTA CCGTACCGTA    464

ACTAAATGTT CAAGAAATAC TGAATGTTTA CAAATAGATT ATTATAAATA TTGTAACATT    524

GTCTAATATT TATAAGAATT ATATAAACTG AATTGCAAAA A                        565
```

(2) INFORMATION FOR SEQ ID NO: 12:

(i) SEQUENCE CHARACTERISTICS:
(A) LENGTH: 90 amino acids
(B) TYPE: amino acid
(D) TOPOLOGY: linear (ii) MOLECULE TYPE: protein (xi) SEQUENCE DESCRIPTION: SEQ ID NO: 12:

```
Met Lys Phe Leu Leu Ala Ile Cys Val Leu Cys Val Leu Leu Asn Gln
  1               5                  10                  15

Val Ser Met Ser Lys Met Val Thr Glu Lys Cys Lys Ser Gly Gly Asn
            20                  25                  30

Asn Pro Ser Thr Glu Glu Val Ser Ile Pro Ser Gly Lys Leu Thr Ile
        35                  40                  45

Glu Asp Phe Cys Ile Gly Asn His Gln Ser Cys Lys Ile Phe Tyr Lys
     50                  55                  60

Ser Gln Cys Gly Phe Gly Gly Gly Ala Cys Gly Asn Gly Gly Ser Thr
 65                  70                  75                  80

Arg Pro Asn Gln Lys His Cys Tyr Cys Glu
                 85                  90
```

(2) INFORMATION FOR SEQ ID NO: 13:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..270

(xi) SEQUENCE DESCRIPTION: SEQ ID NO: 13:

```
ATG AAA TTT TTA CTG GCA ATT TGC GTG TTG TGT GTT TTA TTA AAT CAA       48
Met Lys Phe Leu Leu Ala Ile Cys Val Leu Cys Val Leu Leu Asn Gln
  1               5                  10                  15

GTA TCT ATG TCA AAA ATG GTC ACT GAA AAG TGT AAG TCA GGT GGA AAT       96
Val Ser Met Ser Lys Met Val Thr Glu Lys Cys Lys Ser Gly Gly Asn
            20                  25                  30

AAT CCA AGT ACA GAA GAG GTG TCA ATA CCA TCT GGG AAG CTT ACT ATT      144
Asn Pro Ser Thr Glu Glu Val Ser Ile Pro Ser Gly Lys Leu Thr Ile
        35                  40                  45

GAA GAT TTT TGT ATT GGA AAT CAT CAA AGT TGC AAA ATA TTT TAC AAA      192
Glu Asp Phe Cys Ile Gly Asn His Gln Ser Cys Lys Ile Phe Tyr Lys
     50                  55                  60

AGT CAA TGT GGA TTT GGA GGT GGT GCT TGT GGA AAC GGT GGT TCA ACA      240
Ser Gln Cys Gly Phe Gly Gly Gly Ala Cys Gly Asn Gly Gly Ser Thr
```

```
 65                  70                  75                  80

CGA CCA AAT CAA AAA CAC TGT TAT TGC GAA                                  270
Arg Pro Asn Gln Lys His Cys Tyr Cys Glu
                 85                  90
```

(2) INFORMATION FOR SEQ ID NO: 14:

(i) SEQUENCE CHARACTERISTICS:
(A) LENGTH: 90 amino acids
(B) TYPE: amino acid
(D) TOPOLOGY: linear (ii) MOLECULE TYPE: protein (xi) SEQUENCE DESCRIPTION: SEQ ID NO: 14:

```
Met Lys Phe Leu Leu Ala Ile Cys Val Leu Cys Val Leu Leu Asn Gln
  1               5                  10                  15

Val Ser Met Ser Lys Met Val Thr Glu Lys Cys Lys Ser Gly Gly Asn
             20                  25                  30

Asn Pro Ser Thr Glu Glu Val Ser Ile Pro Ser Gly Lys Leu Thr Ile
         35                  40                  45

Glu Asp Phe Cys Ile Gly Asn His Gln Ser Cys Lys Ile Phe Tyr Lys
     50                  55                  60

Ser Gln Cys Gly Phe Gly Gly Gly Ala Cys Gly Asn Gly Gly Ser Thr
 65                  70                  75                  80

Arg Pro Asn Gln Lys His Cys Tyr Cys Glu
                 85                  90
```

(2) INFORMATION FOR SEQ ID NO: 15:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..26
(D) OTHER INFORMATION: /label= primer (xi) SEQUENCE DESCRIPTION: SEQ ID NO: 15:

```
AGTGGATCCG TCAAAAATGG TCACTG                                              26
```

(2) INFORMATION FOR SEQ ID NO: 16:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..28
(D) OTHER INFORMATION: /label= primer (xi) SEQUENCE DESCRIPTION: SEQ ID NO: 16:

```
CCGGAATTCG GTTATTCGCA ATAACAGT                                            28
```

(2) INFORMATION FOR SEQ ID NO: 17:

```
     (i) SEQUENCE CHARACTERISTICS:
          (A) LENGTH: 897 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 97..567

    (xi) SEQUENCE DESCRIPTION: SEQ ID NO: 17:

CCGAAATCTC CTATCACAGT GTACGGAGTG TAAAATATTG TTGAAGTATT              60

TTAATTTATT CGAAAAGGAG ATTTCATTAA ATAAAA ATG GTT TAC GAA AGT GAC     114
                                        Met Val Tyr Glu Ser Asp
                                         1               5

TTT TAC ACG ACC CGT CGG CCC TAC AGT CGT CCG GCT TTG TCT TCA TAC     162
Phe Tyr Thr Thr Arg Arg Pro Tyr Ser Arg Pro Ala Leu Ser Ser Tyr
            10                  15                  20

TCC GTA ACG GCA CGT CCA GAG CCG GTT CCT TGG GAC AAA TTG CCG TTC     210
Ser Val Thr Ala Arg Pro Glu Pro Val Pro Trp Asp Lys Leu Phe Cys
        25                  30                  35

GTC CCC CGT CCA AGT TTG GTA GCA GAT CCC ATA ACA GCA TTT TGC AGG     258
Val Pro Arg Pro Ser Leu Val Ala Asp Pro Ile Thr Ala Phe Cys Lys
     40                  45                  50

CGA AAA CCT CGC CGA GAA GAA GTT GTT CAA AAA GAG TCC ATT GTT CGA     306
Arg Lys Pro Arg Arg Glu Glu Val Val Gln Lys Glu Ser Ile Val Arg
 55                  60                  65                  70

AGG ATC AAT TCT GCA GGA ATT AAA CCC AGC CAG AGA GTT TTA TCG GCT     354
Arg Ile Asn Ser Ala Gly Ile Lys Pro Ser Gln Arg Val Leu Ser Ala
                 75                  80                  85

CCA ATA AGA GAA TAC GAA TCC CCA AGG GAC CAG ACC AGG CGT AAA GTT     402
Pro Ile Arg Glu Tyr Glu Ser Pro Arg Asp Gln Thr Arg Arg Lys Val
            90                  95                 100

TTG GAA AGC GTC AGA AGA CAA GAA GCT TTT CTG AAC CAA GGA GGA ATT     450
Leu Glu Ser Val Arg Arg Gln Glu Ala Phe Leu Asn Gln Gly Gly Ile
        105                 110                 115

TGT CCA TTG ACC ACC AGA AAT GAT GAC ATG GAT AGA CTT CTA CCC CGT     498
Cys Pro Leu Thr Thr Arg Asn Asp Asp Met Asp Arg Leu Leu Pro Arg
    120                 125                 130

CTC CAC AGT TCA CAC ACA ACA CCT TCT GCG GAT AGG AAA GTT TTG TTG     546
Leu His Ser Ser His Thr Thr Pro Ser Ala Asp Arg Lys Val Leu Leu
135                 140                 145                 150

ACC ACT TTT CAC AGA AGA TAC T GATTAAAAAT GAAAGTTAAG AACGATACGA      598
Thr Thr Phe His Arg Arg Tyr
                155

AAGTCATGTG GTGTTTTTTA TACATTCTTT ATTAATCGAT ATTCCTAACG AACGATACGA   658

TAACTTTCGA TAACTTTTTC TGGTTAATTT TGACAAAATA TGCATTTGCA AGCATAACAT   718

TCATTTTCAA GGCAAACGCT TTCTGATGAT TATCTTGTTA AAAGTGTGGA AACAAGCGTA   778

GTGTTAACAA ATGCATTGCT TGTTTTGATT ATTTATTTAT CTATTATATA TTCCATATTG   838

TATTGTAGGT GGTGTACTTG GTATTACTAA TACACGTACT TTGTGAAAAA AAAAAAAAA    897


(2) INFORMATION FOR SEQ ID NO: 18:

     (i) SEQUENCE CHARACTERISTICS:
          (A) LENGTH: 157 amino acids
          (B) TYPE: amino acid
          (D) TOPOLOGY: linear

    (ii) MOLECULE TYPE: protein
```

(xi) SEQUENCE DESCRIPTION: SEQ ID NO: 18:

```
Met Val Tyr Glu Ser Asp Phe Tyr Thr Thr Arg Arg Pro Tyr Ser Arg
  1               5                  10                  15

Pro Ala Leu Ser Ser Tyr Ser Val Thr Ala Arg Pro Glu Pro Val Pro
             20                  25                  30

Trp Asp Lys Leu Pro Phe Val Pro Arg Pro Ser Leu Val Ala Asp Pro
         35                  40                  45

Ile Thr Ala Phe Cys Lys Arg Lys Pro Arg Arg Glu Glu Val Val Gln
     50                  55                  60

Lys Glu Ser Ile Val Arg Arg Ile Asn Ser Ala Gly Ile Lys Pro Ser
 65                  70                  75                  80

Gln Arg Val Leu Ser Ala Pro Ile Arg Glu Tyr Glu Ser Pro Arg Asp
                 85                  90                  95

Gln Thr Arg Arg Lys Val Leu Glu Ser Val Arg Arg Gln Glu Ala Phe
            100                 105                 110

Leu Asn Gln Gly Gly Ile Cys Pro Leu Thr Thr Arg Asn Asp Asp Met
        115                 120                 125

Asp Arg Leu Leu Pro Arg Leu His Ser Ser His Thr Thr Pro Ser Ala
    130                 135                 140

Asp Arg Lys Val Leu Leu Thr Thr Phe His Arg Arg Tyr
145                 150                 155
```

(2) INFORMATION FOR SEQ ID NO: 19:

(i) SEQUENCE CHARACTERISTICS:
(A) LENGTH: 471 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 19:

```
ATGGTTTACG AAAGTGACTT TTACACGACC CGTCGGCCCT ACAGTCGTCC GGCTTTGTCT     60

TCATACTCCG TAACGGCACG TCCAGAGCCG GTTCCTTGGG ACAAATTGCC GTTCGTCCCC    120

CGTCCAAGTT TGGTAGCAGA TCCCATAACA GCATTTTGCA AGCGAAAACC TCGCCGAGAA    180

GAAGTTGTTC AAAAAGAGTC CATTGTTCGA AGGATCAATT CTGCAGGAAT TAAACCCAGC    240

CAGAGAGTTT TATCGGCTCC AATAAGAGAA TACGAATCCC CAAGGGACCA GACCAGGCGT    300

AAAGTTTTGG AAAGCGTCAG AAGACAAGAA GCTTTTCTGA ACCAAGGAGG AATTTGTCCA    360

TTGACCACCA GAAATGATGA CATGGATAGA CTTCTACCCC GTCTCCACAG TTCACACACA    420

ACACCTTCTG CGGATAGGAA AGTTTTGTTG ACCACTTTTC ACAGAAGATA C             471
```

(2) INFORMATION FOR SEQ ID NO: 20:

(i) SEQUENCE CHARACTERISTICS:
(A) LENGTH: 2706 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 5..2706

(xi) SEQUENCE DESCRIPTION: SEQ ID NO: 20:

-continued

```
GCGG ATG AAG AGC ATC GAG GCT TAT ACA AAC AGA TAT GAA ATC ATA GCT        49
     Met Lys Ser Ile Glu Ala Tyr Thr Asn Arg Tyr Glu Ile Ile Ala
       1               5                  10                  15

TCT GAA ATA GTT AAT CTT CGA ATG AAA CCA GAT GAT TTT AAT TTA ATA        97
Ser Glu Ile Val Asn Leu Arg Met Lys Pro Asp Asp Phe Asn Leu Ile
                20                  25                  30

AAA GTT ATT GGT CGA GGA GCA TTT GGT GAA GTA CAG TTA GTG CGA CAC       145
Lys Val Ile Gly Arg Gly Ala Phe Gly Glu Val Gln Leu Val Arg His
            35                  40                  45

AAA TCA ACT GCA CAA GTT TTT GCT ATG AAA CGC CTA TCA AAA TTT GAA       193
Lys Ser Thr Ala Gln Val Phe Ala Met Lys Arg Leu Ser Lys Phe Glu
        50                  55                  60

ATG ATT AAG AGA CCA GAC TCT GCA TTT TTT TGG GAA GAA CGT CAT ATA       241
Met Ile Lys Arg Pro Asp Ser Ala Phe Phe Trp Glu Glu Arg His Ile
    65                  70                  75

ATG GCT CAT GCA AAA TCA GAA TGG ATT GTA CAA TTA CAT TTT GCT TTT       289
Met Ala His Ala Lys Ser Glu Trp Ile Val Gln Leu His Phe Ala Phe
 80                  85                  90                  95

CAA GAT CAA AAA TAT CTT TAT ATG GTC ATG GAT TAT ATG CCG GGG GGT       337
Gln Asp Gln Lys Tyr Leu Tyr Met Val Met Asp Tyr Met Pro Gly Gly
                100                 105                 110

GAC TTG GTG AGT CTT ATG TCC GAT TAT GAA ATT CCA GAA AAA TGG GCA       385
Asp Leu Val Ser Leu Met Ser Asp Tyr Glu Ile Pro Glu Lys Trp Ala
            115                 120                 125

ATG TTC TAT ACA ATG GAA GTG GTG CTA GCA CTT GAT ACA ATT CAC TCC       433
Met Phe Tyr Thr Met Glu Val Val Leu Ala Leu Asp Thr Ile His Ser
        130                 135                 140

ATG GGA TTT GTA CAT CGT GAT GTT AAA CCT GAT AAT ATG CTT CTA GAC       481
Met Gly Phe Val His Arg Asp Val Lys Pro Asp Asn Met Leu Leu Asp
    145                 150                 155

AAA TAT GGT CAT TTA AAG TTA GCT GAC TTT GGA ACC TGT ATG AAA ATG       529
Lys Tyr Gly His Leu Lys Leu Ala Asp Phe Gly Thr Cys Met Lys Met
160                 165                 170                 175

GAT ACA GAT GGT TTG GTA CGT TCT AAT AAT GCT GTT GGA ACG CCT GAT       577
Asp Thr Asp Gly Leu Val Arg Ser Asn Asn Ala Val Gly Thr Pro Asp
                180                 185                 190

TAC ATT TCT CCC GAA GTT TTG CAG TCC CAA GGT GGT GAA GGA GTT TAC       625
Tyr Ile Ser Pro Glu Val Leu Gln Ser Gln Gly Gly Glu Gly Val Tyr
            195                 200                 205

GGT CGT GAA TGC GAT TGG TGG TCT GTG GGA ATT TTT TTG TAT GAA ATG       673
Gly Arg Glu Cys Asp Trp Trp Ser Val Gly Ile Phe Leu Tyr Glu Met
        210                 215                 220

TTA TTT GGA GAA ACA CCT TTT TAT GCA GAC AGT TTG GTT GGA ACT TAC       721
Leu Phe Gly Glu Thr Pro Phe Tyr Ala Asp Ser Leu Val Gly Thr Tyr
    225                 230                 235

AGT AAA ATT ATG GAT CAC AGA AAC TCA TTA ACT TTT CCT CCA GAA GTG       769
Ser Lys Ile Met Asp His Arg Asn Ser Leu Thr Phe Pro Pro Glu Val
240                 245                 250                 255

GAA ATA AGC CAA TAT GCC CGA TCT TTG ATA CAA GGA TTT TTA ACA GAC       817
Glu Ile Ser Gln Tyr Ala Arg Ser Leu Ile Gln Gly Phe Leu Thr Asp
                260                 265                 270

AGA ACA CAG CGT TTA GGC AGA AAT GAA GTG GAA GAA ATT AAA CGA CAT       865
Arg Thr Gln Arg Leu Gly Arg Asn Glu Val Glu Glu Ile Lys Arg His
            275                 280                 285

CCA TTT TTC ATA AAT GAT CAA TGG ACT TTT GAC AAT TTA AGA GAC TCT       913
Pro Phe Phe Ile Asn Asp Gln Trp Thr Phe Asp Asn Leu Arg Asp Ser
        290                 295                 300

GCC CCA CCT GTA GTG CCA GAG CTG AGT GGT GAT GAT GAT ACA AGG AAC       961
Ala Pro Pro Val Val Pro Glu Leu Ser Gly Asp Asp Asp Thr Arg Asn
    305                 310                 315
```

-continued

```
TTT GAT GAT ATT GAA CGT GAT GAA ACA CCT GAA GAG AAT TTT CCT ATA     1009
Phe Asp Asp Ile Glu Arg Asp Glu Thr Pro Glu Glu Asn Phe Pro Ile
320                 325                 330                 335

CCA AAA ACT TTT GCT GGT AAT CAT CTG CCA TTT GTT GGA TTC ACA TAT     1057
Pro Lys Thr Phe Ala Gly Asn His Leu Pro Phe Val Gly Phe Thr Tyr
                340                 345                 350

AAT GGT GAT TAC CAA TTA TTA ACA AAT GGA GGT GTT AGA AAT AGT GAT     1105
Asn Gly Asp Tyr Gln Leu Leu Thr Asn Gly Gly Val Arg Asn Ser Asp
            355                 360                 365

ATG GTT GAT ACA AAA TTA AAC AAC ATT TGT GTT TCA AGT AAG GAT GAT     1153
Met Val Asp Thr Lys Leu Asn Asn Ile Cys Val Ser Ser Lys Asp Asp
        370                 375                 380

GTG TTA AAT TTA CAA AAT TTA TTA GAA CAA GAG AAA GGT AAC AGT GAA     1201
Val Leu Asn Leu Gln Asn Leu Leu Glu Gln Glu Lys Gly Asn Ser Glu
    385                 390                 395

AAT TTG AAA ACA AAC ACC CAA TTA TTA AGT AAT AAA TTA GAT GAA CTA     1249
Asn Leu Lys Thr Asn Thr Gln Leu Leu Ser Asn Lys Leu Asp Glu Leu
400                 405                 410                 415

GGT CAG AGA GAA TGT GAA TTA AGG AAT CAG GCT GGA GAT TAT GAG AAA     1297
Gly Gln Arg Glu Cys Glu Leu Arg Asn Gln Ala Gly Asp Tyr Glu Lys
                420                 425                 430

GAA TTG ACT AAA TTC AAA TTA TCG TGC AAA GAA TTA CAA CGT AAG GCA     1345
Glu Leu Thr Lys Phe Lys Leu Ser Cys Lys Glu Leu Gln Arg Lys Ala
            435                 440                 445

GAA TTT GAG AAT GAA TTA CGG CGT AAA ACT GAG TCC TTA CTA GTT GAA     1393
Glu Phe Glu Asn Glu Leu Arg Arg Lys Thr Glu Ser Leu Leu Val Glu
        450                 455                 460

ACA AAG AAA AGA CTA GAC GAA GAG CAG AAT AAA AGA ACT AGA GAA ATG     1441
Thr Lys Lys Arg Leu Asp Glu Glu Gln Asn Lys Arg Thr Arg Glu Met
    465                 470                 475

AAT AAT AAT CAA CAG CAC AAT GAC AAA ATA AAT ATG TTA GAA AAA CAA     1489
Asn Asn Asn Gln Gln His Asn Asp Lys Ile Asn Met Leu Glu Lys Gln
480                 485                 490                 495

ATT AAT GAT TTA CAA GAA AAA TTG AAA GGT GAA TTA GAG CAC AAT CAG     1537
Ile Asn Asp Leu Gln Glu Lys Leu Lys Gly Glu Leu Glu His Asn Gln
                500                 505                 510

AAA TTA AAG AAG CAA GCT GTT GAG CTT AGA GTT GCT CAG TCT GCT ACT     1585
Lys Leu Lys Lys Gln Ala Val Glu Leu Arg Val Ala Gln Ser Ala Thr
            515                 520                 525

GAA CAA CTG AAT AAT GAA TTA CAG GAA ACT ATG CAG GGT TTA CAA ACA     1633
Glu Gln Leu Asn Asn Glu Leu Gln Glu Thr Met Gln Gly Leu Gln Thr
        530                 535                 540

CAA AGA GAT GCT TTA CAA CAA GAA GTA GCA TCT CTC CAA GGC AAA CTT     1681
Gln Arg Asp Ala Leu Gln Gln Glu Val Ala Ser Leu Gln Gly Lys Leu
    545                 550                 555

TCT CAA GAG AGG AGC TCT AGA TCA CAG GCT TCT GAT ATG CAG ATA GAA     1729
Ser Gln Glu Arg Ser Ser Arg Ser Gln Ala Ser Asp Met Gln Ile Glu
560                 565                 570                 575

CTA GAA GCA AAA TTG CAG GCT CTC CAT ATT GAA CTG GAG CAT GTC AGA     1777
Leu Glu Ala Lys Leu Gln Ala Leu His Ile Glu Leu Glu His Val Arg
                580                 585                 590

AAT TGT GAA GAC AAA GTT ACC CAA GAC AAC AGA CAA CTA TTG GAA AGG     1825
Asn Cys Glu Asp Lys Val Thr Gln Asp Asn Arg Gln Leu Leu Glu Arg
            595                 600                 605

ATA TCA ACA TTG GAG AAA GAA TGT GCT TCT CTA GAA TTA GAA TTG AAA     1873
Ile Ser Thr Leu Glu Lys Glu Cys Ala Ser Leu Glu Leu Glu Lue Lys
        610                 615                 620

GCA ACA CAA AAC AAA TAT GAG CAA GAG GTC AAA GCA CAT CGC GAA ACT     1921
Ala Thr Gln Asn Lys Tyr Glu Gln Glu Val Lys Ala His Arg Glu Thr
```

-continued

```
    625                 630                 635

GAA AAA TCA AGA CTG GTC AGT AAA GAA GAA GCA AAT ATG GAG GAA GTT     1969
Glu Lys Ser Arg Leu Val Ser Lys Glu Glu Ala Asn Met Glu Glu Val
640                 645                 650                 655

AAA GCA CTC CAA ATA AAA TTA AAT GAA GAG AAA TCT GCT CGA CAG AAA     2017
Lys Ala Leu Gln Ile Lys Leu Asn Glu Glu Lys Ser Ala Arg Gln Lys
                660                 665                 670

TCT GAT CAG AAT TCT CAA GAA AAG GAA CGA CAA ATT TCT ATG TTA TCT     2065
Ser Asp Gln Asn Ser Gln Glu Lys Glu Arg Gln Ile Ser Met Leu Ser
            675                 680                 685

GTG GAT TAT CGT CAA ATC CAA CAG CGT TTG CAA AAG CTA GAA GGA GAA     2113
Val Asp Tyr Arg Gln Ile Gln Gln Arg Leu Gln Lys Leu Glu Gly Glu
        690                 695                 700

TAT AGG CAA GAG AGT GAA AAA GTT AAA GCT CTC CAC AGT CAG ATT GAG     2161
Tyr Arg Gln Glu Ser Glu Lys Val Lys Ala Leu His Ser Gln Ile Glu
    705                 710                 715

CAA GAG CAA CTA AAA AAA TCA CAA TTA CAA AGC GAA TTG GGT GTT CAA     2209
Gln Glu Gln Leu Lys Lys Ser Gln Leu Gln Ser Glu Leu Gly Val Gln
720                 725                 730                 735

AGG TCT CAG ACT GCA CAT TTA ACA GCC AGG GAA GCT CAG CTA GTT GGA     2257
Arg Ser Gln Thr Ala His Leu Thr Ala Arg Glu Ala Gln Leu Val Gly
                740                 745                 750

GAA GTT GCT CAT CTT AGA GAT GCT AAA AGA AAT GTT GAA GAA GAG TTA     2305
Glu Val Ala His Leu Arg Asp Ala Lys Arg Asn Val Glu Glu Glu Leu
            755                 760                 765

CAC AAG TTA AAA ACT GCT CGA TCA GTG GAT AAT GCT CAG ATG AAA GAG     2353
His Lys Leu Lys Thr Ala Arg Ser Val Asp Asn Ala Gln Met Lys Glu
        770                 775                 780

CTT CAA GAA CAA GTT GAA GCC GAG CAA GTT TTC TCG ACT CTT TAT AAA     2401
Leu Gln Glu Gln Val Glu Ala Glu Gln Val Phe Ser Thr Leu Tyr Lys
    785                 790                 795

ACA CAT TCT AAT GAA CTT AAG GAA GAA CTT GAG GAA AAA TCT CGT CAT     2449
Thr His Ser Asn Glu Leu Lys Glu Glu Leu Glu Glu Lys Ser Arg His
800                 805                 810                 815

ATT CAA GAA ATG GAA GAA GAA AGA GAA AGT TTG GTT CAT CAG CTA CAA     2497
Ile Gln Glu Met Glu Glu Glu Arg Glu Ser Leu Val His Gln Leu Gln
                820                 825                 830

ATT GCA TTA GCT AGA GCT GAT TCA GAG GCA TTG GCG AGA TCA ATA GCT     2545
Ile Ala Leu Ala Arg Ala Asp Ser Glu Ala Leu Ala Arg Ser Ile Ala
            835                 840                 845

GAT GAA AGT ATA GCT GAT TTA GAA AAG GAA AAG ACT ATG AAG GAA TTA     2593
Asp Glu Ser Ile Ala Asp Leu Glu Lys Glu Lys Thr Met Lys Glu Leu
        850                 855                 860

GAA CTA AAA GAA TTA TTA AAC AAA AAT CGT ACT GAA CTT TCC CAG AAA     2641
Glu Leu Lys Glu Leu Leu Asn Lys Asn Arg Thr Glu Leu Ser Gln Lys
    865                 870                 875

GAC ATT TCA ATA AGT GCA TTG CGT GAA CGA GAA AAT GAA CAG AAG AAA     2689
Asp Ile Ser Ile Ser Ala Leu Arg Glu Arg Glu Asn Glu Gln Lys Lys
880                 885                 890                 895

CTT TTA GAA CAA ATC  TC                                             2706
Leu Leu Glu Gln Ile
                900
```

(2) INFORMATION FOR SEQ ID NO: 21:

(i) SEQUENCE CHARACTERISTICS:
(A) LENGTH: 900 amino acids
(B) TYPE: amino acid
(D) TOPOLOGY: linear (ii) MOLECULE TYPE: protein (xi) SEQUENCE DESCRIPTION: SEQ ID NO: 21:

```
Met Lys Ser Ile Glu Ala Tyr Thr Asn Arg Tyr Glu Ile Ile Ala Ser
  1               5                  10                  15

Glu Ile Val Asn Leu Arg Met Lys Pro Asp Asp Phe Asn Leu Ile Lys
             20                  25                  30

Val Ile Gly Arg Gly Ala Phe Gly Glu Val Gln Leu Val Arg His Lys
         35                  40                  45

Ser Thr Ala Gln Val Phe Ala Met Lys Arg Leu Ser Lys Phe Glu Met
     50                  55                  60

Ile Lys Arg Pro Asp Ser Ala Phe Phe Trp Glu Glu Arg His Ile Met
 65                  70                  75                  80

Ala His Ala Lys Ser Glu Trp Ile Val Gln Leu His Phe Ala Phe Gln
                 85                  90                  95

Asp Gln Lys Tyr Leu Tyr Met Val Met Asp Tyr Met Pro Gly Gly Asp
            100                 105                 110

Leu Val Ser Leu Met Ser Asp Tyr Glu Ile Pro Glu Lys Trp Ala Met
        115                 120                 125

Phe Tyr Thr Met Glu Val Val Leu Ala Leu Asp Thr Ile His Ser Met
    130                 135                 140

Gly Phe Val His Arg Asp Val Lys Pro Asp Asn Met Leu Leu Asp Lys
145                 150                 155                 160

Tyr Gly His Leu Lys Leu Ala Asp Phe Gly Thr Cys Met Lys Met Asp
                165                 170                 175

Thr Asp Gly Leu Val Arg Ser Asn Asn Ala Val Gly Thr Pro Asp Tyr
            180                 185                 190

Ile Ser Pro Glu Val Leu Gln Ser Gln Gly Gly Glu Gly Val Tyr Gly
        195                 200                 205

Arg Glu Cys Asp Trp Trp Ser Val Gly Ile Phe Leu Tyr Glu Met Leu
    210                 215                 220

Phe Gly Glu Thr Pro Phe Tyr Ala Asp Ser Leu Val Gly Thr Tyr Ser
225                 230                 235                 240

Lys Ile Met Asp His Arg Asn Ser Leu Thr Phe Pro Pro Glu Val Glu
                245                 250                 255

Ile Ser Gln Tyr Ala Arg Ser Leu Ile Gln Gly Phe Leu Thr Asp Arg
            260                 265                 270

Thr Gln Arg Leu Gly Arg Asn Glu Val Glu Glu Ile Lys Arg His Pro
        275                 280                 285

Phe Phe Ile Asn Asp Gln Trp Thr Phe Asp Asn Leu Arg Asp Ser Ala
    290                 295                 300

Pro Pro Val Val Pro Glu Leu Ser Gly Asp Asp Asp Thr Arg Asn Phe
305                 310                 315                 320

Asp Asp Ile Glu Arg Asp Glu Thr Pro Glu Glu Asn Phe Pro Ile Pro
                325                 330                 335

Lys Thr Phe Ala Gly Asn His Leu Pro Phe Val Gly Phe Thr Tyr Asn
            340                 345                 350

Gly Asp Tyr Gln Leu Leu Thr Asn Gly Gly Val Arg Asn Ser Asp Met
        355                 360                 365

Val Asp Thr Lys Leu Asn Asn Ile Cys Val Ser Ser Lys Asp Asp Val
    370                 375                 380

Leu Asn Leu Gln Asn Leu Leu Glu Gln Glu Lys Gly Asn Ser Glu Asn
385                 390                 395                 400

Leu Lys Thr Asn Thr Gln Leu Leu Ser Asn Lys Leu Asp Glu Lys Glu
```

-continued

```
                405                 410                 415

Gln Arg Glu Cys Glu Leu Arg Asn Gln Ala Gly Asp Tyr Glu Lys Glu
            420                 425                 430

Leu Thr Lys Phe Lys Leu Ser Cys Lys Glu Leu Gln Arg Lys Ala Glu
        435                 440                 445

Phe Glu Asn Glu Leu Arg Arg Lys Thr Glu Ser Leu Leu Val Glu Thr
    450                 455                 460

Lys Lys Arg Leu Asp Glu Glu Gln Asn Lys Arg Thr Arg Glu Met Asn
465                 470                 475                 480

Asn Asn Gln Gln His Asn Asp Lys Ile Asn Met Leu Glu Lys Gln Ile
                485                 490                 495

Asn Asp Leu Gln Glu Lys Leu Lys Gly Glu Leu Glu His Asn Gln Lys
            500                 505                 510

Leu Lys Lys Gln Ala Val Glu Leu Arg Val Ala Gln Ser Ala Thr Glu
        515                 520                 525

Gln Leu Asn Asn Glu Leu Gln Glu Thr Met Gln Gly Leu Gln Thr Glu
    530                 535                 540

Arg Asp Ala Leu Gln Gln Glu Val Ala Ser Leu Gln Gly Lys Leu Ser
545                 550                 555                 560

Gln Glu Arg Ser Ser Arg Ser Gln Ala Ser Asp Met Gln Ile Glu Leu
                565                 570                 575

Glu Ala Lys Leu Gln Ala Leu His Ile Glu Leu Glu His Val Arg Asn
            580                 585                 590

Cys Glu Asp Lys Val Thr Gln Asp Asn Arg Gln Leu Leu Glu Arg Ile
        595                 600                 605

Ser Thr Leu Glu Lys Glu Cys Ala Ser Leu Glu Leu Glu Leu Lys Ala
    610                 615                 620

Thr Gln Asn Lys Tyr Glu Gln Glu Val Lys Ala His Arg Glu Thr Glu
625                 630                 635                 640

Lys Ser Arg Leu Val Ser Lys Glu Glu Ala Asn Met Glu Glu Val Lys
                645                 650                 655

Ala Leu Gln Ile Lys Leu Asn Glu Glu Lys Ser Ala Arg Gln Lys Ser
            660                 665                 670

Asp Gln Asn Ser Gln Glu Lys Glu Arg Gln Ile Ser Met Leu Ser Val
        675                 680                 685

Asp Tyr Arg Gln Ile Gln Gln Arg Leu Gln Lys Leu Glu Gly Glu Tyr
    690                 695                 700

Arg Gln Glu Ser Glu Lys Val Lys Ala Leu His Ser Gln Ile Glu Gln
705                 710                 715                 720

Glu Gln Leu Lys Lys Ser Gln Leu Gln Ser Glu Leu Gly Val Gln Arg
                725                 730                 735

Ser Gln Thr Ala His Leu Thr Ala Arg Glu Ala Gln Leu Val Gly Glu
            740                 745                 750

Val Ala His Leu Arg Asp Ala Lys Arg Asn Val Glu Glu Glu Leu His
        755                 760                 765

Lys Leu Lys Thr Ala Arg Ser Val Asp Asn Ala Gln Met Lys Glu Leu
    770                 775                 780

Gln Glu Gln Val Glu Ala Glu Gln Val Phe Ser Thr Leu Tyr Leu Thr
785                 790                 795                 800

His Ser Asn Glu Leu Lys Glu Glu Leu Glu Glu Lys Ser Arg His Ile
                805                 810                 815

Gln Glu Met Glu Glu Glu Arg Glu Ser Leu Val His Gln Leu Gln Ile
            820                 825                 830
```

```
Ala Leu Ala Arg Ala Asp Ser Glu Ala Leu Ala Arg Ser Ile Ala Asp
        835                 840                 845

Glu Ser Ile Ala Asp Leu Glu Lys Glu Lys Thr Met Lys Glu Leu Glu
    850                 855                 860

Leu Lys Glu Leu Leu Asn Lys Asn Arg Thr Glu Leu Ser Gln Lys Asp
865                 870                 875                 880

Ile Ser Ile Ser Ala Leu Arg Glu Arg Glu Asn Glu Gln Lys Lys Leu
                885                 890                 895

Leu Glu Gln Ile
            900
```

(2) INFORMATION FOR SEQ ID NO: 22:

(i) SEQUENCE CHARACTERISTICS:
(A) LENGTH: 414 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 3..414

(xi) SEQUENCE DESCRIPTION: SEQ ID NO: 22:

```
GA GCT GAT GAG AAT GGA AAT GTG ATT AGC ATT ACT GAT GAA AAT GGA         47
   Ala Asp Glu Asn Gly Asn Val Ile Ser Ile Thr Asp Glu Asn Gly
     1               5                  10                  15

AAC ATT ATT AGT ACT ACT GAT GAG AAT GGA AAT GTG ATT AGC ATT ACT        95
Asn Ile Ile Ser Thr Thr Asp Glu Asn Gly Asn Val Ile Ser Ile Thr
                 20                  25                  30

GAT GAG AAT GGA AAC ATT ATT AGT ACT ACT GAT GAG AAT GGA AAT GTG       143
Asp Glu Asn Gly Asn Ile Ile Ser Thr Thr Asp Glu Asn Gly Asn Val
             35                  40                  45

ATT AGC ATT ACT GAT GAA AAT GGA AAC ATT ATT AGT ACT ACT GAT GAG       191
Ile Ser Ile Thr Asp Glu Asn Gly Asn Ile Ile Ser Thr Thr Asp Glu
         50                  55                  60

AAT GGA AAT GTG ATT AGC ATT ACT GAT GAG AAT GGA AAT GTG ATT AAT       239
Asn Gly Asn Val Ile Ser Ile Thr Asp Glu Asn Gly Asn Val Ile Ser
     65                  70                  75

ATT ACT GAT GAA AAT GGA AAC TCG AAT AGC ACT ACT AGT GTT TTC AAT       287
Ile Thr Asp Glu Asn Gly Asn Ser Asn Ser Thr Thr Ser Val Phe Asn
 80                  85                  90                  95

GAA ACT GAA AAT ATG ACT GGT GCT GCT GAT ACA AAT GAA TAT TCA ATT       335
Glu Thr Glu Asn Met Thr Gly Ala Ala Asp Thr Asn Glu Tyr Ser Ile
                100                 105                 110

GGT TCT ACT GAC GGA AAT GGA AAT TTT ATA AGT ACT TTT AGT GAT CAT       383
Gly Ser Thr Asp Gly Asn Gly Asn Phe Ile Ser Thr Phe Ser Asp His
            115                 120                 125

GAT TAC GTA AGT AAT ACT GAA GAA AAT GAA  A                            414
Asp Tyr Val Ser Asn Thr Glu Glu Asn Glu
        130                 135
```

(2) INFORMATION FOR SEQ ID NO: 23:

(i) SEQUENCE CHARACTERISTICS:
(A) LENGTH: 137 amino acids
(B) TYPE: amino acid
(D) TOPOLOGY: linear (ii) MOLECULE TYPE: protein -continued (xi) SEQUENCE DESCRIPTION: SEQ ID NO: 23:

```
Ala Asp Glu Asn Gly Asn Val Ile Ser Ile Thr Asp Glu Asn Gly Asn
  1               5                  10                  15

Ile Ile Ser Thr Thr Asp Glu Asn Gly Asn Val Ile Ser Ile Thr Asp
             20                  25                  30

Glu Asn Gly Asn Ile Ile Ser Thr Thr Asp Glu Asn Gly Asn Val Ile
         35                  40                  45

Ser Ile Thr Asp Glu Asn Gly Asn Ile Ile Ser Thr Thr Asp Glu Asn
     50                  55                  60

Gly Asn Val Ile Ser Ile Thr Asp Glu Asn Gly Asn Val Ile Ser Ile
 65                  70                  75                  80

Thr Asp Glu Asn Gly Asn Ser Asn Ser Thr Thr Ser Val Phe Asn Glu
                 85                  90                  95

Thr Glu Asn Met Thr Gly Ala Ala Asp Thr Asn Glu Tyr Ser Ile Gly
            100                 105                 110

Ser Thr Asp Gly Asn Gly Asn Phe Ile Ser Thr Phe Ser Asp His Asp
        115                 120                 125

Tyr Val Ser Asn Thr Glu Glu Asn Glu
    130                 135
```

(2) INFORMATION FOR SEQ ID NO: 24:

(i) SEQUENCE CHARACTERISTICS:
(A) LENGTH: 273 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 3..273

(xi) SEQUENCE DESCRIPTION: SEQ ID NO: 24:

```
AT GAG AAT GGA AAT GTG ATT AGC TAT ACT GAT GAA AAT GGA AAC ATT         47
   Glu Asn Gly Asn Val Ile Ser Tyr Thr Asp Glu Asn Gly Asn Ile
     1               5                  10                  15

ATC AGT ACT ACT GAT GAG AAT GGA AAT GTG ATT AGC ATT ACT GAT GAA        95
Ile Ser Thr Thr Asp Glu Asn Gly Asn Val Ile Ser Ile Thr Asp Glu
                 20                  25                  30

AAT GGA AAT GTG ATT AGC ATT ACT GAT GAA AAT GGA AAC ATT ATC AGT       143
Asn Gly Asn Val Ile Ser Ile Thr Asp Glu Asn Gly Asn Ile Ile Ser
             35                  40                  45

ACT ACT GAT GAG AAT GGA AAT GTG ATT AGC ATT ACT GAT GAA AAT GGA       191
Thr Thr Asp Glu Asn Gly Asn Val Ile Ser Ile Thr Asp Glu Asn Gly
         50                  55                  60

AAT GTG ATT AGC ATT ACT GAT GAA AAT GGA AAC ATT ATT AGT ACT ACT       239
Asn Val Ile Ser Ile Thr Asp Glu Asn Gly Asn Ile Ile Ser Thr Thr
     65                  70                  75

GAT GAG AAT GGA AAT GTG ATT AGC AAT ACT CGA  G                        273
Asp Glu Asn Gly Asn Val Ile Ser Asn Thr Arg
 80                  85                  90
```

(2) INFORMATION FOR SEQ ID NO: 25:

(i) SEQUENCE CHARACTERISTICS:
(A) LENGTH: 90 amino acids
(B) TYPE: amino acid
(D) TOPOLOGY: linear (ii) MOLECULE TYPE: protein -continued (xi) SEQUENCE DESCRIPTION: SEQ ID NO: 25:

```
Glu Asn Gly Asn Val Ile Ser Tyr Thr Asp Glu Asn Gly Asn Ile Ile
  1               5                  10                  15

Ser Thr Thr Asp Glu Asn Gly Asn Val Ile Ser Ile Thr Asp Glu Asn
             20                  25                  30

Gly Asn Val Ile Ser Ile Thr Asp Glu Asn Gly Asn Ile Ile Ser Thr
         35                  40                  45

Thr Asp Glu Asn Gly Asn Val Ile Ser Ile Thr Asp Glu Asn Gly Asn
     50                  55                  60

Val Ile Ser Ile Thr Asp Glu Asn Gly Asn Ile Ile Ser Thr Thr Asp
 65                  70                  75                  80

Glu Asn Gly Asn Val Ile Ser Asn Thr Arg
                 85                  90
```

(2) INFORMATION FOR SEQ ID NO: 26:

(i) SEQUENCE CHARACTERISTICS:
(A) LENGTH: 1704 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 24..1406

(xi) SEQUENCE DESCRIPTION: SEQ ID NO: 26:

```
CAGAAACCCG ACATTCTCAA AAT ATG GAA CCT CAA TCG CTG TCT TGG CAA         50
                          Met Glu Pro Gln Ser Leu Ser Trp Gln
                            1               5

CTT CCG ACT CAA GTA GTT CAG CCA GTT TTT GAA CAA CAA ATG CAG ATT       98
Leu Pro Thr Gln Val Val Gln Pro Val Phe Glu Gln Gln Met Gln Ile
 10                  15                  20                  25

CCT GGA TAT AAT ATG CAA ATT CAA TCT AAT TAT TAT CAA ATT CAC CCA      146
Pro Gly Tyr Asn Met Gln Ile Gln Ser Asn Tyr Tyr Gln Ile His Pro
                 30                  35                  40

GAA ATG TTG GAT CCA AAT TTG AAC AAT CCT CAG CAG TTA ATG TTT AAT      194
Glu Met Leu Asp Pro Asn Leu Asn Asn Pro Gln Gln Leu Met Phe Asn
             45                  50                  55

TAT ATG CAA TTA CAA CAA TTG CAG GAA CTA CAA CAT TTA AGT CAA CAA      242
Tyr Met Gln Leu Gln Gln Leu Gln Glu Leu Gln His Leu Ser Gln Gln
         60                  65                  70

CAG CCA ATG CAT CAT GAA TTT GAA CAT CAT ATC CCC ATT CCA CAA GAA      290
Gln Pro Met His His Glu Phe Glu His His Ile Pro Ile Pro Gln Glu
     75                  80                  85

GCA ACT TCA ACT AAT TAC GGT CCA TCC GGA CAG TAT ATT ACT AGT GAC      338
Ala Thr Ser Thr Asn Tyr Gly Pro Ser Gly Gln Tyr Ile Thr Ser Asp
 90                  95                 100                 105

GCA ACA TCT TAT CAA TCA ATT GCC CAA CAA TTT GTA CCA CAA CCA CCA      386
Ala Thr Ser Tyr Gln Ser Ile Ala Gln Gln Phe Val Pro Gln Pro Pro
                110                 115                 120

ATT GAA ACT ACC ACC ACG AAA ATA CCT GAA ACT GAA ATT CAA ATT GGC      434
Ile Glu Thr Thr Thr Thr Lys Ile Pro Glu Thr Glu Ile Gln Ile Ser
            125                 130                 135

GTT TCG AAT CAA TAT GCC CAA AAT ATA ACT TAT AAT TCA AAT ATC AGT      482
Val Ser Asn Gln Tyr Ala Gln Asn Ile Thr Tyr Asn Ser Asn Ile Ser
        140                 145                 150

CCT GAA GTG ATT GGA TTC CGA GAA CAT TAT GTT GCG GAA CAG CCT TCT      530
```

-continued

```
Pro Glu Val Ile Gly Phe Arg Glu His Tyr Val Ala Glu Gln Pro Ser
    155                 160                 165

GGT GAC GTG CTT CAC AAA AGT CAT TTA ACA GAA CAA CCA GCA GAT AAA      578
Gly Asp Val Leu His Lys Ser His Leu Thr Glu Gln Pro Ala Asp Lys
170                 175                 180                 185

AGC ACA CGT GGT GAT CAG GAA CCT GTT AGT GAG ACA GGC TCT GGT TTT      626
Ser Thr Arg Gly Asp Gln Glu Pro Val Ser Glu Thr Gly Ser Gly Phe
                190                 195                 200

TCG TAT GCA CAA ATT TTA TCA CAG GGA CTT AAG CCT ACC CAG CCA TCC      674
Ser Tyr Ala Gln Ile Leu Ser Gln Gly Leu Lys Pro Thr Gln Pro Ser
            205                 210                 215

AAC TCA GTT AAT TTG CTT GCA GAT CGA TCG AGA TCA CCT CTA GAT ACG      722
Asn Ser Val Asn Leu Leu Ala Asp Arg Ser Arg Ser Pro Leu Asp Thr
        220                 225                 230

AAA ACG AAA GAA AAT TAT AAA TCT CCT GGT CGT GTG CAG GAT ATC ACG      770
Lys Thr Lys Glu Asn Tyr Lys Ser Pro Gly Arg Val Gln Asp Ile Thr
    235                 240                 245

AAA ATA ATA GAT GAG AAA CAA AAG TCG TCA AAA GAC ACA GAG TGG CAT      818
Lys Ile Ile Asp Glu Lys Gln Lys Ser Ser Lys Asp Thr Glu Trp His
250                 255                 260                 265

AAT AAG AAA GTG AAA GAA CAT AAA AAA GTG AAA GAT ATC AAA CCT GAT      866
Asn Lys Lys Val Lys Glu His Lys Lys Val Lys Asp Ile Lys Pro Asp
                270                 275                 280

TTC GAA TCT TCT CAA AGG AAT AAG AAA AGC AAG AAT ATT CCT AAG CAA      914
Phe Glu Ser Ser Gln Arg Asn Lys Lys Ser Lys Asn Ile Pro Leu Thr
            285                 290                 295

ATT GAA AAT ATC ACA CCT CAA CTT GAC AGC TTA CGA TCA CGA GAT ATA      962
Ile Glu Asn Ile Thr Pro Gln Leu Asp Ser Leu Arg Ser Arg Asp Ile
        300                 305                 310

GTA ATT AAG GGA GAA TTA CTA ACA AAA GAT ACT ACA AAA AGT TTA ACT     1010
Val Ile Lys Gly Glu Leu Leu Thr Lys Asp Thr Thr Lys Ser Leu Thr
    315                 320                 325

ACT GTT AAT GTT GAT AGT GAA TTA GAT AGT GTA AAA CCT AAA GAT GAA     1058
Thr Val Asn Val Asp Ser Glu Leu Asp Ser Val Lys Pro Lys Asp Glu
330                 335                 340                 345

AAA CCT GAA CCT TCT GAA CCT AGT AAA ACG TTT ATT GAT ACT TCA GTT     1106
Lys Pro Glu Pro Ser Glu Pro Ser Lys Thr Phe Ile Asp Thr Ser Val
                350                 355                 360

GCA AAG GAT GTT GAT AAT TCT ACA CAG GCG AAC CAT AAA AAG AAG AAA     1154
Ala Lys Asp Val Asp Asn Ser Thr Gln Ala Asn His Lys Lys Lys Lys
            365                 370                 375

AGT AAA TCT AAG CCG AGG AAA ACG GAA CCG GAA GAT GAA ATT GAA AAA     1202
Ser Lys Ser Lys Pro Arg Lys Thr Glu Pro Glu Asp Glu Ile Glu Lys
        380                 385                 390

GCT TTG AAA GAA ATT CAA GCT AGT GAG AAA AAA CTT ACG AAG TCT ATC     1250
Ala Leu Lys Glu Ile Gln Ala Ser Glu Lys Lys Leu Thr Lys Ser Ile
    395                 400                 405

GAT AAC ATT GTG AAT AAA TTT AAT ACA CCA CTT GCT AGT GTT AAA GCC     1298
Asp Asn Ile Val Asn Lys Phe Asn Thr Pro Leu Ala Ser Val Lys Ala
410                 415                 420                 425

GAT GAT TCC AAT TCT ACC AAG GAT AAT GTA CCA GCA AAG AAG AAA AAA     1346
Asp Asp Ser Asn Ser Thr Lys Asp Asn Val Pro Ala Lys Lys Lus Lys
                430                 435                 440

CCT TCG AAG TCA TCT GTT TCT TTA CCT GAG AAT GTA GTA CAA AAT CTA     1394
Pro Ser Lys Ser Ser Val Ser Leu Pro Glu Asn Val Val Gln Asn Leu
            445                 450                 455

TTG ATA CTA ACA TAA CTACTAGTAG CGACAAGATT GAAAACATGC CGCAACCGCA     1449
Leu Ile Leu Thr
        460
```

-continued

```
ACCAAAAAGA GAAGATTTAC AAGATGCAGC TAAGGAAGTA TTGACTTCAA TAGAGTCAGT   1509

AATGATGCAG TCTGTTGAGA CTATTCCTAT TACGAAGAAA AGAGTAAATA AGAAAAAGAA   1569

TACCACTCAA CAGACGAAGG AATTTGTGGA ACACGAAATA TGCGATACAT CAAAAAATGA   1629

AACTTTAAAA AATATTGAAA AAGAATCGCA TGAGAATATG GCTATATTGC AAACAAGTCC   1689

GAAACCGCCA CTAAG                                                    1704
```

(2) INFORMATION FOR SEQ ID NO: 27:

(i) SEQUENCE CHARACTERISTICS:
(A) LENGTH: 461 amino acids
(B) TYPE: amino acid
(D) TOPOLOGY: linear (ii) MOLECULE TYPE: protein (xi) SEQUENCE DESCRIPTION: SEQ ID NO: 27:

```
Met Glu Pro Gln Ser Leu Ser Trp Gln Leu Pro Thr Gln Val Val Gln
  1               5                  10                  15

Pro Val Phe Glu Gln Gln Met Gln Ile Pro Gly Tyr Asn Met Gln Ile
             20                  25                  30

Gln Ser Asn Tyr Tyr Gln Ile His Pro Glu Met Leu Asp Pro Asn Leu
         35                  40                  45

Asn Asn Pro Gln Gln Leu Met Phe Asn Tyr Met Gln Leu Gln Gln Leu
     50                  55                  60

Gln Glu Leu Gln His Leu Ser Gln Gln Gln Pro Met His His Glu Phe
 65                  70                  75                  80

Glu His His Ile Pro Ile Pro Gln Glu Ala Thr Ser Thr Asn Tyr Gly
                 85                  90                  95

Pro Ser Gly Gln Tyr Ile Thr Ser Asp Ala Thr Ser Tyr Gln Ser Ile
            100                 105                 110

Ala Gln Gln Phe Val Pro Gln Pro Pro Ile Glu Thr Thr Thr Thr Lys
        115                 120                 125

Ile Pro Glu Thr Glu Ile Gln Ile Gly Val Ser Asn Gln Tyr Ala Gln
    130                 135                 140

Asn Ile Thr Tyr Asn Ser Asn Ile Ser Pro Glu Val Ile Gly Phe Arg
145                 150                 155                 160

Glu His Tyr Val Ala Glu Gln Pro Ser Gly Asp Val Leu His Lys Ser
                165                 170                 175

His Leu Thr Glu Gln Pro Ala Asp Lys Ser Thr Arg Gly Asp Gln Glu
            180                 185                 190

Pro Val Ser Glu Thr Gly Ser Gly Phe Ser Tyr Ala Gln Ile Leu Ser
        195                 200                 205

Gln Gly Leu Lys Pro Thr Gln Pro Ser Asn Ser Val Asn Leu Leu Ala
    210                 215                 220

Asp Arg Ser Arg Ser Pro Leu Asp Thr Lys Thr Lys Glu Asn Tyr Lys
225                 230                 235                 240

Ser Pro Gly Arg Val Gln Asp Ile Thr Lys Ile Ile Asp Glu Lys Gln
                245                 250                 255

Lys Ser Ser Lys Asp Thr Glu Trp His Asn Lys Lys Val Lys Glu His
            260                 265                 270

Lys Lys Val Lys Asp Ile Lys Pro Asp Phe Glu Ser Ser Gln Arg Asn
        275                 280                 285

Lys Lys Ser Lys Asn Ile Pro Lys Gln Ile Glu Asn Ile Thr Pro Gln
    290                 295                 300
```

-continued

```
Leu Asp Ser Leu Arg Ser Arg Asp Ile Val Ile Lys Gly Glu Leu Leu
305                 310                 315                 320

Thr Lys Asp Thr Thr Lys Ser Leu Thr Thr Val Asn Val Asp Ser Glu
                325                 330                 335

Leu Asp Ser Val Lys Pro Lys Asp Glu Lys Pro Glu Pro Ser Glu Pro
            340                 345                 350

Ser Lys Thr Phe Ile Asp Thr Ser Val Ala Lys Asp Val Asp Asn Ser
        355                 360                 365

Thr Gln Ala Asn His Lys Lys Lys Lys Ser Lys Ser Lys Pro Arg Lys
    370                 375                 380

Thr Glu Pro Glu Asp Glu Ile Glu Lys Ala Leu Lys Glu Ile Gln Ala
385                 390                 395                 400

Ser Glu Lys Lys Leu Thr Lys Ser Ile Asp Asn Ile Val Asn Lys Phe
                405                 410                 415

Asn Thr Pro Leu Ala Ser Val Lys Ala Asp Asp Ser Asn Ser Thr Lys
            420                 425                 430

Asp Asn Val Pro Ala Lys Lys Lys Lys Pro Ser Lys Ser Ser Val Ser
        435                 440                 445

Leu Pro Glu Asn Val Val Gln Asn Leu Leu Ile Leu Thr
    450                 455                 460
```

(2) INFORMATION FOR SEQ ID NO: 28:

(i) SEQUENCE CHARACTERISTICS:
(A) LENGTH: 1383 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 28:

```
ATGGAACCTC AATCGCTGTC TTGGCAACTT CCGACTCAAG TAGTTCAGCC AGTTTTTGA      60

CAACAAATGC AGATTCCTGG ATATAATATG CAAATTCAAT CTAATTATTA TCAAATTCAC    120

CCAGAAATGT TGGATCCAAA TTTGAACAAT CCTCAGCAGT TAATGTTTAA TTATATGCAA    180

TTACAACAAT TGCAGGAACT ACAACATTTA AGTCAACAAC AGCCAATGCA TCATGAATTT    240

GAACATCATA TCCCCATTCC ACAAGAAGCA ACTTCAACTA ATTACGGTCC ATCCGGACAG    300

TATATTACTA GTGACGCAAC ATCTTATCAA TCAATTGCCC AACAATTTGT ACCACAACCA    360

CCAATTGAAA CTACCACCAC GAAAATACCT GAAACTGAAA TTCAAATTGG CGTTTCGAAT    420

CAATATGCCC AAAATATAAC TTATAATTCA AATATCAGTC CTGAAGTGAT TGGATTCCGA    480

GAACATTATG TTGCGGAACA GCCTTCTGGT GACGTGCTTC ACAAAAGTCA TTTAACAGAA    540

CAACCAGCAG ATAAAAGCAC ACGTGGTGAT CAGGAACCTG TTAGTGAGAC AGGCTCTGGT    600

TTTTCGTATG CACAAATTTT ATCACAGGGA CTTAAGCCTA CCCAGCCATC CAACTCAGTT    660

AATTTGCTTG CAGATCGATC GAGATCACCT CTAGATACGA AAACGAAAGA AAATTATAAA    720

TCTCCTGGTC GTGTGCAGGA TATCACGAAA ATAATAGATG AGAAACAAAA GTCGTCAAAA    780

GACACAGAGT GGCATAATAA GAAAGTGAAA GAACATAAAA AAGTGAAAGA TATCAAACCT    840

GATTTCGAAT CTTCTCAAAG GAATAAGAAA AGCAAGAATA TTCCTAAGCA AATTGAAAAT    900

ATCACACCTC AACTTGACAG CTTACGATCA CGAGATATAG TAATTAAGGG AGAATTACTA    960

ACAAAAGATA CTACAAAAAG TTTAACTACT GTTAATGTTG ATAGTGAATT AGATAGTGTA   1020

AAACCTAAAG ATGAAAAACC TGAACCTTCT GAACCTAGTA AAACGTTTAT TGATACTTCA   1080
```

-continued

```
GTTGCAAAGG ATGTTGATAA TTCTACACAG GCGAACCATA AAAAGAAGAA AAGTAAATCT   1140

AAGCCGAGGA AAACGGAACC GGAAGATGAA ATTGAAAAAG CTTTGAAAGA AATTCAAGCT   1200

AGTGAGAAAA AACTTACGAA GTCTATCGAT AACATTGTGA ATAAATTTAA TACACCADTT   1260

GCTAGTGTTA AAGCCGATGA TTCCAATTCT ACCAAGGATA ATGTACCAGC AAAGAAGAAA   1320

AAACCTTCGA AGTCATCTGT TTCTTTACCT GAGAATGTAG TACAAAATCT ATTGATACTA   1380

ACA                                                                1383
```

(2) INFORMATION FOR SEQ ID NO: 29:

(i) SEQUENCE CHARACTERISTICS:
(A) LENGTH: 1758 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1...1758

(ix) FEATURE:
(A) NAME/KEY: W = A or T
(B) LOCATION: 1136

(xi) SEQUENCE DESCRIPTION: SEQ ID NO: 29:

```
CTA GAG ATG GCT AAA TTT CTG ACG GAA ACA TTA GAC GAC ATG ACT CTA       48
Leu Glu Met Ala Lys Phe Leu Thr Glu Thr Leu Asp Asp Met Thr Leu
  1               5                  10                  15

CAA CAC AAA GAT CAC AGA TCA GAA TTG GCT AAA GAG TTT TCA ATT TGG       96
Gln His Lys Asp His Arg Ser Glu Leu Ala Lys Glu Phe Ser Ile Trp
             20                  25                  30

TTT ACG AAA ATG AGA CAG TCT GGC GCT CAA GCC AGT AAC GAA GAA ATC      144
Phe Thr Lys Met Arg Gln Ser Gly Ala Gln Ala Ser Asn Glu Glu Glu
         35                  40                  45

ATG AAA TTT TCA AAA TTG TTT GAA GAT GAA ATC ACT CTT GAC TCG CTG      192
Met Lys Phe Ser Lys Leu Phe Glu Asp Glu Ile Thr Leu Asp Ser Leu
     50                  55                  60

GCG AGG CCG CAA CTT GTT GCT TTG TGC AGG GTA CTA GAA ATC AGT ACT      240
Ala Arg Pro Gln Leu Val Ala Leu Cys Arg Val Leu Glu Ile Ser Thr
 65                  70                  75                  80

TTA GGA ACA ACA AAT TTC TTA AGG TTT CAA CTG CGA ATG AAA CTG CGT      288
Leu Gly Thr Thr Asn Phe Leu Arg Phe Gln Leu Arg Met Lys Leu Arg
                 85                  90                  95

TCA TTA GCT GCT GAT GAT AAA ATG ATT CAA AAA GAA GGC ATA GTT TCT      336
Ser Leu Ala Ala Asp Asp Lys Met Ile Gln Lys Glu Gly Ile Val Ser
            100                 105                 110

ATG ACT TAT TCG GAG GTG CAA CAG GCC TGC AGA GCT CGT GGA ATG CGA      384
Met Thr Tyr Ser Glu Val Gln Gln Ala Cys Arg Ala Arg Gly Met Arg
        115                 120                 125

GCT TAT GGT ATG CCT GAA CAT AGG TTG AGG AGG CAA TTG GAA GAC TGG      432
Ala Tyr Gly Met Pro Glu His Arg Leu Arg Arg Gln Leu Glu Asp Trp
    130                 135                 140

ATT AAT TTA AGC TTG AAT GAA AAG GTT CCA CCA TCA TTA TTG CTT TTG      480
Ile Asn Leu Ser Leu Asn Glu Lys Val Pro Pro Ser Leu Leu Leu Leu
145                 150                 155                 160

TCA AGG GCG CTG ATG TTG CCC GAG AAT GTT CCA GTG TCT GAT AAA CTT      528
Ser Arg Ala Leu Met Leu Pro Glu Asn Val Pro Val Ser Asp Lys Leu
                165                 170                 175

AAA GCA ACA ATA AAT GCT CTT CCT GAA ACT ATT GTA ACT CAG ACA AAG      576
Lys Ala Thr Ile Asn Ala Leu Pro Glu Thr Ile Val Thr Gln Thr Lys
```

-continued

```
            180                 185                 190

GCT GCT ATT GGA GAA AGA GAA GGA AAG ATT GAC AAT AAG ACC AAA ATT      624
Ala Ala Ile Gly Glu Arg Glu Gly Lys Ile Asp Asn Lys Thr Lys Ile
        195                 200                 205

GAG GTC ATC AAA GAG GAA GAA CGC AAA ATT CGC GAA GAG CGC CAA GAA      672
Glu Val Ile Lys Glu Glu Glu Arg Lys Ile Arg Glu Glu Arg Gln Glu
    210                 215                 220

GCA CGT GAG GAA GAG GAA CAA CGC AAG CAA GCC GAA CTT GCT CTT AAT      720
Ala Arg Glu Glu Glu Glu Gln Arg Lys Gln Ala Glu Leu Ala Leu Asn
225                 230                 235                 240

GCC AGT TCT GCA GCA GCT GAG GCC TCT TCA GCT CAG GAA CTT TTG ATA      768
Ala Ser Ser Ala Ala Ala Glu Ala Ser Ser Ala Gln Glu Leu Leu Ile
                245                 250                 255

GAT ACA GCT CCT GTA ATA GAT GCA GAA AAG ACA CCA AAG GTG GCA ACA      816
Asp Thr Ala Pro Val Ile Asp Ala Glu Lys Thr Pro Lys Val Ala Thr
            260                 265                 270

TCA CCT GTT GAA TCA CCA TTG GCA CCA CCA GAA GTT CTG ATT ATG GGT      864
Ser Pro Val Glu Ser Pro Leu Ala Pro Pro Glu Val Leu Ile Met Gly
        275                 280                 285

GCT CCT AAA ACA CCT GTT GCA ACC GAA GTG GAT AAG AAT GCT GAT GAG      912
Ala Pro Lys Thr Pro Val Ala Thr Glu Val Asp Lys Asn Ala Asp Glu
    290                 295                 300

GTG GAA TTC ACC AAG AAA GAT CTT GAG GTT GTT GAA GAT GCA TTG GAT      960
Val Glu Phe Thr Lys Lys Asp Leu Glu Val Val Glu Asp Ala Leu Asp
305                 310                 315                 320

ACA CTA TCG AAA GAC AAA AAT AAT TTG GTG ATT GAA AAG GAA GTT ATT     1008
Thr Leu Ser Lys Asp Lys Asn Asn Leu Val Ile Glu Lys Glu Val Ile
                325                 330                 335

AAA GAC ATT AAG GAA GAA ATT GCT GAT TAC CAA GAA GAT GTA GAA GAA     1056
Lys Asp Ile Lys Glu Glu Ile Ala Asp Tyr Gln Glu Asp Val Glu Glu
            340                 345                 350

TTG AAA GAA GCC ATA GTT GCT GCT GAG AAA CCA AAG GAT GAG ATA AAA     1104
Leu Lys Glu Ala Ile Val Ala Ala Glu Lys Pro Lys Asp Glu Ile Lys
        355                 360                 365

GAA ACT AAA GGA GCT CAA CGA TTG TTG AAG AWG GTT AAC AAG ATG ATA     1152
Glu Thr Lys Gly Ala Gln Arg Leu Leu Lys Xaa Val Asn Lys Met Ile
    370                 375                 380

ACG AAA ATG GAT ACT GTT GTA CAA GAA ATT GAA AGC AAA GAA TCT GAG     1200
Thr Lys Met Asp Thr Val Val Gln Glu Ile Glu Ser Lys Glu Ser Glu
385                 390                 395                 400

AAG AAA GCC AAA ACA TTG CCA CTT GAA GCT CCT AGG AGC GCT ACT GAA     1248
Lys Lys Ala Lys Thr Leu Pro Leu Glu Ala Pro Arg Ser Ala Thr Glu
                405                 410                 415

ACT CAA GAA TTA GAT GTA AGG AAA GAA AGA GGA GAG ATT TTA ATT GAC     1296
Thr Gln Glu Leu Asp Val Arg Lys Glu Arg Gly Glu Ile Leu Ile Asp
            420                 425                 430

GAA TTA ATG GAC GCT ATT AAG AAA GTT AAA AAT GTG CCA GAC GAA AAT     1344
Glu Leu Met Asp Ala Ile Lys Lys Val Lys Asn Val Pro Asp Glu Asn
        435                 440                 445

CGC TTG AAA TTA ATT GAG AAC ATT TTG GGC AGG ATC GAT ACT GAC AAA     1392
Arg Leu Lys Leu Ile Glu Asn Ile Leu Gly Arg Ile Asp Thr Asp Lys
    450                 455                 460

GAT AGG CAT ATC AAA GTT GAA GAT GTA TTG AAG GTT ATT GAC ATT GTG     1440
Asp Arg His Ile Lys Val Glu Asp Val Leu Lys Val Ile Asp Ile Val
465                 470                 475                 480

GAA AAA GAA GAT GGT ATC ATG AGT ACA AAA CAA TTA GAT GAG TTG GTT     1488
Glu Lys Glu Asp Gly Ile Met Ser Thr Lys Gln Leu Asp Glu Leu Val
                485                 490                 495

CAG CTT TTG AAA AAG GAG GAA GTT ATT GAA TTG GAA GAA AAG AAA GAA     1536
```

-continued

```
Gln Leu Leu Lys Lys Glu Glu Val Ile Glu Leu Glu Glu Lys Lys Glu
            500                 505                 510

AAG CAA GAG TCT CAA CAG AAA AGT TTT GTA CCA CCA AGT GAA ACT TTG     1584
Lys Gln Glu Ser Gln Gln Lys Ser Phe Val Pro Pro Ser Glu Thr Leu
        515                 520                 525

CAT CTT GAA TCA TCA CAG CAG AAG AGT ACA GTT CCT AGC TCG GGA CAT     1632
His Leu Glu Ser Ser Gln Gln Lys Ser Thr Val Pro Ser Ser Gly His
    530                 535                 540

GAA GCT AAG GTG TCC GAA GAT GAC TTA AAT GTT AAA AAT AAA AAT TTG     1680
Glu Ala Lys Val Ser Glu Asp Asp Leu Asn Val Lys Asn Lys Asn Leu
545                 550                 555                 560

GAA GAA TCG ACC AAA ACT GAA TGT GGA GCA ATT GAC GAA GAG CAC AGA     1728
Glu Glu Ser Thr Lys Thr Glu Cys Gly Ala Ile Asp Glu Glu His Arg
                565                 570                 575

AGA GAG CAT TGC CAG TAC CCA GAC ATT ACA                             1758
Arg Glu His Cys Gln Tyr Pro Asp Ile Thr
            580                 585
```

(2) INFORMATION FOR SEQ ID NO: 30:

(i) SEQUENCE CHARACTERISTICS:
(A) LENGTH: 586 amino acids
(B) TYPE: amino acid
(D) TOPOLOGY: linear (ii) MOLECULE TYPE: protein (ix) FEATURE:
(A) NAME/KEY: Xaa = any amino acid
(B) LOCATION: 379

(xi) SEQUENCE DESCRIPTION: SEQ ID NO: 30:

```
Leu Glu Met Ala Lys Phe Leu Thr Glu Thr Leu Asp Asp Met Thr Leu
  1               5                  10                  15

Gln His Lys Asp His Arg Ser Glu Leu Ala Lys Glu Phe Ser Ile Trp
             20                  25                  30

Phe Thr Lys Met Arg Gln Ser Gly Ala Gln Ala Ser Asn Glu Glu Ile
        35                  40                  45

Met Lys Phe Ser Lys Leu Phe Glu Asp Glu Ile Thr Leu Asp Ser Leu
     50                  55                  60

Ala Arg Pro Gln Leu Val Ala Leu Cys Arg Val Leu Glu Ile Ser Thr
 65                  70                  75                  80

Leu Gly Thr Thr Asn Phe Leu Arg Phe Gln Leu Arg Met Lys Leu Arg
                 85                  90                  95

Ser Leu Ala Ala Asp Asp Lys Met Ile Gln Lys Glu Gly Ile Val Ser
            100                 105                 110

Met Thr Tyr Ser Glu Val Gln Gln Ala Cys Arg Ala Arg Gly Met Arg
        115                 120                 125

Ala Tyr Gly Met Pro Glu His Arg Leu Arg Arg Gln Leu Glu Asp Trp
    130                 135                 140

Ile Asn Leu Ser Leu Asn Glu Lys Val Pro Pro Ser Leu Leu Leu Leu
145                 150                 155                 160

Ser Arg Ala Leu Met Leu Pro Glu Asn Val Pro Val Ser Asp Lys Leu
                165                 170                 175

Lys Ala Thr Ile Asn Ala Leu Pro Glu Thr Ile Val Thr Gln Thr Lys
            180                 185                 190

Ala Ala Ile Gly Glu Arg Glu Gly Lys Ile Asp Asn Lys Thr Lys Ile
        195                 200                 205

Glu Val Ile Lys Glu Glu Glu Arg Lys Ile Arg Glu Glu Arg Gln Glu
```

```
    210                 215                 220

Ala Arg Glu Glu Glu Glu Gln Arg Lys Gln Ala Glu Leu Ala Leu Asn
225                 230                 235                 240

Ala Ser Ser Ala Ala Ala Glu Ala Ser Ser Ala Gln Glu Leu Leu Ile
                245                 250                 255

Asp Thr Ala Pro Val Ile Asp Ala Glu Lys Thr Pro Lys Val Ala Thr
            260                 265                 270

Ser Pro Val Glu Ser Pro Leu Ala Pro Pro Glu Val Leu Ile Met Gly
        275                 280                 285

Ala Pro Lys Thr Pro Val Ala Thr Glu Val Asp Lys Asn Ala Asp Glu
    290                 295                 300

Val Glu Phe Thr Lys Lys Asp Leu Glu Val Val Glu Asp Ala Leu Asp
305                 310                 315                 320

Thr Leu Ser Lys Asp Lys Asn Asn Leu Val Ile Glu Lys Glu Val Ile
                325                 330                 335

Lys Asp Ile Lys Glu Glu Ile Ala Asp Tyr Gln Glu Asp Val Glu Glu
            340                 345                 350

Leu Lys Glu Ala Ile Val Ala Ala Glu Lys Pro Lys Asp Glu Ile Lys
        355                 360                 365

Glu Thr Lys Gly Ala Gln Arg Leu Leu Lys Xaa Val Asn Lys Met Ile
    370                 375                 380

Thr Lys Met Asp Thr Val Val Gln Glu Ile Glu Ser Lys Glu Ser Glu
385                 390                 395                 400

Lys Lys Ala Lys Thr Leu Pro Leu Glu Ala Pro Arg Ser Ala Thr Glu
                405                 410                 415

Thr Gln Glu Leu Asp Val Arg Lys Glu Arg Gly Glu Ile Leu Ile Asp
            420                 425                 430

Glu Leu Met Asp Ala Ile Lys Lys Val Lys Asn Val Pro Asp Glu Asn
        435                 440                 445

Arg Leu Lys Leu Ile Glu Asn Ile Leu Gly Arg Ile Asp Thr Asp Lys
    450                 455                 460

Asp Arg His Ile Lys Val Glu Asp Val Leu Lys Val Ile Asp Ile Val
465                 470                 475                 480

Glu Lys Glu Asp Gly Ile Met Ser Thr Lys Gln Leu Asp Glu Leu Val
                485                 490                 495

Gln Leu Leu Lys Lys Glu Glu Val Ile Glu Leu Glu Glu Lys Lys Val
            500                 505                 510

Lys Gln Glu Ser Gln Gln Lys Ser Phe Val Pro Pro Ser Glu The Leu
        515                 520                 525

His Leu Glu Ser Ser Gln Gln Lys Ser Thr Val Pro Ser Ser Gly His
    530                 535                 540

Glu Ala Lys Val Ser Glu Asp Asp Leu Asn Val Lys Asn Lys Asn Leu
545                 550                 555                 560

Glu Glu Ser Thr Lys Thr Glu Cys Gly Ala Ile Asp Glu Glu His Arg
                565                 570                 575

Arg Glu His Cys Gln Tyr Pro Asp Ile Thr
            580                 585
```

(2) INFORMATION FOR SEQ ID NO: 31:

(i) SEQUENCE CHARACTERISTICS:
- (A) LENGTH: 293 base pairs
- (B) TYPE: nucleic acid
- (C) STRANDEDNESS: single
- (D) TOPOLOGY: linear (ii) MOLECULE TYPE: cDNA (xi) SEQUENCE DESCRIPTION: SEQ ID NO: 31:

```
CCCGGGCTGC AGGAATTCGG CACGAGATGA GAATGGAAAT GTGATTAGCT ATACTGATCA     60
AAATGGAAAC ATTATCAGTA CTACTGATGA GAATGGAAAT GTGATTAGCA TTACTGATGA    120
AAATGGAAAT GTGATTAGCA TTACTGATGA AAATGGAAAC ATTATCAGTA CTACTGATGA    180
GAATGGAAAT GTGATTAGCA TTACTGATGA AAATGGAAAT GTGATTAGCA TTACTGATGA    240
AAATGGAAAC ATTATTAGTA CTACTGATGA GAATGGAAAT GTGATTAGCA ATA           293
```

(2) INFORMATION FOR SEQ ID NO: 32:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 32:

```
TTGGAAACAG CTATGACCAT GATTACCCCA AGCTCGAAAG TTAAVCCCTC ACTHARAGGG     60
GAACAAAAGT CTGGAGCTCC ACCCGCGGAT GGCGGCCGCB TCTAGAACCT AGTGGACTCC    120
CCCGGSGCTG CAGGAATTCG GGCACGAGCT CCAGCTAGCC ATATACATTC ATCCAAAATG    180
AAGTTGSAAT GTGTCCTACC CGGCAACGGG ATGCCAGAAA TTGTKTCGAA ATKTGTGGAC    240
GAGCACAAGC TTCGTGTCTK TCTATGAAAA ACGTATGGGA GCAGAAGTCG AGGGCCGACA    300
TCCTCGGCGA TGAATGGARA GGTTATGTGC TCCGA                               335
```

(2) INFORMATION FOR SEQ ID NO: 33:

(i) SEQUENCE CHARACTERISTICS:
(A) LENGTH: 396 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 33:

```
ATAGCTTTTA ATATTTTTAA TTGATGTATT GCTCAATGGT GATTTCTGTT TATTAAACTG     60
AGTTACCAAT ATGCTCGCTT CAATAGACAT AGCAAATGAA AGCATTCCGT ATCCTCAAGC    120
GTTACCAAAC TAACATTAAG GAGTTAAATA AATGTTGTTT CCAATAAATA TAATGGGAAA    180
AACATTTAAT ATTTGTTCCA ATTTGTATTT ATTTTTACTA CAATTATATA CAATAAAATA    240
TTTTTATATA TATTTTATAA AGTTTATGAT GCAGGAGAGA AAATAATGTT AAGAATATAG    300
GTAATGTGTA TATATAAATG TTTGACAAGC ATGTTCTAGT TAAATAATAA AAGAATATAG    360
AAATCTACTT AAAAAAAAAA AAAAAAAAAA AAAAAA                              396
```

(2) INFORMATION FOR SEQ ID NO: 34:

(i) SEQUENCE CHARACTERISTICS:
(A) LENGTH: 285 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 34:

-continued

```
GGAAAGCGAA GAATGAAAAG GGGAAACAAA AAAAGAAAAG ACGAAGGAGT GGAGAGATAA     60

AACGGAGGCA AAGAAGAAAA TGAGGATGCA AAAGAAAGGT AATAAAAGAG ATGAAAAGAA    120

GGAAAAAGGA AATAAGAAAG AAAGAGTGAG GGAAAAATAA AGACAGAGGC GAAGCAAAAA    180

AGGAGGAGAA ATAGAGATTA AAAAAGAAAT ACAGCGAAGA AACCAGGAAA GCGATAAAGA    240

AAAAAAAAGA AAAAAAGAGA GCAGTGAAAA AAAAAAAAAA AAAAA                    285
```

(2) INFORMATION FOR SEQ ID NO: 35:

```
     (i) SEQUENCE CHARACTERISTICS:
          (A) LENGTH: 228 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO: 35:

CAGATATTTA CTAAAYATTG TGAAAYAAAT CATTTTCAAA ATGGTSTCCA GGAGAGATAA     60

TGCTCTTGCC ATCAATGGCT TTATAGGGGG CTSCACAAGY CTTTTTTCGA ATGAAAAGAA    120

GTCTTAGATA ASATSGTAGA TRACATCTCT GRCTSMATAT GAGAACARCA GAAGCAAAAA    180

TAGCCAAGGR TNGCRAAATT GATATGMTTS CYGCTGTAAT TCGAAAAAAA AAAAA         228
```

(2) INFORMATION FOR SEQ ID NO: 36:

```
     (i) SEQUENCE CHARACTERISTICS:
          (A) LENGTH: 339 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..339

    (xi) SEQUENCE DESCRIPTION: SEQ ID NO: 36:

CTT CGT GTC AAC CGC TGG GTC AGA CCT GTT ATT GCT ATG CAC CCA ACC       48
Leu Arg Val Asn Arg Trp Val Arg Pro Val Ile Ala Met His Pro Thr
  1               5                  10                  15

ATG ACT CTT GCT GAA CGT CTC GGC AAA AAA GCT TTG CGC GAC CAA TAT       96
Met Thr Leu Ala Glu Arg Leu Gly Lys Lys Ala Leu Arg Asp Gln Tyr
             20                  25                  30

GCT CCC GTT TGC TCC ATT GGA CAA CGT AAC ATC AAC ACC TTT GAC AAC      144
Ala Pro Val Cys Ser Ile Gly Gln Arg Asn Ile Asn Thr Phe Asp Asn
         35                  40                  45

ATG ACC TTC CCC GCT CAA TTC GGA AAA TGC TGG CAC GCT TTG TTG CAA      192
Met Thr Phe Pro Ala Gln Phe Gly Lys Cys Trp His Ala Leu Leu Gln
     50                  55                  60

ACT GTT CCC CAA AAG TAT TCC GAA GAA CGT GAA TAC AGC GAA GAA CAA      240
Thr Val Pro Gln Lys Tyr Ser Glu Glu Arg Glu Tyr Ser Glu Glu Glu
 65                  70                  75                  80

CAA TAC GAC CGT CAA ATG TCC GTC CTC GTT CGT GAA AAC GGC GAA GAA      288
Gln Tyr Asp Arg Gln Met Ser Val Leu Val Arg Glu Asn Gly Gly Glu
                 85                  90                  95

AAA AGA CGT TAT GAT TGT CTT GGG CAA CCG TTA CAA CAA TTG AAT TGC      336
Lys Arg Arg Tyr Asp Cys Leu Gly Gln Pro Leu Gln Gln Leu Asn Cys
            100                 105                 110

AAT                                                                  339
Asn
```

(2) INFORMATION FOR SEQ ID NO: 37:

(i) SEQUENCE CHARACTERISTICS:
(A) LENGTH: 113 amino acids
(B) TYPE: amino acid
(D) TOPOLOGY: linear (ii) MOLECULE TYPE: protein (xi) SEQUENCE DESCRIPTION: SEQ ID NO: 37:

```
Leu Arg Val Asn Arg Trp Val Arg Pro Val Ile Ala Met His Pro Thr
  1               5                  10                  15

Met Thr Leu Ala Glu Arg Leu Gly Lys Lys Ala Leu Arg Asp Gln Tyr
             20                  25                  30

Ala Pro Val Cys Ser Ile Gly Gln Arg Asn Ile Asn Thr Phe Asp Asn
         35                  40                  45

Met Thr Phe Pro Ala Gln Phe Gly Lys Cys Trp His Ala Leu Leu Gln
     50                  55                  60

Thr Val Pro Gln Lys Tyr Ser Glu Glu Arg Glu Tyr Ser Glu Glu Gln
 65                  70                  75                  80

Gln Tyr Asp Arg Gln Met Ser Val Leu Val Arg Glu Asn Gly Glu Glu
                 85                  90                  95

Lys Arg Arg Tyr Asp Cys Leu Gly Gln Pro Leu Gln Gln Leu Asn Cys
            100                 105                 110

Asn
```

(2) INFORMATION FOR SEQ ID NO: 38:

(i) SEQUENCE CHARACTERISTICS:
(A) LENGTH: 493 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..390

(xi) SEQUENCE DESCRIPTION: SEQ ID NO: 38:

```
TCC AGC TCC TCC AGC TCC AGC AGT GAC TCT TCC AGC TCC AGC AGC TCT       48
Ser Ser Ser Ser Ser Ser Ser Ser Asp Ser Ser Ser Ser Ser Ser Ser
  1               5                  10                  15

TCC TCT TCC AGC TCC AGC AGC TCC TCT TCT GAA TCT TCC GAA GAA AAA       96
Ser Ser Ser Ser Ser Ser Ser Ser Ser Ser Glu Ser Ser Glu Glu Lys
             20                  25                  30

ACC TCC CAC AAA AAA TCC GAA AAG AAG GAA CAC AAA TCC TGC TCC ATC      144
Thr Ser His Lys Lys Ser Glu Lys Lys Glu His Lys Ser Cys Ser Ile
         35                  40                  45

AAG AAG CAA GTA CAA TTC GTA GAA AAA GAC GGT AAA CTC TGC TTC AGC      192
Lys Lys Gln Val Gln Phe Val Glu Lys Asp Gly Lys Leu Cys Phe Ser
     50                  55                  60

ATC CGT CCC TTG GCC GCT TGC CAA AAA CAC TGC AAA GCC ACT GAA ACC      240
Ile Arg Pro Leu Ala Ala Cys Gln Lys His Cys Lys Ala Thr Glu Thr
 65                  70                  75                  80

ACT CAA ATG GAA GTC GAA GTA TAC TGC CCC TCT GGC AGC CTT GCT GAA      288
Thr Gln Met Glu Val Glu Val Tyr Cys Pro Ser Gly Ser Leu Ala Glu
                 85                  90                  95

CTT TAC AAA CAA AAG ATC CTT AAG GGA GCC AAC CCC GAC TTG AGC GAC      336
Leu Tyr Lys Gln Lys Ile Leu Lys Gly Ala Asn Pro Asp Leu Ser Asp
```

-continued

```
            100                 105                 110

AAG ACT CCT TCC AGA ATC TTG AAA TTC AAG GTT CCC AAA GCT TGC ACC       384
Lys Thr Pro Ser Arg Ile Leu Lys Phe Lys Val Pro Lys Ala Cys Thr
        115                 120                 125

GCT TAC TAAATCTGAA ATAAATTACA TGGATTAGTT CATTTCTGAT GTAGTGCAAT       440
Ala Tyr
    130

TAGTTCGATA ATAAATTATT CAATGAGCAT TTAAAAAAAA AAAAAAAAAA AAC           493
```

(2) INFORMATION FOR SEQ ID NO: 39:

(i) SEQUENCE CHARACTERISTICS:
(A) LENGTH: 130 amino acids
(B) TYPE: amino acid
(D) TOPOLOGY: linear (ii) MOLECULE TYPE: protein (xi) SEQUENCE DESCRIPTION: SEQ ID NO: 39:

```
Ser Ser Ser Ser Ser Ser Ser Ser Asp Ser Ser Ser Ser Ser Ser Ser
  1               5                  10                  15

Ser Ser Ser Ser Ser Ser Ser Ser Ser Ser Glu Ser Ser Glu Glu Lys
             20                  25                  30

Thr Ser His Lys Lys Ser Glu Lys Lys Glu His Lys Ser Cys Ser Ile
        35                  40                  45

Lys Lys Gln Val Gln Phe Val Glu Lys Asp Gly Lys Leu Cys Phe Ser
     50                  55                  60

Ile Arg Pro Leu Ala Ala Cys Gln Lys His Cys Lys Ala Thr Glu Thr
 65                  70                  75                  80

Thr Gln Met Glu Val Glu Val Tyr Cys Pro Ser Gly Ser Leu Ala Glu
                 85                  90                  95

Leu Tyr Lys Gln Lys Ile Leu Lys Gly Ala Asn Pro Asp Leu Ser Asp
            100                 105                 110

Lys Thr Pro Ser Arg Ile Leu Lys Phe Lys Val Pro Lys Ala Cys Thr
        115                 120                 125

Ala Tyr
    130
```

(2) INFORMATION FOR SEQ ID NO: 40:

(i) SEQUENCE CHARACTERISTICS:
(A) LENGTH: 306 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 40:

```
GTAGTGCCAT CATTCGTAAA CSTTYTGACG GTKGGGCGCT GTATWGGTGC TGCCTGGAAA      60

TTGCATCGAT GCACTWCCGT GTCGGGCGCA WATAGTGCKK TGGSCCCTGT CTGMTTATAG     120

ACATTCAGGG CGCSGGSAKT AGCCATGTTC ATGGCTCMCA AWMTGCATTC ACAGTGGGGT     180

CACATTTCAG TCGCATGATT KMTCAARTTA GTATMWGADA TATATTTTTA TCATACTAAG     240

TAGTGAGCDA ATAACACGCG ARWWACRAAC ACCGAATATC TTKAGTTTTT GCACAGATAT     300

KTGTAA                                                                306
```

(2) INFORMATION FOR SEQ ID NO: 41:

(i) SEQUENCE CHARACTERISTICS:
(A) LENGTH: 490 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 41:

```
ACCGGATACG TTGCCAATGA CTACGTCACC ACCAATGTTG TTTCCACTCC AGTTACTGGA    60

TACACCACCG GACATCTTGC TAATGACTAC GTCACCACCA ATGTTGTATC CACTCCAGTT   120

ACTGGATACA CCACCGGACA TCTTGCCAAT GACTACGTCA CCACCAACGT AGTTTCCGCA   180

CCAGTCACCA CTGGATACAC CACTGGCTAT ACCACCGGTA ATGTCGGATA CACCACCGGA   240

GTTACTGGTT ACACCAACGG AGTTAGTGGA TATACCAATG GACTTAATGG TTATACCACT   300

GGTAGCTATG TCAGCTCCCC AGGATACACT TCTTCTGGAC TTGTCAACGT TTTCTAGATT   360

TATGATTTCG TCTGCCCTCA ATGATGATGA CCACACTTTT TACTTTTTAT GATATTTGGA   420

AAAAATAAAT AACTGGAAGA ATATATAATA ATTTCAAAAT AAAAAAAAAA AAAAAAAAAA   480

CTCGAGGGGG                                                          490
```

(2) INFORMATION FOR SEQ ID NO: 42:

(i) SEQUENCE CHARACTERISTICS:
(A) LENGTH: 616 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 42:

```
AAAAAATCGA AAGAAGGCGT AAAACCAAAA TGGGCACAGA AGGATATTCG GGATTTTAGT    60

GATGCCGACA TGGAGAGGTT ACTGGATCAA TGGGAAGAAG ATGAAGACCC CATTCCAGAA   120

GACGAATTGC CCGAACATCT CAGACCTGAT CCAAAGATCG ACATAAGCAA CATCGATATG   180

AGCAATCCCB AAAACATACT AAAGGCTTCC AAAAAAGGCA AGACTTTGAT GGCATTCGTA   240

CAAGTCAGTG GAAATCCAAC ACAAGAAGAA GCCGAAACCA TCACTAAATT GTGGCAAGGC   300

AGTCTATGGA ATAGTCATAT ACAAGCCGAA AGATATATGG TTAGCGATGA CAGGGCTATA   360

TTTATGTTTA AAGATGGTTC TCAAGCTTGG CCTGCTAAAG ACTTTTTAGT GGAACAAGAA   420

AGGTGTAAAG ATGTTACAAT TGAAAATAAA ATATATCCTG GTAAATATTC TTCGACTAAA   480

GAAGAATTAT AATATAATAT ATTATAATTA TAATCTATAA AATAGATTTG AAATTCTACA   540

TTCATGATCT ACTATGTATG ATATTAATTT ATTAAAAATA ATGTTTTTTC AAGTAAAAAA   600

AAAAAAAAAA AAAAAA                                                   616
```

(2) INFORMATION FOR SEQ ID NO: 43:

(i) SEQUENCE CHARACTERISTICS:
(A) LENGTH: 475 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 43:

```
CTCGTGCGGG ACAGATATAG GACCGGATTC GTTAATTGAT TTGAGTGAAG TGGCTTCTGG    60

TGGTTCTGAT ATTGACACAA AATTTTCCAA TTTAAAAATA GATAAAAAGC CTGTTGCAAC   120
```

```
TTCACAACAA GGAATTGATG AATTTGATAT GTTTGCACAA TCGAGAAACA TTTCTAGTGA    180

GGGATCAACC AGTGCTATGA AGGAAGGACA CGGTTTGGAC TTATTATCAA ATACACATAA    240

AAATGTACCA CCAACAATTC CACAAGCCGG ACAACTTCCA AGGGATTCTG AGTTTGATGA    300

AATTGCTGCT TGGCTTGATG AAAAGGTTGA AGACAAAGCC CAAGTTCCCG AAGACAGTAT    360

TACAAGCAGT GAATTTGATA AATTCCTGGC AGAACGGGCA GCTGTTGCTG AAACTTTGCC    420

AAATATTCCA CCGACTACAC AAAGTAATCA TTCAAATATT GAAGCAAACG ATAAA          475
```

(2) INFORMATION FOR SEQ ID NO: 44:

(i) SEQUENCE CHARACTERISTICS:
(A) LENGTH: 295 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 44:

```
CCGGCACGGG AGGTAGTGAC GAAAAATAAC GATACGGGAC TCATCCGAGG CCCCGTAATC     60

GGAATGAGTA CACTTTAAAT CCTTTAACGA GGATCTATTA GAGGGCCAGT CTGTGTGCCA    120

GCAGCCGCGG TAATTCCAGC TCTAATAGCG TATATTAAAG TTGTTGCGGA TAAAAAGCTC    180

GTAGTTGAAT CTGTGTCCCA CACTGTYGGT TCACCGCTCG CGGTGTTCAA CTGGCATGTC    240

TGTGGGACGT CCTACCGGTG GGCTTAGCCC GTCAAAAGGC GGCCCAACTC AAAAT          295
```

(2) INFORMATION FOR SEQ ID NO: 45:

(i) SEQUENCE CHARACTERISTICS:
(A) LENGTH: 372 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 45:

```
CTGACTAATC CCAGGACTCC TTTATCCTGT TTGCGCAATG TCGATACCCA TCTCACAATG     60

GTTAATGATT TATCGGCTAA ACAGAAGAGT CCTAAGAAGG TTGTTAAAGG TGTTTCTAGA    120

ATACCGACTT TTAGACCCAA GGCTATGAAT GCTGATGTTG AGAATTTTGA TTCGATGAGG    180

TGCGATGTTT GGRACAAAGA CACCAGTGTT GTTATATAAT TACTAAAGCA ATCCACATGT    240

AGCTAATTTT TTTTTTACAA TTTTATTTGT AACTATGTGT ATTTATATGA ATTCTTGTGG    300

AATATAATTT TAAGTTTTTA AATGAAATAT AGATATTATT CTAAAAAAAA AAAACAAAAA    360

AAAAAAAAAA AA                                                        372
```

(2) INFORMATION FOR SEQ ID NO: 46:

(i) SEQUENCE CHARACTERISTICS:
(A) LENGTH: 252 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 46:

```
GGATTCGGCA CGAGAATTTA TTAAGCGCAT TATTTGCAAG TGTAATTTGC TCCTTTAACG     60

CGGAAGTACA AAATCGAATC GTTGGTGGCA ATGATGTAAG TATTTCAAAA ATTGGGTGGC    120
```

```
AAGTATCTAT TCAAAGTAAT AACCAACATT TCTGTGGTGG TTCAATCATT GCTAAAGATT    180

GGGTACTGAC TTCTTCTCAA TGCGTCGTGG ACAAACAAAG TCCACCGAAG GATTTAACTG    240

TTCGTGTTGG AA                                                        252
```

(2) INFORMATION FOR SEQ ID NO: 47:

(i) SEQUENCE CHARACTERISTICS:
(A) LENGTH: 613 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 47:

```
ATTCCTGCTG TTAATAGTAC TAATGCAGTA ATTGCTGCHA GCTGCTGCAC AGAGGTTTTT     60

AAAATGGCAA CAAGTTGTTA CACCCACATG AACAACTACA TGGTATTCAA TGATACCGAT    120

GGGATTTATA CATATACTTA CGAAGCTGAA AGAAAACCTG ACTGTTTAGC TTGTTCACAA    180

ATTCCAAAAA CTATAGAAGT TTCTAATCCT GAAAATATGA CTCTCCAAGA CTTGATTACT    240

TTGTTGTGTG AAGGGGCTGA ATATCAAATG AAGAGCCCAG GTATTGTAGC CTGCAATCGA    300

GGCAAAAACA AAACCTTATA CATGTCAACA GTAGCAAGTA TAGAAGAAAA GACTAAACAG    360

AATCTAACAA AGTCTCTAAA AGAATTAAAT CTAGAAAATG GAATGGAACT GATGGTTGCA    420

GATGTGACGA CACCAAACAC AATATTACTT AAATTAAAAT ATAAGAATGT AATTGAAAAC    480

GATGTTGAGA TGACTTGATA TTTACTTAAA AATGTTATCT TACAATAATT GATAATTTAT    540

ATTTAATACT TTTGGAACTT TGTATTTAAT GATAATAAAT TATTATAAGA ATTAAAAAAA    600

AAAAAAAAAA AAA                                                       613
```

(2) INFORMATION FOR SEQ ID NO: 48:

(i) SEQUENCE CHARACTERISTICS:
(A) LENGTH: 538 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 3..538

(xi) SEQUENCE DESCRIPTION: SEQ ID NO: 48:

```
TT GAT ATT TGC TCT GTT GAG GGT GCC TTA GGA TTT TTA GTG GAA ATG        47
   Asp Ile Cys Ser Val Glu Gly Ala Leu Gly Phe Leu Val Glu Met
     1               5                  10                  15

TTA AAA TAT AAG GCC CCA AGT AAA ACT CTA GCT ATT GTA GAG AAT GCT       95
Leu Lys Tyr Lys Ala Pro Ser Lys Thr Leu Ala Ile Val Glu Asn Ala
                 20                  25                  30

GGT GGA ATA TTA CGA AAT GTA TCT AGT CAT ATA GCC CTT AGA GAG GAC      143
Gly Gly Ile Leu Arg Asn Val Ser Ser His Ile Ala Leu Arg Glu Asp
             35                  40                  45

TAC AGA GAA ATA CTT CGA CAT CAT AAT TGC TTA ACA ATA TTA CTA CAA      191
Tyr Arg Glu Ile Leu Arg His His Asn Cys Leu Thr Ile Leu Leu Gln
         50                  55                  60

CAA TTA AAA TCA CCA AGC CTC ATA ATT GTC AGT AAT GCT TGT GCG ACA      239
Gln Leu Lys Ser Pro Ser Leu Ile Ile Val Ser Asn Ala Cys Gly Thr
     65                  70                  75
```

-continued

```
TTA TGG AAT TTA TCT GCT AGG AAT TCA ACA GAT CAA CAA TTT TTA TGG      287
Leu Trp Asn Leu Ser Ala Arg Asn Ser Thr Asp Gln Gln Phe Leu Trp
 80                 85                  90                  95

GAG AAT GGT GCT GTC CCT TTA TTA AGA AGT TTG ATA TAT TCT AAG CAT      335
Glu Asn Gly Ala Val Pro Leu Leu Arg Ser Leu Ile Tyr Ser Lys His
                100                 105                 110

AAA ATG ATA TCT ATG GGA TCA AGT GCA GCT CTC AAA AAT TTG TTA AAT      383
Lys Met Ile Ser Met Gly Ser Ser Ala Ala Leu Lys Asn Leu Leu Asn
            115                 120                 125

GCA AAA CCT GAG TGC ATC AAT TTC TTA AGT GAT TCT TCT TCT AAA GGA      431
Ala Lys Pro Glu Cys Ile Asn Phe Leu Ser Asp Ser Ser Ser Lys Gly
        130                 135                 140

GTT CCA AAT CTA ACT ACA TTG GGT GTA AGA AAA CAA AAA TCT CTA CAT      479
Val Pro Asn Leu Thr Thr Leu Gly Val Arg Lys Gln Lys Ser Leu His
    145                 150                 155

GAG TTA ATA GAT CAA AAT CTT TCA GAA ACT TGT GAT AAT ATA GAT AGT      527
Glu Leu Ile Asp Gln Asn Leu Ser Glu Thr Cys Asp Asn Ile Asp Ser
160                 165                 170                 175

GTG GCC GCT  AA                                                      538
Val Ala Ala
```

(2) INFORMATION FOR SEQ ID NO: 49:

(i) SEQUENCE CHARACTERISTICS:
(A) LENGTH: 178 amino acids
(B) TYPE: amino acid
(D) TOPOLOGY: linear (ii) MOLECULE TYPE: protein (xi) SEQUENCE DESCRIPTION: SEQ ID NO: 49:

```
Asp Ile Cys Ser Val Glu Gly Ala Leu Gly Phe Leu Val Glu Met Leu
  1               5                  10                  15

Lys Tyr Lys Ala Pro Ser Lys Thr Leu Ala Ile Val Glu Asn Ala Gly
            20                  25                  30

Gly Ile Leu Arg Asn Val Ser Ser His Ile Ala Leu Arg Glu Asp Tyr
        35                  40                  45

Arg Glu Ile Leu Arg His His Asn Cys Leu Thr Ile Leu Leu Gln Gln
    50                  55                  60

Leu Lys Ser Pro Ser Leu Ile Ile Val Ser Asn Ala Cys Gly Thr Leu
 65                  70                  75                  80

Trp Asn Leu Ser Ala Arg Asn Ser Thr Asp Gln Gln Phe Leu Trp Glu
                85                  90                  95

Asn Gly Ala Val Pro Leu Leu Arg Ser Leu Ile Tyr Ser Lys His Lys
            100                 105                 110

Met Ile Ser Met Gly Ser Ser Ala Ala Leu Lys Asn Leu Leu Asn Ala
        115                 120                 125

Lys Pro Glu Cys Ile Asn Phe Leu Ser Asp Ser Ser Ser Lys Gly Val
    130                 135                 140

Pro Asn Leu Thr Thr Leu Gly Val Arg Lys Gln Lys Ser Leu His Glu
145                 150                 155                 160

Leu Ile Asp Gln Asn Leu Ser Glu Thr Cys Asp Asn Ile Asp Ser Val
                165                 170                 175

Ala Ala
```

(2) INFORMATION FOR SEQ ID NO: 50:

(i) SEQUENCE CHARACTERISTICS:
(A) LENGTH: 432 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..388

(xi) SEQUENCE DESCRIPTION: SEQ ID NO: 50:

```
GTT CTT CTT AAA CAG TTG GAC TCT GGA TTG TTA CTT GTT ACA GGT CCC       48
Val Leu Leu Lys Gln Leu Asp Ser Gly Leu Leu Leu Val Thr Gly Pro
  1               5                  10                  15

TTC TTA ATC AAT GCA TGC CCA TTG CGT CGC ATT TCC CAA AAC TAT GTC       96
Phe Leu Ile Asn Ala Cys Pro Leu Arg Arg Ile Ser Gln Asn Tyr Val
             20                  25                  30

ATT GCC ACC TCT ACC CGA TTA GAC GTT AGT GGA GTT AAA TTA CCA GAA      144
Ile Ala Thr Ser Thr Arg Leu Asp Val Ser Gly Val Lys Leu Pro Glu
         35                  40                  45

CAC ATC AAT GAT GAT TAT TTC AAA AGG CAA AAG AAC AAG CGT GCA AAG      192
His Ile Asn Asp Asp Tyr Phe Lys Arg Gln Lys Asn Lys Arg Ala Lys
     50                  55                  60

AAA GAG GAA GGT GAT ATT TTT GCT GCC AAG AAA GAG GCT TAT AAA CCA      240
Lys Glu Glu Gly Asp Ile Phe Ala Ala Lys Lys Glu Ala Tyr Lys Pro
 65                  70                  75                  80

ACT GAG CAA AGG AAG AAT GAC CAA AAG CTT GTA GAC AAA ATG GTT TTA      288
Thr Glu Gln Arg Lys Asn Asp Gln Lys Leu Val Asp Lys Met Val Leu
                 85                  90                  95

GGA GTA ATC AAG AAG CAC CCA GAC CAC AAA CTT TTG TAT ACA TAT TTG      336
Gly Val Ile Lys Lys His Pro Asp His Lys Leu Leu Tyr Thr Tyr Leu
            100                 105                 110

TCA GCT ATG TTT GGT TTG AAA TCT TCC CAA TAT CCA CAT CGT ATG AAG      384
Ser Ala Met Phe Gly Leu Lys Ser Ser Gln Tyr Pro His Arg Met Lys
        115                 120                 125

TTC  T AAATACTATA TTCATAAAAT AAATTGAACT TCTCAAAAAA AAAA              432
Phe
```

(2) INFORMATION FOR SEQ ID NO: 51:

(i) SEQUENCE CHARACTERISTICS:
(A) LENGTH: 129 amino acids
(B) TYPE: amino acid
(D) TOPOLOGY: linear (ii) MOLECULE TYPE: protein (xi) SEQUENCE DESCRIPTION: SEQ ID NO: 51:

```
Val Leu Leu Lys Gln Leu Asp Ser Gly Leu Leu Leu Val Thr Gly Pro
  1               5                  10                  15

Phe Leu Ile Asn Ala Cys Pro Leu Arg Arg Ile Ser Gln Asn Tyr Val
             20                  25                  30

Ile Ala Thr Ser Thr Arg Leu Asp Val Ser Gly Val Lys Leu Pro Glu
         35                  40                  45

His Ile Asn Asp Asp Tyr Phe Lys Arg Gln Lys Asn Lys Arg Ala Lys
     50                  55                  60

Lys Glu Glu Gly Asp Ile Phe Ala Ala Lys Lys Glu Ala Tyr Lys Pro
 65                  70                  75                  80

Thr Glu Gln Arg Lys Asn Asp Gln Lys Leu Val Asp Lys Met Val Leu
                 85                  90                  95

Gly Val Ile Lys Lys His Pro Asp His Lys Leu Leu Tyr Thr Tyr Leu
            100                 105                 110
```

```
Ser Ala Met Phe Gly Leu Lys Ser Ser Gln Tyr Pro His Arg Met Lys
        115                 120                 125

Phe
```

(2) INFORMATION FOR SEQ ID NO: 52:

(i) SEQUENCE CHARACTERISTICS:
(A) LENGTH: 595 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 47..313

(xi) SEQUENCE DESCRIPTION: SEQ ID NO: 52:

```
TGGAAATTCA ATATTTTGTT TTAACATTAA ATTTTTCAAA TTCGAT ATG AAA TTT        55
                                                   Met Lys Phe
                                                    1

TTA CTG GCA ATT TGC GTG TTG TGT GTT TTA TTA AAT CAA GTA TCT ATG      103
Leu Leu Ala Ile Cys Val Leu Cys Val Leu Leu Asn Gln Val Ser Met
      5                  10                  15

TCA AAA ATG GTC ACT GAA AAG TGT AAA TCG GGA GGA AAT AAT CCA AGT      151
Ser Lys Met Val Thr Glu Lys Cys Lys Ser Gly Gly Asn Asn Pro Ser
 20                  25                  30                  35

ACA AAA GAG GTG TCA ATA CCA TCT GGG AAG CTT ACT ATT GAA GAT TTT      199
Thr Lys Glu Val Ser Ile Pro Ser Gly Lys Leu Thr Ile Glu Asp Phe
                 40                  45                  50

TGT ATT GGA AAT CAT CAA AGT TGC AAA ATA TTT TGC AAA AGT CAA TGT      247
Cys Ile Gly Asn His Gln Ser Cys Lys Ile Phe Cys Lys Ser Gln Cys
             55                  60                  65

GGA TTT GGA GGT GGT GCT TGT GGA AAC GGT GGT TCA ACA CGA CCA AAT      295
Gly Phe Gly Gly Gly Ala Cys Gly Asn Gly Gly Ser Thr Arg Pro Asn
         70                  75                  80

CAA AAA CAC TGT TAT TGC GA ATAACCATAT TCCGGATGAA AGACCATGAT          345
Gln Lys His Cys Tyr Cys
     85

GATATAAATT ACTAAAATTA TGCTAGATAG CAATCATAAA ATTTTGAAGTGAT            405

CCTAACATGT TTTGCCTCCA ATTTATTTTA ACAGCAAATT GCTGGGAACTCCG            465

TAACAAAATG TTCAAGAAAT ACTGAATGTT TACAAATAGA TTATTATAAAACA            525

TTGTCTAATA TTTATAAGAA TTATATAAAC TGAATTGCAA AAGTTGAAAAAAA            585

AAAAAAAAAA                                                           595
```

(2) INFORMATION FOR SEQ ID NO: 53:

(i) SEQUENCE CHARACTERISTICS:
(A) LENGTH: 89 amino acids
(B) TYPE: amino acid
(D) TOPOLOGY: linear (ii) MOLECULE TYPE: protein (xi) SEQUENCE DESCRIPTION: SEQ ID NO: 53:

```
Met Lys Phe Leu Leu Ala Ile Cys Val Leu Cys Val Leu Leu Asn Gln
  1               5                  10                  15

Val Ser Met Ser Lys Met Val Thr Glu Lys Cys Lys Ser Gly Gly Asn
             20                  25                  30
```

```
Asn Pro Ser Thr Lys Glu Val Ser Ile Pro Ser Gly Lys Leu Thr Ile
        35                  40                  45

Glu Asp Phe Cys Ile Gly Asn His Gln Ser Cys Lys Ile Phe Cys Lys
    50                  55                  60

Ser Gln Cys Gly Phe Gly Gly Gly Ala Cys Gly Asn Gly Gly Ser Thr
65                  70                  75                  80

Arg Pro Asn Gln Lys His Cys Tyr Cys
                85
```

(2) INFORMATION FOR SEQ ID NO: 54:

(i) SEQUENCE CHARACTERISTICS:
(A) LENGTH: 595 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 54:

```
TTTTTTTTTT TTTTTTTTTT TTTTCAACTT TTGCAATTCA GTTTATATAA TTCTTATAAA      60

TATTAGACAA TGTTACAATA TTTATAATAA TCTATTTGTA AACATTCAGT ATTTCTTGAA     120

CATTTTGTTA CGGTACGGTA AGTTCCCAGC AATTTGCTGT TAAAATAAAT TGGAGGCAAA     180

ACATGTTAGG ATCATTGAAA ACTTCAAAAT TTTATGATTG CTATCTAGCA TAATTTTAGT     240

AATTTATATC AATTTGGTCT TTCATCCGGA ATATGGTTAT TCGCAATAAC AGTGTTTTTG     300

ATTTGGTCGT GTTGAACCAC CGTTTCCACA AGCACCACCT CCAAATCCAC ATTGACTTTT     360

GCAAAATATT TTGCAACTTT GATGATTTCC AATACAAAAA TCTTCAATAG TAAGCTTCCC     420

AGATGGTATT GACACCTCTT TTGTACTTGG ATTATTTCCT CCCGATTTAC ACTTTTCAGT     480

GACCATTTTT GACATAGATA CTTGATTTAA TAAAACACAC AACACGCAAA TTGCCAGTAA     540

AAATTTCATA TCGAATTTGA AAAATTTAAT GTTAAAACAA AATATTGAAT TTCCA          595
```

(2) INFORMATION FOR SEQ ID NO: 55:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..270

(xi) SEQUENCE DESCRIPTION: SEQ ID NO: 55:

```
ATG AAA TTT TTA CTG GCA ATT TGC GTG TTG TGT GTT TTA TTA AAT CAA       48
Met Lys Phe Leu Leu Ala Ile Cys Val Leu Cys Val Leu Leu Asn Gln
  1               5                  10                  15

GTA TCT ATG TCA AAA ATG GTC ACT GAA AAG TGT AAA TCG GGA GGA AAT       96
Val Ser Met Ser Lys Met Val Thr Glu Lys Cys Lys Ser Gly Gly Asn
             20                  25                  30

AAT CCA AGT ACA AAA GAG GTG TCA ATA CCA TCT GGG AAG CTT ACT ATT      144
Asn Pro Ser Thr Lys Glu Val Ser Ile Pro Ser Gly Lys Leu Thr Ile
        35                  40                  45

GAA GAT TTT TGT ATT GGA AAT CAT CAA AGT TGC AAA ATA TTT TGC AAA      192
Glu Asp Phe Cys Ile Gly Asn His Gln Ser Cys Lys Ile Phe Cys Lys
    50                  55                  60

AGT CAA TGT GGA TTT GGA GGT GGT GCT TGT GGA AAC GGT GGT TCA ACA      240
```

-continued

```
Ser Gln Cys Gly Phe Gly Gly Gly Ala Cys Gly Asn Gly Gly Ser Thr
 65                 70                  75                  80

CGA CCA AAT CAA AAA CAC TGT TAT TGC GAA                              270
Arg Pro Asn Gln Lys His Cys Tyr Cys Glu
                 85                  90


(2) INFORMATION FOR SEQ ID NO: 56:

     (i) SEQUENCE CHARACTERISTICS:
          (A) LENGTH: 90 amino acids
          (B) TYPE: amino acid
          (D) TOPOLOGY: linear

    (ii) MOLECULE TYPE: protein

    (xi) SEQUENCE DESCRIPTION: SEQ ID NO: 56:

Met Lys Phe Leu Leu Ala Ile Cys Val Leu Cys Val Leu Leu Asn Gln
  1               5                  10                  15

Val Ser Met Ser Lys Met Val Thr Glu Lys Cys Lys Ser Gly Gly Asn
             20                  25                  30

Asn Pro Ser Thr Lys Glu Val Ser Ile Pro Ser Gly Lys Leu Thr Ile
         35                  40                  45

Glu Asp Phe Cys Ile Gly Asn His Gln Ser Cys Lys Ile Phe Cys Lys
     50                  55                  60

Ser Gln Cys Gly Phe Gly Gly Gly Ala Cys Gly Asn Gly Gly Ser Thr
 65                  70                  75                  80

Arg Pro Asn Gln Lys His Cys Tyr Cys Glu
                 85                  90


(2) INFORMATION FOR SEQ ID NO: 57:

     (i) SEQUENCE CHARACTERISTICS:
          (A) LENGTH: 270 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO: 57:

TTCGCAATAA CAGTGTTTTT GATTTGGTCG TGTTGAACCA CCGTTTCCAC AAGCACCACC      60

TCCAAATCCA CATTGACTTT TGCAAAATAT TTTGCAACTT TGATGATTTC CAATACAAAA     120

ATCTTCAATA GTAAGCTTCC CAGATGGTAT TGACACCTCT TTTGTACTTG GATTATTTCC     180

TCCCGATTTA CACTTTTCAG TGACCATTTT TGACATAGAT ACTTGATTTA ATAAAACACA     240

CAACACGCAA ATTGCCAGTA AAAATTTCAT                                      270


(2) INFORMATION FOR SEQ ID NO: 58:

     (i) SEQUENCE CHARACTERISTICS:
          (A) LENGTH: 213 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..213

    (xi) SEQUENCE DESCRIPTION: SEQ ID NO: 58:

TCA AAA ATG GTC ACT GAA AAG TGT AAA TCG GGA GGA AAT AAT CCA AGT       48
Ser Lys Met Val Thr Glu Lys Cys Lys Ser Gly Gly Asn Asn Pro Ser
```

-continued

```
  1               5                  10                  15

ACA AAA GAG GTG TCA ATA CCA TCT GGG AAG CTT ACT ATT GAA GAT TTT       96
Thr Lys Glu Val Ser Ile Pro Ser Gly Lys Leu Thr Ile Glu Asp Phe
             20                  25                  30

TGT ATT GGA AAT CAT CAA AGT TGC AAA ATA TTT TGC AAA AGT CAA TGT      144
Cys Ile Gly Asn His Gln Ser Cys Lys Ile Phe Cys Lys Ser Gln Cys
         35                  40                  45

GGA TTT GGA GGT GGT GCT TGT GGA AAC GGT GGT TCA ACA CGA CCA AAT      192
Gly Phe Gly Gly Gly Ala Cys Gly Asn Gly Gly Ser Thr Arg Pro Asn
     50                  55                  60

CAA AAA CAC TGT TAT TGC GAA                                          213
Gln Lys His Cys Tyr Cys Glu
 65                  70
```

(2) INFORMATION FOR SEQ ID NO: 59:

(i) SEQUENCE CHARACTERISTICS:
(A) LENGTH: 71 amino acids
(B) TYPE: amino acid
(D) TOPOLOGY: linear (ii) MOLECULE TYPE: protein (xi) SEQUENCE DESCRIPTION: SEQ ID NO: 59:

```
Ser Lys Met Val Thr Glu Lys Cys Lys Ser Gly Gly Asn Asn Pro Ser
  1               5                  10                  15

Thr Lys Glu Val Ser Ile Pro Ser Gly Lys Leu Thr Ile Glu Asp Phe
             20                  25                  30

Cys Ile Gly Asn His Gln Ser Cys Lys Ile Phe Cys Lys Ser Gln Cys
         35                  40                  45

Gly Phe Gly Gly Gly Ala Cys Gly Asn Gly Gly Ser Thr Arg Pro Asn
     50                  55                  60

Gln Lys His Cys Tyr Cys Glu
 65                  70
```

(2) INFORMATION FOR SEQ ID NO: 60:

(i) SEQUENCE CHARACTERISTICS:
(A) LENGTH: 213 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 60:

```
TTCGCAATAA CAGTGTTTTT GATTTGGTCG TGTTGAACCA CCGTTTCCAC AAGCACCACC     60

TCCAAATCCA CATTGACTTT TGCAAAATAT TTTGCAACTT TGATGATTTC CAATACAAAA    120

ATCTTCAATA GTAAGCTTCC CAGATGGTAT TGACACCTCT TTTGTACTTG GATTATTTCC    180

TCCCGATTTA CACTTTTCAG TGACCATTTT TGA                                 213
```

(2) INFORMATION FOR SEQ ID NO: 61:

(i) SEQUENCE CHARACTERISTICS:
(A) LENGTH: 1007 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS (B) LOCATION: 1..465

(xi) SEQUENCE DESCRIPTION: SEQ ID NO: 61:

```
TGG AAA GTT AAT AAA AAA TGT ACA TCA GGT GGA AAA AAT CAA GAT AGA       48
Trp Lys Val Asn Lys Lys Cys Thr Ser Gly Gly Lys Asn Gln Asp Arg
  1               5                  10                  15

AAA CTC GAT CAA ATA ATT CAA AAA GGC CAA CAA GTT AAA ATC CAA AAT       96
Lys Leu Asp Gln Ile Ile Gln Lys Gly Gln Gln Val Lys Ile Gln Asn
             20                  25                  30

ATT TGC AAA TTA ATA CGA GAT AAA CCA CAT ACA AAT CAA GAG AAA GAA      144
Ile Cys Lys Leu Ile Arg Asp Lys Pro His Thr Asn Gln Glu Lys Glu
         35                  40                  45

AAA TGT ATG AAA TTT TGC AAA AAA GTT TGC AAA GGT TAT AGA GGA GCT      192
Lys Cys Met Lys Phe Cys Lys Lys Val Cys Lys Gly Tyr Arg Gly Ala
     50                  55                  60

TGT GAT GGC AAT ATT TGC TAC TGC AGC AGG CCA AGT AAT TTA GGT CCT      240
Cys Asp Gly Asn Ile Cys Tyr Cys Ser Arg Pro Ser Asn Leu Gly Pro
 65                  70                  75                  80

GAT TGG AAA GTA AGC AAA GAA TGC AAA GAT CCC AAT AAC AAA GAT TCT      288
Asp Trp Lys Val Ser Lys Glu Cys Lys Asp Pro Asn Asn Lys Asp Ser
                 85                  90                  95

CGT CCT ACG GAA ATA GTT CCA TAT CGA CAA CAA TTA GCA ATT CCA AAT      336
Arg Pro Thr Glu Ile Val Pro Tyr Arg Gln Gln Leu Ala Ile Pro Asn
            100                 105                 110

ATT TGC AAA CTA AAA AAT TCA GAG ACC AAT GAA GAT TCC AAA TGC AAA      384
Ile Cys Lys Leu Lys Asn Ser Glu Thr Asn Glu Asp Ser Lys Cys Lys
        115                 120                 125

AAA CAT TGC AAA GAA AAA TGT CGT GGT GGA AAT GAT GCT GGA TGT GAT      432
Lys His Cys Lys Glu Lys Cys Arg Gly Gly Asn Asp Ala Gly Cys Asp
    130                 135                 140

GGA AAC TTT TGT TAT TGT CGA CCA AAA AAT AAA TAATAATTAT AATAAATAAA    485
Gly Asn Phe Cys Tyr Cys Arg Pro Lys Asn Lys
145                 150                 155

TTGTTATAGT TATTAGTTAT CCCATCACAT ATTAGAAAAG TGGCTTATAA TTTATGAACA    545

ATATAACACA TAAATTAGTT GTGTAATTTC GAATGTTTTT TTCAAATATA AGGCGTTTTT    605

CTAGAATATC TTGATATTAG AAACTAACTT AGATTATTTT GTTGTGTATA AAATATTCAA    665

ATACGTAAGT TATATTGAAC AAAGCATTTA GAAGCTACAT TAGATATACT AAATAAGTGC    725

AAAATTGCAT GGAAACCCTT ACTGGATTTA CTACATATTT TCTTCCTAAA TATTGTCTTG    785

GTATTACTCT TATTATATAA AAATTAATAT AAAATTGTAG ACAGAGACGA ATTGGGGTAT    845

TGTTATATAT AAAAAAGTAG TGGATTATTT AATTCTAAAA AAGTTTGCAA AATGTTTCAT    905

ACATAATAAC CGAATATTTT CAAATATATA AATATTGTAA TGAATAAATG CGCATCTGTA    965

TGCTTAATAT AAAAAAAAAA AAAAAAAAAA AAAAAAAAAA AA                      1007
```

(2) INFORMATION FOR SEQ ID NO: 62:

(i) SEQUENCE CHARACTERISTICS:
(A) LENGTH: 155 amino acids
(B) TYPE: amino acid
(D) TOPOLOGY: linear (ii) MOLECULE TYPE: protein (xi) SEQUENCE DESCRIPTION: SEQ ID NO: 62:

```
Trp Lys Val Asn Lys Lys Cys Thr Ser Gly Gly Lys Asn Gln Asp Arg
  1               5                  10                  15

Lys Leu Asp Gln Ile Ile Gln Lys Gly Gln Gln Val Lys Ile Gln Asn
             20                  25                  30
```

-continued

```
Ile Cys Lys Leu Ile Arg Asp Lys Pro His Thr Asn Gln Glu Lys Glu
        35                  40                  45

Lys Cys Met Lys Phe Cys Lys Lys Val Cys Lys Gly Tyr Arg Gly Ala
    50                  55                  60

Cys Asp Gly Asn Ile Cys Tyr Cys Ser Arg Pro Ser Asn Leu Gly Pro
 65                 70                  75                  80

Asp Trp Lys Val Ser Lys Glu Cys Lys Asp Pro Asn Asn Lys Asp Ser
                85                  90                  95

Arg Pro Thr Glu Ile Val Pro Tyr Arg Gln Gln Leu Ala Ile Pro Asn
            100                 105                 110

Ile Cys Lys Leu Lys Asn Ser Glu Thr Asn Glu Asp Ser Lys Cys Lys
        115                 120                 125

Lys His Cys Lys Glu Lys Cys Arg Gly Gly Asn Asp Ala Gly Cys Asp
    130                 135                 140

Gly Asn Phe Cys Tyr Cys Arg Pro Lys Asn Lys
145                 150                 155
```

(2) INFORMATION FOR SEQ ID NO: 63:

(i) SEQUENCE CHARACTERISTICS:
(A) LENGTH: 1007 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 63:

```
TTTTTTTTTT TTTTTTTTTT TTTTTTTTTT TTATATTAAG CATACAGATG CGCATTTATT     60

CATTACAATA TTTATATATT TGAAAATATT CGGTTATTAT GTATGAAACA TTTTGCAAAC    120

TTTTTTAGAA TTAAATAATC CACTACTTTT TTATATATAA CAATACCCCA ATTCGTCTCT    180

GTCTACAATT TTATATTAAT TTTTATATAA TAAGAGTAAT ACCAAGACAA TATTTAGGAA    240

GAAAATATGT AGTAAATCCA GTAAGGGTTT CCATGCAATT TTGCACTTAT TTAGTATATC    300

TAATGTAGCT TCTAAATGCT TTGTTCAATA TAACTTACGT ATTTGAATAT TTTATACACA    360

ACAAAATAAT CTAAGTTAGT TTCTAATATC AAGATATTCT AGAAAAACGC CTTATATTTG    420

AAAAAAACAT TCGAAATTAC ACAACTAATT TATGTGTTAT ATTGTTCATA AATTATAAGC    480

CACTTTTCTA ATATGTGATG GGATAACTAA TAACTATAAC AATTTATTTA TTATTATTAT    540

TATTTATTTT TTGGTCGACA ATAACAAAAG TTTCCATCAC ATCCAGCATC ATTTCCACCA    600

CGACATTTTT CTTTGCAATG TTTTTTGCAT TTGGAATCTT CATTGGTCTC TGAATTTTTT    660

AGTTTGCAAA TATTTGGAAT TGCTAATTGT TGTCGATATG GAACTATTTC CGTAGAGCGA    720

GAATCTTTGT TATTGGGATC TTTGCATTCT TTGCTTACTT TCCAATCAGG ACCTAAATTA    780

CTTGGCCTGC TGCAGTAGCA AATATTGCCA TCACAAGCTC CTCTATAACC TTTGCAAACT    840

TTTTTGCAAA ATTTCATACA TTTTTCTTTC TCTTGATTTG TATGTGGTTT ATCTCGTATT    900

AATTTGCAAA TATTTTGGAT TTTAACTTGT TGGCCTTTTT GAATTATTTG ATCGAGTTTT    960

CTATCTTGAT TTTTTCCACC TGATGTACAT TTTTTATTAA CTTTCCA                 1007
```

(2) INFORMATION FOR SEQ ID NO: 64:

(i) SEQUENCE CHARACTERISTICS:
(A) LENGTH: 1205 base pairs
(B) TYPE: nucleic acid
(C) STRANDEDNESS: single (D) TOPOLOGY: linear (ii) MOLECULE TYPE: cDNA (ix) FEATURE:
(A) NAME/KEY: CDS
(B) LOCATION: 4..1062

(xi) SEQUENCE DESCRIPTION: SEQ ID NO: 64:

```
GCA GAA TTG AAA TTT GTG TTT GCG ACT GCA CGA GGT ATG TCA CAT ACA       48
    Glu Leu Lys Phe Val Phe Ala Thr Ala Arg Gly Met Ser His Thr
      1               5                  10                  15

CCT TGT GAT TAT CCA GGC GGT CCA AAA ATT ACA CAC AAG TCT GAA GAT       96
Pro Cys Asp Tyr Pro Gly Gly Pro Lys Ile Thr His Lys Ser Glu Asp
                 20                  25                  30

TCA AGC CAA TTG ACA CCG GCA GGT CAA GAA GAG GCA TTA AAA ATT GGC      144
Ser Ser Gln Leu Thr Pro Ala Gly Gln Glu Glu Ala Leu Lys Ile Gly
             35                  40                  45

AAA TTA TTA TCC GAA CAT TAC AGA ACT AAT TTA AAA GTT GAC AAA TGG      192
Lys Leu Leu Ser Glu His Tyr Arg Thr Asn Leu Lys Val Asp Lys Trp
         50                  55                  60

GAT TCA AAT AAA AAT TAT TGG ACA TTA GCT AGT GCT ACG AGA AGA TCT      240
Asp Ser Asn Lys Asn Tyr Trp Thr Leu Ala Ser Ala Thr Arg Arg Ser
     65                  70                  75

CAA GAA GGA GCG CTT ATC ATT GGT TCT GGT CTA GAA GAA AAG GAA AAG      288
Gln Glu Gly Ala Leu Ile Ile Gly Ser Gly Leu Glu Glu Lys Glu Lys
 80                  85                  90                  95

GCA GTT TGG ACA AAA GAG AAA GGA GAT AAA ACC ATA TTT TCT TCG TTT      336
Ala Val Trp Thr Lys Glu Lys Gly Asp Lys Thr Ile Phe Ser Ser Phe
                100                 105                 110

GGT GAA TAT GCT AAA TTT TAT AGT CCA AAA ACT TGT CCA AAC TTC ATA      384
Gly Glu Tyr Ala Lys Phe Tyr Ser Pro Lys Thr Cys Pro Asn Phe Ile
            115                 120                 125

GCA CAA CAG AAA ATA GCA GTA AGA GAC TTG TTA ACA AAA AGT GCA AAA      432
Ala Gln Gln Lys Ile Ala Val Arg Asp Leu Leu Thr Lys Ser Ala Lys
        130                 135                 140

GAT TAT AAA AAT TCA CTT GCA AAA TTA AAA GAA GCG TAT AAA ATA GAT      480
Asp Tyr Lys Asn Ser Leu Ala Lys Leu Lys Glu Ala Tyr Lys Ile Asp
    145                 150                 155

GCG ACG ACA AGC CCT CAG AAT GTT TGG CTG GCA TAT GAA ACT TTG AAT      528
Ala Thr Thr Ser Pro Gln Asn Val Trp Leu Ala Tyr Glu Thr Leu Asn
160                 165                 170                 175

TTA CAA AGC AAG CAA AAT AAC GCT CCA ACA TGG TGG AAT ACT GTA AAC      576
Leu Gln Ser Lys Gln Asn Asn Ala Pro Thr Trp Trp Asn Thr Val Asn
                180                 185                 190

AAA GAT CTA AAA CAA TTC TCT GAG AAA TAT TTA TGG ACC GCC TTG ACT      624
Lys Asp Leu Lys Gln Phe Ser Glu Lys Tyr Leu Trp Thr Ala Leu Thr
            195                 200                 205

TCT AAT GAT AAT CTT AGA AAG ATG TCA GGA GGT CGT ATG ATT AAC GAT      672
Ser Asn Asp Asn Leu Arg Lys Met Ser Gly Gly Arg Met Ile Asn Asp
        210                 215                 220

ATA TTG AAC GAT ATC GAA AAC ATA AAG AAA GGA GAG GGA CAA CCG GGT      720
Ile Leu Asn Asp Ile Glu Asn Ile Lys Lys Gly Glu Gly Gln Pro Gly
    225                 230                 235

GCT CCA GGA GGA AAG GAA AAC AAA TTA TCA GTG CTG ACC GTT CCT CAA      768
Ala Pro Gly Gly Lys Glu Asn Lys Leu Ser Val Leu Thr Val Pro Gln
240                 245                 250                 255

GCT ATC TTA GCA GCA TTT GTT TCA GCA TTT GCT CCC GAA GGT ACA AAA      816
Ala Ile Leu Ala Ala Phe Val Ser Ala Phe Ala Pro Glu Gly Thr Lys
                260                 265                 270

ATT GAA AAT AAG GAC CTT GAT CCG TCT ACT TTA TAT CCT GGC CAA GGA      864
```

-continued

```
Ile Glu Asn Lys Asp Leu Asp Pro Ser Thr Leu Tyr Pro Gly Gln Gly
            275                 280                 285

GCA CTT CAC GTT ATT GAA CTA CAC CAA GAT AAG AGC GAT TGG AGC ATA      912
Ala Leu His Val Ile Glu Leu His Gln Asp Lys Ser Asp Trp Ser Ile
        290                 295                 300

AAA GTT CTC TAT AGA AAC AAT GAC CAA ATG AAG CTG AAA CCA ATG AAA      960
Lys Val Leu Tyr Arg Asn Asn Asp Gln Met Lys Leu Lys Pro Met Lys
    305                 310                 315

CTT GCA CAA TGC GGT GAC AAG TGT TCT TAT GGT ACT TTC AAA TCA ATG     1008
Leu Ala Gln Cys Gly Asp Lys Cys Ser Tyr Gly Thr Phe Lys Ser Met
320                 325                 330                 335

CTA CAA AAA TAT AAC ATG GAG AAG GAA GCT CAT GAT AAA TTA TGT AAA     1056
Leu Gln Lys Tyr Asn Met Glu Lys Glu Ala His Asp Lys Leu Cys Lys
                340                 345                 350

ACG TCG TAAAAATTAA AAATAAAAAC TTTTCAATAT ATTTTCCGCT AAAATAAATA      1112
Thr Ser

AATATGTTTG TATATTTAAA CTTATCAAAA TAATAGTAGT GTTTTAATAA AGATTTTAAA   1172

TAAATAATTG TAAAAAAAAA AAAAAAAAAA AAA                                 1205
```

(2) INFORMATION FOR SEQ ID NO: 65:

(i) SEQUENCE CHARACTERISTICS:
(A) LENGTH: 353 amino acids
(B) TYPE: amino acid
(D) TOPOLOGY: linear (ii) MOLECULE TYPE: protein (xi) SEQUENCE DESCRIPTION: SEQ ID NO: 65:

```
Glu Leu Lys Phe Val Phe Ala Thr Ala Arg Gly Met Ser His Thr Pro
  1               5                  10                  15

Cys Asp Tyr Pro Gly Gly Pro Lys Ile Thr His Lys Ser Glu Asp Ser
             20                  25                  30

Ser Gln Leu Thr Pro Ala Gly Gln Glu Glu Ala Leu Lys Ile Gly Lys
         35                  40                  45

Leu Leu Ser Glu His Tyr Arg Thr Asn Leu Lys Val Asp Lys Trp Asp
     50                  55                  60

Ser Asn Lys Asn Tyr Trp Thr Leu Ala Ser Ala Thr Arg Arg Ser Gln
 65                  70                  75                  80

Glu Gly Ala Leu Ile Ile Gly Ser Gly Leu Glu Glu Lys Glu Lys Ala
                 85                  90                  95

Val Trp Thr Lys Glu Lys Gly Asp Lys Thr Ile Phe Ser Ser Phe Gly
            100                 105                 110

Glu Tyr Ala Lys Phe Tyr Ser Pro Lys Thr Cys Pro Asn Phe Ile Ala
        115                 120                 125

Gln Gln Lys Ile Ala Val Arg Asp Leu Leu Thr Lys Ser Ala Lys Asp
    130                 135                 140

Tyr Lys Asn Ser Leu Ala Lys Leu Lys Glu Ala Tyr Lys Ile Asn Leu
145                 150                 155                 160

Thr Thr Ser Pro Gln Asn Val Trp Leu Ala Tyr Glu Thr Leu Asn Lys
                165                 170                 175

Gln Ser Lys Gln Asn Asn Ala Pro Thr Trp Trp Asn Thr Val Asp Ile
            180                 185                 190

Asp Leu Lys Gln Phe Ser Glu Lys Tyr Leu Trp Thr Ala Leu The Ser
        195                 200                 205

Asn Asp Asn Leu Arg Lys Met Ser Gly Gly Arg Met Ile Asn Asp Ile
    210                 215                 220
```

```
Leu Asn Asp Ile Glu Asn Ile Lys Lys Gly Glu Gly Gln Pro Gln Ala
225                 230                 235                 240

Pro Gly Gly Lys Glu Asn Lys Leu Ser Val Leu Thr Val Pro Gln Ala
                245                 250                 255

Ile Leu Ala Ala Phe Val Ser Ala Phe Ala Pro Glu Gly Thr Lys Ile
            260                 265                 270

Glu Asn Lys Asp Leu Asp Pro Ser Thr Leu Tyr Pro Gly Gln Gly Ala
        275                 280                 285

Leu His Val Ile Glu Leu His Gln Asp Lys Ser Asp Trp Ser Ile Lys
    290                 295                 300

Val Leu Tyr Arg Asn Asn Asp Gln Met Lys Leu Lys Pro Met Lys Leu
305                 310                 315                 320

Ala Gln Cys Gly Asp Lys Cys Ser Tyr Gly Thr Phe Lys Ser Met Leu
                325                 330                 335

Gln Lys Tyr Asn Met Glu Lys Glu Ala His Asp Lys Leu Cys Lys Thr
            340                 345                 350

Ser
```

(2) INFORMATION FOR SEQ ID NO: 66:

(i) SEQUENCE CHARACTERISTICS:
(A) LENGTH: 1205 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 66:

```
TTTTTTTTTT TTTTTTTTTT TTACAATTAT TTATTTAAAA TCTTTATTAA AACACTACTA     60

TTATTTTGAT AAGTTTAAAT ATACAAACAT ATTTATTTAT TTTAGCGGAA AATATATTGA    120

AAAGTTTTTA TTTTTAATTT TTACGACGTT TTACATAATT TATCATGAGC TTCCTTCTCC    180

ATGTTATATT TTTGTAGCAT TGATTTGAAA GTACCATAAG AACACTTGTC ACCGCATTGT    240

GCAAGTTTCA TTGGTTTCAG CTTCATTTGG TCATTGTTTC TATAGAGAAC TTTTATGCTC    300

CAATCGCTCT TATCTTGGTG TAGTTCAATA ACGTGAAGTG CTCCTTGGCC AGGATATAAA    360

GTAGACGGAT CAAGGTCCTT ATTTTCAATT TTTGTACCTT CGGGAGCAAA TGCTGAAACA    420

AATGCTGCTA AGATAGCTTG AGGAACGGTC AGCACTGATA ATTTGTTTTC CTTTCCTCCT    480

GGAGCACCCG GTTGTCCCTC TCCTTTCTTT ATGTTTTCGA TATCGTTCAA TATATCGTTA    540

ATCATACGAC CTCCTGACAT CTTTCTAAGA TTATCATTAG AAGTCAAGGC GGTCCATAAA    600

TATTTCTCAG AGAATTGTTT TAGATCTTTG TTTACAGTAT TCCACCATGT TGGAGCGTTA    660

TTTTGCTTGC TTTGTAAATT CAAAGTTTCA TATGCCAGCC AAACATTCTG AGGGCTTGTC    720

GTCGCATCTA TTTTATACGC TTCTTTTAAT TTTGCAAGTG AATTTTTATA ATCTTTTGCA    780

CTTTTTGTTA ACAAGTCTCT TACTGCTATT TTCTGTTGTG CTATGAAGTT TGGACAAGTT    840

TTTGGACTAT AAAATTTAGC ATATTCACCA AACGAAGAAA ATATGGTTTT ATCTCCTTTC    900

TCTTTTGTCC AAACTGCCTT TTCCTTTTCT TCTAGACCAG AACCAATGAT ATCCCATTTG    960

TCTTGAGATC TTCTCGTAGC ACTAGCTAAT GTCCAATAAT TTTTATTTGA ATCCCATTTG   1020

TCAACTTTTA AATTAGTTCT GTAATGTTCG GATAATAATT TGCCAATTTT TAATGCCTCT   1080

TCTTGACCTG CCGGTGTCAA TTGGCTTGAA TCTTCAGACT TGTGTGTAAT TTTTGGACCG   1140

CCTGGATAAT CACAAGGTGT ATGTGACATA CCTCGTGCAG TCGCAAACAC AAATTTCAAT   1200
```

```
TCTGC                                                                         1205

(2) INFORMATION FOR SEQ ID NO: 67:

     (i) SEQUENCE CHARACTERISTICS:
          (A) LENGTH: 1059 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..1059

    (xi) SEQUENCE DESCRIPTION: SEQ ID NO: 67:

GAA TTG AAA TTT GTG TTT GCG ACT GCA CGA GGT ATG TCA CAT ACA CCT        48
Glu Leu Lys Phe Val Phe Ala Thr Ala Arg Gly Met Ser His Thr Pro
  1               5                  10                  15

TGT GAT TAT CCA GGC GGT CCA AAA ATT ACA CAC AAG TCT GAA GAT TCA        96
Cys Asp Tyr Pro Gly Gly Pro Lys Ile Thr His Lys Ser Glu Asp Ser
             20                  25                  30

AGC CAA TTG ACA CCG GCA GGT CAA GAA GAG GCA TTA AAA ATT GGC AAA       144
Ser Gln Leu Thr Pro Ala Gly Gln Glu Glu Ala Leu Lys Ile Gly Lys
         35                  40                  45

TTA TTA TCC GAA CAT TAC AGA ACT AAT TTA AAA GTT GAC AAA TGG GAT       192
Leu Leu Ser Glu His Tyr Arg Thr Asn Leu Lys Val Asp Lys Trp Asp
     50                  55                  60

TCA AAT AAA AAT TAT TGG ACA TTA GCT AGT GCT ACG AGA AGA TCT CAA       240
Ser Asn Lys Asn Tyr Trp Thr Leu Ala Ser Ala Thr Arg Arg Ser Gln
 65                  70                  75                  80

GAA GGA GCG CTT ATC ATT GGT TCT GGT CTA GAA GAA AAG GAA AAG GCA       288
Glu Gly Ala Leu Ile Ile Gly Ser Gly Leu Glu Glu Lys Glu Lys Ala
                 85                  90                  95

GTT TGG ACA AAA GAG AAA GGA GAT AAA ACC ATA TTT TCT TCG TTT GGT       336
Val Trp Thr Lys Glu Lys Gly Asp Lys Thr Ile Phe Ser Ser Phe Gly
            100                 105                 110

GAA TAT GCT AAA TTT TAT AGT CCA AAA ACT TGT CCA AAC TTC ATA GCA       384
Glu Tyr Ala Lys Phe Tyr Ser Pro Lys Thr Cys Pro Asn Phe Ile Ala
        115                 120                 125

CAA CAG AAA ATA GCA GTA AGA GAC TTG TTA ACA AAA AGT GCA AAA GAT       432
Gln Gln Lys Ile Ala Val Arg Asp Leu Leu Thr Lys Ser Ala Lys Asp
    130                 135                 140

TAT AAA AAT TCA CTT GCA AAA TTA AAA GAA GCG TAT AAA ATA GAT GCG       480
Tyr Lys Asn Ser Leu Ala Lys Leu Lys Glu Ala Tyr Lys Ile Asp Ala
145                 150                 155                 160

ACG ACA AGC CCT CAG AAT GTT TGG CTG GCA TAT GAA ACT TTG AAT TTA       528
Thr Thr Ser Pro Gln Asn Val Trp Leu Ala Tyr Glu Thr Leu Asn Leu
                165                 170                 175

CAA AGC AAG CAA AAT AAC GCT CCA ACA TGG TGG AAT ACT GTA AAC AAA       576
Gln Ser Lys Gln Asn Asn Ala Pro Thr Trp Trp Asn Thr Val Asn Lys
            180                 185                 190

GAT CTA AAA CAA TTC TCT GAG AAA TAT TTA TGG ACC GCC TTG ACT TCT       624
Asp Leu Lys Gln Phe Ser Glu Lys Tyr Leu Trp Thr Ala Leu Thr Ser
        195                 200                 205

AAT GAT AAT CTT AGA AAG ATG TCA GGA GGT CGT ATG ATT AAC GAT ATA       672
Asn Asp Asn Leu Arg Lys Met Ser Gly Gly Arg Met Ile Asn Asp Ile
    210                 215                 220

TTG AAC GAT ATC GAA AAC ATA AAG AAA GGA GAG GGA CAA CCG GGT GCT       720
Leu Asn Asp Ile Glu Asn Ile Lys Lys Gly Glu Gly Gln Pro Gly Ala
225                 230                 235                 240
```

```
CCA GGA GGA AAG GAA AAC AAA TTA TCA GTG CTG ACC GTT CCT CAA GCT      768
Pro Gly Gly Lys Glu Asn Lys Leu Ser Val Leu Thr Val Pro Gln Ala
                245                 250                 255

ATC TTA GCA GCA TTT GTT TCA GCA TTT GCT CCC GAA GGT ACA AAA ATT      816
Ile Leu Ala Ala Phe Val Ser Ala Phe Ala Pro Glu Gly Thr Lys Ile
            260                 265                 270

GAA AAT AAG GAC CTT GAT CCG TCT ACT TTA TAT CCT GGC CAA GGA GCA      864
Glu Asn Lys Asp Leu Asp Pro Ser Thr Leu Tyr Pro Gly Gln Gly Ala
        275                 280                 285

CTT CAC GTT ATT GAA CTA CAC CAA GAT AAG AGC GAT TGG AGC ATA AAA      912
Leu His Val Ile Glu Leu His Gln Asp Lys Ser Asp Trp Ser Ile Lys
    290                 295                 300

GTT CTC TAT AGA AAC AAT GAC CAA ATG AAG CTG AAA CCA ATG AAA CTT      960
Val Leu Tyr Arg Asn Asn Asp Gln Met Lys Leu Lys Pro Met Lys Leu
305                 310                 315                 320

GCA CAA TGC GGT GAC AAG TGT TCT TAT GGT ACT TTC AAA TCA ATG CTA     1008
Ala Gln Cys Gly Asp Lys Cys Ser Tyr Gly Thr Phe Lys Ser Met Leu
                325                 330                 335

CAA AAA TAT AAC ATG GAG AAG GAA GCT CAT GAT AAA TTA TGT AAA ACG     1056
Gln Lys Tyr Asn Met Glu Lys Glu Ala His Asp Lys Leu Cys Lys Thr
            340                 345                 350

TCG                                                                 1059
Ser
```

(2) INFORMATION FOR SEQ ID NO: 68:

(i) SEQUENCE CHARACTERISTICS:
(A) LENGTH: 353 amino acids
(B) TYPE: amino acid
(D) TOPOLOGY: linear (ii) MOLECULE TYPE: protein (xi) SEQUENCE DESCRIPTION: SEQ ID NO: 68:

```
Glu Leu Lys Phe Val Phe Ala Thr Ala Arg Gly Met Ser His Thr Pro
  1               5                  10                  15

Cys Asp Tyr Pro Gly Gly Pro Lys Ile Thr His Lys Ser Glu Asp Ser
             20                  25                  30

Ser Gln Leu Thr Pro Ala Gly Gln Glu Glu Ala Leu Lys Ile Gly Lys
         35                  40                  45

Leu Leu Ser Glu His Tyr Arg Thr Asn Leu Lys Val Asp Lys Trp Asp
     50                  55                  60

Ser Asn Lys Asn Tyr Trp Thr Leu Ala Ser Ala Thr Arg Arg Ser Gln
 65                  70                  75                  80

Glu Gly Ala Leu Ile Ile Gly Ser Gly Leu Glu Glu Lys Glu Lys Ala
                 85                  90                  95

Val Trp Thr Lys Glu Lys Gly Asp Lys Thr Ile Phe Ser Ser Phe Gly
            100                 105                 110

Glu Tyr Ala Lys Phe Tyr Ser Pro Lys Thr Cys Pro Asn Phe Ile Ala
        115                 120                 125

Gln Gln Lys Ile Ala Val Arg Asp Leu Leu Thr Lys Ser Ala Lys Asp
    130                 135                 140

Tyr Lys Asn Ser Leu Ala Lys Leu Lys Glu Ala Tyr Lys Ile Asn Ala
145                 150                 155                 160

Thr Thr Ser Pro Gln Asn Val Trp Leu Ala Tyr Glu Thr Leu Asp Leu
                165                 170                 175

Gln Ser Lys Gln Asn Asn Ala Pro Thr Trp Trp Asn Thr Val Asn Lys
            180                 185                 190
```

```
Asp Leu Lys Gln Phe Ser Glu Lys Tyr Leu Trp Thr Ala Leu Thr Ser
        195                 200                 205

Asn Asp Asn Leu Arg Lys Met Ser Gly Gly Arg Met Ile Asn Asp Ile
    210                 215                 220

Leu Asn Asp Ile Glu Asn Ile Lys Lys Gly Glu Gly Gln Pro Gly Ala
225                 230                 235                 240

Pro Gly Gly Lys Glu Asn Lys Leu Ser Val Leu Thr Val Pro Gln Ala
                245                 250                 255

Ile Leu Ala Ala Phe Val Ser Ala Phe Ala Pro Glu Gly Thr Lys Ile
            260                 265                 270

Glu Asn Lys Asp Leu Asp Pro Ser Thr Leu Tyr Pro Gly Gln Gly Ala
        275                 280                 285

Leu His Val Ile Glu Leu His Gln Asp Lys Ser Asp Trp Ser Ile Lys
    290                 295                 300

Val Leu Tyr Arg Asn Asn Asp Gln Met Lys Leu Lys Pro Met Lys Leu
305                 310                 315                 320

Ala Gln Cys Gly Asp Lys Cys Ser Tyr Gly Thr Phe Lys Ser Met Leu
                325                 330                 335

Gln Lys Tyr Asn Met Glu Lys Glu Ala His Asp Lys Leu Cys Lys Thr
            340                 345                 350

Ser
```

(2) INFORMATION FOR SEQ ID NO: 69:

(i) SEQUENCE CHARACTERISTICS:
(A) LENGTH: 1059 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 69:

```
CGACGTTTTA CATAATTTAT CATGAGCTTC CTTCTCCATG TTATATTTTT GTAGCATTGA     60

TTTGAAAGTA CCATAAGAAC ACTTGTCACC GCATTGTGCA AGTTTCATTG GTTTCAGCTT    120

CATTTGGTCA TTGTTTCTAT AGAGAACTTT TATGCTCCAA TCGCTCTTAT CTTGGTGTAG    180

TTCAATAACG TGAAGTGCTC CTTGGCCAGG ATATAAAGTA GACGGATCAA GGTCCTTATT    240

TTCAATTTTT GTACCTTCGG GAGCAAATGC TGAAACAAAT GCTGCTAAGA TAGCTTGAGG    300

AACGGTCAGC ACTGATAATT TGTTTTCCTT TCCTCCTGGA GCACCCGGTT GTCCCTCTCC    360

TTTCTTTATG TTTTCGATAT CGTTCAATAT ATCGTTAATC ATACGACCTC CTGACATCTT    420

TCTAAGATTA TCATTAGAAG TCAAGGCGGT CCATAAATAT TTCTCAGAGA ATTGTTTTAG    480

ATCTTTGTTT ACAGTATTCC ACCATGTTGG AGCGTTATTT TGCTTGCTTT GTAAATTCAA    540

AGTTTCATAT GCCAGCCAAA CATTCTGAGG GCTTGTCGTC GCATCTATTT TATACGCTTC    600

TTTTAATTTT GCAAGTGAAT TTTTATAATC TTTTGCACTT TTTGTTAACA AGTTAGCATA    660

TGCTATTTTC TGTTGTGCTA TGAAGTTTGG ACAAGTTTTT GGACTATAAA ATTTAGCATA    720

TTCACCAAAC GAAGAAAATA TGGTTTTATC TCCTTTCTCT TTTGTCCAAA CTGCCTTTTC    780

CTTTTCTTCT AGACCAGAAC CAATGATAAG CGCTCCTTCT TGAGATCTTC TCGTACACCT    840

AGCTAATGTC CAATAATTTT TATTTGAATC CCATTTGTCA ACTTTTAAAT TAGTTCTGTA    900

ATGTTCGGAT AATAATTTGC CAATTTTTAA TGCCTCTTCT TGACCTGCCG GTGTCAATTG    960

GCTTGAATCT TCAGACTTGT GTGTAATTTT TGGACCGCCT GGATAATCAC AAGGTGTATG   1020
```

TGACATACCT CGTGCAGTCG CAAACACAAA TTTCAATTC 1059

(2) INFORMATION FOR SEQ ID NO: 70:

(i) SEQUENCE CHARACTERISTICS:
(A) LENGTH: 25 amino acids
(B) TYPE: amino acid
(C) STRANDEDNESS: <Unknown>
(D) TOPOLOGY: linear (ii) MOLECULE TYPE: peptide (ix) FEATURE:
(A) NAME/KEY: Xaa = any amino acid
(B) LOCATION: 1

(ix) FEATURE:
(A) NAME/KEY: Xaa = any amino acid
(B) LOCATION: 24

(xi) SEQUENCE DESCRIPTION: SEQ ID NO: 70:

```
Xaa Glu Leu Lys Phe Val Phe Val Met Val Lys Gly Pro Asp His Glu
1               5                   10                  15

Ala Cys Asn Tyr Ala Gly Gly Xaa Gln
            20                  25
```

(2) INFORMATION FOR SEQ ID NO: 71:

(i) SEQUENCE CHARACTERISTICS:
(A) LENGTH: 406 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..405

(xi) SEQUENCE DESCRIPTION: SEQ ID NO: 71:

```
ATG GTT AAA GGT CCA GAT CAC GAA GCT TGT AAC TAT GCA GGA GGT CCT       48
Met Val Lys Gly Pro Asp His Glu Ala Cys Asn Tyr Ala Gly Gly Pro
  1               5                  10                  15

CAG TTA ACT ACT CTT CAA GAA AAA GAT AGT GTT CTA ACT GAA GAT GGC       96
Gln Leu Thr Thr Leu Gln Glu Lys Asp Ser Val Leu Thr Glu Asp Gly
             20                  25                  30

AAG ACA GAA GCA TAC GAA TTG GGA AAA CTT TTG GAC AAG GTA TAT AAA      144
Lys Thr Glu Ala Tyr Glu Leu Gly Lys Leu Leu Asp Lys Val Tyr Lys
         35                  40                  45

AAA CAA TTA AAA GTT GAC AAA TGG GAT GCC ACG AAA ACC TAC TGG GCT      192
Lys Gln Leu Lys Val Asp Lys Trp Asp Ala Thr Lys Thr Tyr Trp Ala
     50                  55                  60

GTG TCC ACA AAA GCT ATG CGT ACT AAA GAA GCA GCC TTA ATT GTA GGA      240
Val Ser Thr Lys Ala Met Arg Thr Lys Glu Ala Ala Leu Ile Val Gly
 65                  70                  75                  80

GCA GGA TTG GAA AAT AAT CCT GCA AAA GCT AAA GGT AAT TGG ACA CAA      288
Ala Gly Leu Glu Asn Asn Pro Ala Lys Ala Lys Gly Asn Trp Thr Gln
                 85                  90                  95

CAA CAG CTC GAT TCA ACA CAT TTT GAT GCG ATG CCT GGC TTT TCT AGA      336
Gln Gln Leu Asp Ser Thr His Phe Asp Ala Met Pro Gly Phe Ser Arg
            100                 105                 110

TTT TGG AAT CCT CAA CAA TGT CCG GCA TAT TTC AGA GCG CTC TCG CTA      384
Phe Trp Asn Pro Gln Gln Cys Pro Ala Tyr Phe Arg Ala Leu Ser Leu
        115                 120                 125
```

-continued

```
CAA AAT CAG AAA ATA AAG AAA T                                      406
Gln Asn Gln Lys Ile Lys Lys
    130                 135
```

(2) INFORMATION FOR SEQ ID NO: 72:

(i) SEQUENCE CHARACTERISTICS:
(A) LENGTH: 135 amino acids
(B) TYPE: amino acid
(D) TOPOLOGY: linear (ii) MOLECULE TYPE: protein (xi) SEQUENCE DESCRIPTION: SEQ ID NO: 72:

```
Met Val Lys Gly Pro Asp His Glu Ala Cys Asn Tyr Ala Gly Gly Pro
  1               5                  10                  15

Gln Leu Thr Thr Leu Gln Glu Lys Asp Ser Val Leu Thr Glu Asp Gly
            20                  25                  30

Lys Thr Glu Ala Tyr Glu Leu Gly Lys Leu Leu Asp Lys Val Tyr Lys
        35                  40                  45

Lys Gln Leu Lys Val Asp Lys Trp Asp Ala Thr Lys Thr Tyr Trp Ala
     50                  55                  60

Val Ser Thr Lys Ala Met Arg Thr Lys Glu Ala Ala Leu Ile Val Gly
 65                  70                  75                  80

Ala Gly Leu Glu Asn Asn Pro Ala Lys Ala Lys Gly Asn Trp Thr Gln
                 85                  90                  95

Gln Gln Leu Asp Ser Thr His Phe Asp Ala Met Pro Gly Phe Ser Arg
            100                 105                 110

Phe Trp Asn Pro Gln Gln Cys Pro Ala Tyr Phe Arg Ala Leu Ser Leu
        115                 120                 125

Gln Asn Gln Lys Ile Lys Lys
    130                 135
```

(2) INFORMATION FOR SEQ ID NO: 73:

(i) SEQUENCE CHARACTERISTICS:
(A) LENGTH: 406 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 73:

```
ATTTCTTTAT TTTCTGATTT TGTAGCGAGA GCGCTCTGAA ATATGCCGGA CATTGTTGAT     60

GATTCCAAAA TCTAGAAAAG CCAGGCATCG CATCAAAATG TGTTGAATCG ACGTGTTGTT    120

GTGTCCAATT ACCTTTAGCT TTTGCAGGAT TATTTTCCAA TCCTGCTCCT ACAATTAAGG    180

CTGCTTCTTT AGTACGCATA GCTTTTGTGG ACACAGCCCA GTAGGTTTTC GTGGCATCCC    240

ATTTGTCAAC TTTTAATTGT TTTTTATATA CCTTGTCCAA AAGTTTTCCC AATTCGTATG    300

CTTCTGTCTT GCCATCTTCA GTTAGAACAC TATCTTTTTC TTGAAGAGTA GTTAACTGAG    360

GACCTCCTGC ATAGTTACAA GCTTCGTGAT CTGGACCTTT AACCAT                   406
```

(2) INFORMATION FOR SEQ ID NO: 74:

(i) SEQUENCE CHARACTERISTICS:
(A) LENGTH: 420 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..216

(xi) SEQUENCE DESCRIPTION: SEQ ID NO: 74:

```
GAA GTT ATG GAT AAA TTG CGA AAA CAG GCA CCT CCT AAA ACT GAT GGC       48
Glu Val Met Asp Lys Leu Arg Lys Gln Ala Pro Pro Lys Thr Asp Gly
  1               5                  10                  15

AAT CCT CCA AAA ACA ACC ATA ATG AGT ACA CTT CAA AAG CAA CAA ATA       96
Asn Pro Pro Lys Thr Thr Ile Met Ser Thr Leu Gln Lys Gln Gln Ile
             20                  25                  30

AGT TGC ACA GAA GTG AAA GCG GTT AAC TTA GAA AGT CAT GTT TGT GCT      144
Ser Cys Thr Glu Val Lys Ala Val Asn Leu Glu Ser His Val Cys Ala
         35                  40                  45

TAT GAT TGT AGT CAA CCT GAA ACT GCA GGA ATT ACA TGC AAA GGA AAT      192
Tyr Asp Cys Ser Gln Pro Glu Thr Ala Gly Ile Thr Cys Lys Gly Asn
     50                  55                  60

AAG TGT GAT TGT CCT AAA AAA CGC TAAAAATTTA TTCAAAACAT TTACATTTTT     246
Lys Cys Asp Cys Pro Lys Lys Arg
 65                  70

TATTAATATT CAACTATCAA AAATTCTGTG TTGATTGTTA TTATATTTAT CATAGTTACT    306

AGAAATAAAA TTTTATAACA TTGTTAATTC GAAATTGAAT ACACATAATA TTATAATTAG    366

TGAGGTTAAA AGAAATAAAC CGAATATCCA AATCAAAAAA AAAAAAAAAA AAAA          420
```

(2) INFORMATION FOR SEQ ID NO: 75:

(i) SEQUENCE CHARACTERISTICS:
(A) LENGTH: 72 amino acids
(B) TYPE: amino acid
(D) TOPOLOGY: linear (ii) MOLECULE TYPE: protein (xi) SEQUENCE DESCRIPTION: SEQ ID NO: 75:

```
Glu Val Met Asp Lys Leu Arg Lys Gln Ala Pro Pro Lys Thr Asp Gly
  1               5                  10                  15

Asn Pro Pro Lys Thr Thr Ile Met Ser Thr Leu Gln Lys Gln Gln Ile
             20                  25                  30

Ser Cys Thr Glu Val Lys Ala Val Asn Leu Glu Ser His Val Cys Ala
         35                  40                  45

Tyr Asp Cys Ser Gln Pro Glu Thr Ala Gly Ile Thr Cys Lys Gly Asn
     50                  55                  60

Lys Cys Asp Cys Pro Lys Lys Arg
 65                  70
```

(2) INFORMATION FOR SEQ ID NO: 76:

(i) SEQUENCE CHARACTERISTICS:
(A) LENGTH: 420 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 76:

```
TTTTTTTTTT TTTTTTTTTT GATTTGGATA TTCGGTTTAT TTCTTTTAAC CTCACTAATT     60

ATAATATTAT GTGTATTCAA TTTCGAATTA ACAATGTTAT AAAATTTTAT TTCTAGTAAC    120

TATGATAAAT ATAATAACAA TCAACACAGA ATTTTTGATA GTTGAATATT AATAAAAAAT    180
```

```
GTAAATGTTT TGAATAAATT TTTAGCGTTT TTTAGGACAA TCACACTTAT TTCCTTTGCA    240

TGTAATTCCT GCAGTTTCAG GTTGACTACA ATCATAAGCA CAAACATGAC TTTCTAAGTT    300

AACCGCTTTC ACTTCTGTGC AACTTATTTG TTGCTTTTGA AGTGTACTCA TTATGGTTGT    360

TTTTGGAGGA TTGCCATCAG TTTTAGGAGG TGCCTGTTTT CGCAATTTAT CCATAACTTC    420
```

(2) INFORMATION FOR SEQ ID NO: 77:

(i) SEQUENCE CHARACTERISTICS:
(A) LENGTH: 71 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 77:

```
Ser Lys Met Val Thr Glu Lys Cys Lys Ser Gly Gly Asn Asn Pro Ser
1               5                   10                  15

Thr Lys Glu Val Ser Ile Pro Ser Gly Lys Leu Thr Ile GLu Asp Phe
            20                  25                  30

Cys Ile Gly Asn His Gln Ser Cys Lys Ile Phe Cys Lys Ser Gln Cys
        35                  40                  45

Gly Phe Gly Gly Gly Ala Cys Gly Asn Gly Gly Ser Thr Arg Pro Asn
    50                  55                  60

Gln Lys His Cys Tyr Cys Glu
65                  70
```

(2) INFORMATION FOR SEQ ID NO: 78:

(i) SEQUENCE CHARACTERISTICS:
(A) LENGTH: 25 amino acids
(B) TYPE: amino acid
(C) STRANDEDNESS: <Unknown>
(D) TOPOLOGY: linear (ii) MOLECULE TYPE: peptide (xi) SEQUENCE DESCRIPTION: SEQ ID NO: 78:

```
Asn Asp Lys Leu Gln Phe Val Phe Val Met Ala Arg Gly Pro Asp His
1               5                   10                  15

Glu Ala Cys Asn Tyr Pro Gly Gly Pro
            20                  25
```

(2) INFORMATION FOR SEQ ID NO: 79:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..26
(D) OTHER INFORMATION: /label= primer (xi) SEQUENCE DESCRIPTION: SEQ ID NO: 79:

```
AGTGGATCCG TCAAAAATGG TCACTG                                          26
```

(2) INFORMATION FOR SEQ ID NO: 80:

-continued (i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..28
(D) OTHER INFORMATION: /label= primer (xi) SEQUENCE DESCRIPTION: SEQ ID NO: 80:

CCGGAATTCG GTTATTCGCA ATAACAGT 28

(2) INFORMATION FOR SEQ ID NO: 81:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..54
(D) OTHER INFORMATION: /label= primer (xi) SEQUENCE DESCRIPTION: SEQ ID NO: 81:

GCGCGGATCC GCATATGGAA GACATCTGGA AAGTTAATAA AAAATGTACA TCAG 54

(2) INFORMATION FOR SEQ ID NO: 82:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..45
(D) OTHER INFORMATION: /label= primer (xi) SEQUENCE DESCRIPTION: SEQ ID NO: 82:

CCGGAATTCT TATTTATTTT TTGGTCGACA ATAACAAAAG TTTCC 45

(2) INFORMATION FOR SEQ ID NO: 83:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..46
(D) OTHER INFORMATION: /label= primer (xi) SEQUENCE DESCRIPTION: SEQ ID NO: 83:

AAATTTGTWT TTGTWATGGT WAAAGGWCCW GATCATGAAG C 41

(2) INFORMATION FOR SEQ ID NO: 84:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..37
(D) OTHER INFORMATION: /label= primer (xi) SEQUENCE DESCRIPTION: SEQ ID NO: 84:

CATGAACCWG GWAATACWCG WAARATHAS 29

(2) INFORMATION FOR SEQ ID NO: 85:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..17
(D) OTHER INFORMATION: /label= primer (xi) SEQUENCE DESCRIPTION: SEQ ID NO: 85:

GTAAAACGAC GGCCAGT 17

(2) INFORMATION FOR SEQ ID NO: 86:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..31
(D) OTHER INFORMATION: /label= primer (xi) SEQUENCE DESCRIPTION: SEQ ID NO: 86:

GAAGTWATGG AYAAATTRAG RCARGC 26

(2) INFORMATION FOR SEQ ID NO: 87:

(i) SEQUENCE CHARACTERISTICS:
(A) LENGTH: 19 amino acids
(B) TYPE: amino acid
(C) STRANDEDNESS: <Unknown>
(D) TOPOLOGY: linear (ii) MOLECULE TYPE: peptide (ix) FEATURE:
(A) NAME/KEY: Peptide
(B) LOCATION: 1..19

(xi) SEQUENCE DESCRIPTION: SEQ ID NO: 87:

```
Tyr Phe Asn Lys Leu Val Gln Ser Trp Thr Glu Pro Met Val Phe Lys
1               5                   10                  15

Tyr Pro Tyr
```

-continued

```
(2) INFORMATION FOR SEQ ID NO: 88:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: misc_feature
          (B) LOCATION: 1..24
          (D) OTHER INFORMATION: /label= primer

    (xi) SEQUENCE DESCRIPTION: SEQ ID NO: 88:

GTAATACGAC TCACTATATA GGGC                                              24
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule selected from the group consisting of:

(a) an isolated cDNA or a corresponding RNA molecule comprising a nucleic acid sequence selected from the group consisting of SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:71, SEQ ID NO:73, SEQ ID NO:74, SEQ ID NO:76 and a nucleic acid sequence encoding an amino acid sequence selected from the group consisting of SEQ ID NO:78 and SEQ ID NO:87, wherein said nucleic acid molecule encodes a flea saliva protein; and (b) a nucleic acid molecule comprising a nucleic acid sequence fully complementary to a nucleic acid sequence of (a).

2. An isolated nucleic acid molecule selected from the group consisting of:

(a) an isolated cDNA or a corresponding RNA molecule comprising a nucleic acid sequence encoding an amino acid sequence selected from the group consisting of SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87, wherein said nucleic acid molecule encodes a flea saliva protein; and (b) a nucleic acid molecule comprising a nucleic acid sequence fully complementary to a nucleic acid sequence of (a).

3. The isolated nucleic acid molecule of claims 1 or 2, wherein said nucleic acid molecule is a flea nucleic acid molecule.

4. The isolated nucleic acid molecule of claims 1 or 2, wherein said nucleic acid molecule is selected from the group consisting of Ctenocephalides, Ceratophyllus, Diamanus, Echidnophaga, Nosopsyllus, Pulex, Tunga, Oropsylla, Orchopeus and Xenopsylla nucleic acid molecules.

5. The isolated nucleic acid molecule of claims 1 or 2, wherein said nucleic acid molecule is selected from the group consisting of *Ctenocephalides felis, Ctenocephalides canis, Ceratophyllus pulicidae, Pulex irritans, Oropsylla* (Thrassis) *bacchi, Oropsylla* (Diamanus) *montana, Orchopeus howardi, Xenopsylla cheopis* and *Pulex simulans* nucleic acid molecules.

6. The isolated nucleic acid molecule of claims 1 or 2, wherein said nucleic acid molecule comprises a *Ctenocephalides felis* nucleic acid molecule.

7. The isolated nucleic acid molecule of claim 1, wherein said nucleic acid molecule is selected from the group consisting of $nfspG5_{595}$, $nfspG5_{270}$, $nfspG5_{213}$, $nfspI_{1007}$, $nfspN5_{1205}$, $nfspN6_{406}$ and $nfspJ_{420}$.

8. The isolated nucleic acid molecule of claims 1 or 2, wherein said nucleic acid molecule is a cDNA or a corresponding RNA molecule comprising a nucleic acid sequence that encodes an amino acid sequence selected from the group consisting of SEQ ID NO:53, SEQ ID NO:62, SEQ ID NO:65, SEQ ID NO:70, SEQ ID NO:72, SEQ ID NO:75, SEQ ID NO:77, SEQ ID NO:78 and SEQ ID NO:87.

9. The isolated nucleic acid molecule of claims 1 or 2, wherein said nucleic acid molecule is a cDNA or a corresponding RNA molecule comprising a nucleic acid sequence selected from the group consisting of SEQ ID NO:52, SEQ ID NO:54, SEQ ID NO:55, SEQ ID NO:57, SEQ ID NO:58, SEQ ID NO:60, SEQ ID NO:61, SEQ ID NO:63, SEQ ID NO:64, SEQ ID NO:66, SEQ ID NO:67, SEQ ID NO:69, SEQ ID NO:71, SEQ ID NO:73, SEQ ID NO:74, SEQ ID NO:76 and a nucleic acid sequence encoding an amino acid sequence selected from the group consisting of SEQ ID NO:78 and SEQ ID NO:87.

10. The isolated nucleic acid molecule of claim 1 or 2, wherein said nucleic acid molecule comprises an oligonucleotide.

11. A recombinant molecule comprising a nucleic acid molecule as set forth in claims 1 or 2 operatively linked to a transcription control sequence.

12. A recombinant virus comprising a nucleic acid molecule as set forth in claims 1 or 2.

13. A recombinant cell comprising a nucleic acid molecule as set forth in claims 1 or 2, said cell being capable of expressing said nucleic acid molecule.

* * * * *

UNITED STATES PATENT AND TRADEMARK OFFICE

CERTIFICATE OF CORRECTION

PATENT NO. : 6,368,846 B1
DATED : April 9, 2002
INVENTOR(S) : Hunter et al.

It is certified that error appears in the above-identified patent and that said Letters Patent is hereby corrected as shown below:

Title page,
Item [63], After "Continuation", insert -- in-Part --

Column 140,
Line 35, after "of", insert -- nucleic acid molecule encoding flea saliva protein --
Line 35, delete the term "$nfspG5_{595}$" and insert -- ($nfspG5_{595}$) -- therefor
Line 36, after "$nfspN5_{1205}$," insert -- $nfspN5_{1059}$ --

Signed and Sealed this

Thirtieth Day of July, 2002

*Attest:*

JAMES E. ROGAN

*Attesting Officer* *Director of the United States Patent and Trademark Office*